(12) United States Patent
Gagnon et al.

(10) Patent No.: US 9,114,118 B2
(45) Date of Patent: Aug. 25, 2015

(54) COMPOUNDS AND COMPOSITIONS FOR THE TREATMENT OF CANCER

(75) Inventors: Lyne Gagnon, Laval (CA); Brigitte Grouix, Montreal (CA); Lilianne Geerts, St-Lazare (CA); Pierre Laurin, Ville Mont-Royal (CA); Christopher Penney, Pierrefonds (CA); Boulos Zacharie, Laval (CA)

(73) Assignee: PROMETIC BIOSCIENCES INC., Quebec (CA)

( * ) Notice: Subject to any disclaimer, the term of this patent is extended or adjusted under 35 U.S.C. 154(b) by 0 days.

(21) Appl. No.: 13/882,355

(22) PCT Filed: Oct. 26, 2011

(86) PCT No.: PCT/CA2011/001179
§ 371 (c)(1),
(2), (4) Date: Apr. 29, 2013

(87) PCT Pub. No.: WO2012/097427
PCT Pub. Date: Jul. 26, 2012

(65) Prior Publication Data
US 2013/0217645 A1    Aug. 22, 2013

Related U.S. Application Data

(60) Provisional application No. 61/407,069, filed on Oct. 27, 2010.

(51) Int. Cl.
| | | |
|---|---|---|
| *A01N 27/00* | (2006.01) |
| *A61K 31/015* | (2006.01) |
| *A61K 31/192* | (2006.01) |
| *A61K 31/196* | (2006.01) |
| *A61K 31/22* | (2006.01) |
| *A61K 31/513* | (2006.01) |
| *A61K 31/675* | (2006.01) |
| *A61K 31/7068* | (2006.01) |
| *C07C 57/46* | (2006.01) |
| *C07C 57/48* | (2006.01) |
| *C07C 59/54* | (2006.01) |
| *C07C 59/84* | (2006.01) |
| *C07C 62/20* | (2006.01) |
| *C07C 229/18* | (2006.01) |
| *C07C 229/42* | (2006.01) |
| *C07C 323/52* | (2006.01) |

(52) U.S. Cl.
CPC ............. *A61K 31/192* (2013.01); *A61K 31/196* (2013.01); *A61K 31/22* (2013.01); *A61K 31/513* (2013.01); *A61K 31/675* (2013.01); *A61K 31/7068* (2013.01); *C07C 57/46* (2013.01); *C07C 57/48* (2013.01); *C07C 59/54* (2013.01); *C07C 59/84* (2013.01); *C07C 62/20* (2013.01); *C07C 229/18* (2013.01); *C07C 229/42* (2013.01); *C07C 323/52* (2013.01)

(58) Field of Classification Search
None
See application file for complete search history.

(56) References Cited

FOREIGN PATENT DOCUMENTS

| EP | 0 268 907 A2 | 6/1988 |
|---|---|---|
| WO | WO 03/043625 A1 | 5/2003 |
| WO | WO 2008/026125 A2 | 3/2008 |
| WO | WO 2009/055932 A1 | 5/2009 |
| WO | WO 2009/055933 A1 | 5/2009 |
| WO | WO 2009/076761 A1 | 6/2009 |
| WO | WO 2010/127440 A1 | 11/2010 |
| WO | WO 2010/127448 A1 | 11/2010 |

*Primary Examiner* — Patrick Lewis
(74) *Attorney, Agent, or Firm* — Saliwanchik, LLoyd & Eisenschenk

(57) ABSTRACT

New uses for phenylketone carboxylate compounds and substituted aromatic compounds of Formula I, Formula I.1, Formula I.2, Formula IA, Formula IB, Formula IC and Formula II and their pharmaceutical acceptable salts for the treatment of cancer. The use of a combination of two of these compounds is described and the use of the combination of one of these compounds with an anticancer agent such as decarbazine, doxorubicin, daunorubicin, cyclophosphamide, busulfex, busulfan, vinblastine, vincristine, bleomycin, etoposide, topotecan, irinotecan, taxotere, taxol, 5-fluorouracil, methotrexate, gemcitabine, cisplatin, carboplatin and chlorambucil.

19 Claims, 12 Drawing Sheets

COMPOUNDS AND COMPOSITIONS FOR THE TREATMENT OF CANCER

CROSS REFERENCE TO A RELATED APPLICATION

This application is a National Stage Application of International Application Number PCT/CA2011/001179, filed Oct. 26, 2011; which claims priority to U.S. Provisional Application No. 61/407,069, filed Oct. 27, 2010; both of which are incorporated herein by reference in their entirety.

FIELD OF INVENTION

The present invention relates to the field of medicine. More particularly, the invention relates to compounds, pharmaceutical compositions and uses thereof for the treatment of cancers.

BACKGROUND OF INVENTION

Cancer refers to more than one hundred clinically distinct forms of the disease. Almost every tissue of the body can give rise to cancer and some can even yield several types of cancer. Cancer is characterized by an abnormal growth of cells which can invade the tissue of origin or spread to other sites. In fact, the seriousness of a particular cancer, or the degree of malignancy, is based upon the propensity of cancer cells for invasion and the ability to spread. That is, various human cancers (e.g., carcinomas) differ appreciably as to their ability to spread from a primary site or tumor and metastasize throughout the body. Indeed, it is the process of tumor metastasis which is detrimental to the survival of the cancer patient. A surgeon can remove a primary tumor, but a cancer that has metastasized often reaches too many places to permit a surgical cure. To successfully metastasize, cancer cells must detach from their original location, invade a blood or lymphatic vessel, travel in the circulation to a new site, and establish a tumor.

The twelve major cancers are prostate, breast, lung, colorectal, bladder, non-Hodgkin's lymphoma, uterine, melanoma, kidney, leukemia, ovarian, and pancreatic cancers. Often, cancers may be more or less effectively treated with chemotherapeutic agents (also referred to as cytotoxic drugs). However, chemotherapeutic agents suffer from two major limitations. First, chemotherapeutic agents are not specific for cancer cells and particularly at high doses, they are toxic to normal rapidly dividing cells. Second, with time and repeated use cancer cells develop resistance to chemotherapeutic agents thereby providing no further benefit to the patient. Subsequently, other treatment modalities have been investigated to address the limitations imposed by the use of chemotherapeutic agents. Alternative, well-studied treatment options are surgery, radiation and immunotherapy. However, these treatments also have serious limitations especially in more advanced cancers. Thus, for example, surgery is limited by the ability to completely remove extensive metastases, radiation is limited by the ability to selectively deliver radiation and penetrate cancer cells and immunotherapy (e.g., use of approved cytokines) is limited by the balance between efficacy and toxicity. For this reason, other relatively newer therapeutic approaches are under study. These approaches include the use of protein kinase inhibitors (not selective and therefore toxic and still prone to drug resistance), antiangiogenesis agents (limited efficacy and toxicity) and gene therapy (no significant success to date). Therefore, a need still exists for novel compounds which are efficacious (e.g., reduce tumor size and/or spread of metastases) and have reduced toxicity for the treatment of cancer.

The present invention addresses the need for compounds, pharmaceutical compositions and treatment methods for the treatment of cancers. Additional features of the invention will be apparent from a review of the disclosure, figures and description of the invention herein.

BRIEF SUMMARY OF THE INVENTION

The present invention relates to the use of compounds and compositions thereof for the treatment of various cancers, including but not limited to bladder, breast, colorectal, kidney, melanoma, non-Hodgkin's lymphoma, leukemia, ovarian, pancreatic, prostate and uterine cancers.

A particular aspect of the invention relates to a method for treating cancer in a subject in need thereof which comprises administering to the subject of a therapeutically effective amount of a substituted aromatic compound represented by Formula I, Formula I.1, Formula I.2, Formula IA, Formula IB, Formula IC or Formula II, or a pharmaceutically acceptable salt thereof, as defined hereinafter.

Particular aspects of the invention relates to the pharmaceutical use of compounds according to Formula I, Formula I.1, Formula I.2, Formula IA, Formula IB, Formula IC or Formula II, as defined herein, and pharmaceutically acceptable salts thereof. The pharmaceutically acceptable salt of the compounds according to the invention is preferably a base addition salt. The base addition salt comprises a metal counterion that is preferably sodium, potassium, calcium, magnesium or lithium. In preferred embodiment, the preferred metal counterion is sodium.

Another related aspect of the invention relates to pharmaceutical compositions comprising compounds of Formula I, Formula I.1, Formula I.2, Formula IA, Formula IB, Formula IC or Formula II as defined for use in treatment of cancer in a subject in need thereof, and to the use of a compound represented by Formula I, Formula I.1, Formula I.2, Formula IA, Formula IB, Formula IC or Formula II for treatment of cancer in a subject in need thereof, or for the manufacture of a medicament for treatment of cancer in a subject in need thereof. One particular example is an anticancer composition comprising a compound represented by Formula I, Formula I.1, Formula I.2, Formula IA, Formula IB, Formula IC or Formula II as defined herein, and a pharmaceutically acceptable carrier. Another particular example is an anticancer composition comprising a compound as defined in Table 1, and more preferably, an anticancer composition comprising Compound I, II, XV, XVII and/or XIX.

Another aspect of the invention relates to a pharmaceutical composition comprising a compound represented by Formula I, Formula I.1, Formula I.2, Formula IA, Formula IB, Formula IC or Formula II as defined herein, that further comprises an anticancer agent where the anticancer agent may be decarbazine, doxorubicin, daunorubicin, cyclophosphamide, busulfex, busulfan, vinblastine, vincristine, bleomycin, etoposide, topotecan, irinotecan, taxotere, taxol, 5-fluorouracil, methotrexate, gemcitabine, cisplatin, carboplatin or chlorambucil.

A related aspect concerns a method for treating bladder, breast, colorectal, kidney, melanoma, non-Hodgkin's lymphoma, leukemia, ovarian, pancreatic, prostate and/or uterine cancer in a human patient, comprising administering to the patient a therapeutically effective amount of a pharmaceutical composition as defined herein. Another related aspect concerns a method for treating breast, colorectal, leukemia, melanoma and/or pancreatic cancer in a human patient, comprising administering to the patient a therapeutically effective amount of a pharmaceutical composition as defined herein.

The invention also relates to treatment methods wherein the compounds of the invention exhibits one or more of the following biological activities in a subject: stimulating and/or enhancing IL-12 production under inflammatory conditions; stimulating cytolytic activity of lymphocytes; stimulating antitumor activity of NK cells; inducing regression of established tumors and/or of primary solid tumors; inhibiting TGF-induced CTGF production; inhibiting CTGF-mediated activities.

The invention further relates to compounds according to Formula I, Formula I.1, Formula I.2, Formula IA, Formula IB, Formula IC or Formula II as defined herein and pharmaceutically acceptable salts thereof, as prophylactically effective and/or therapeutically effective agents against various cancers in subjects.

Further aspects of the invention will be apparent to a person skilled in the art from the following description, claims, and generalizations herein.

DETAILED DESCRIPTION OF THE INVENTION

Figure 1:
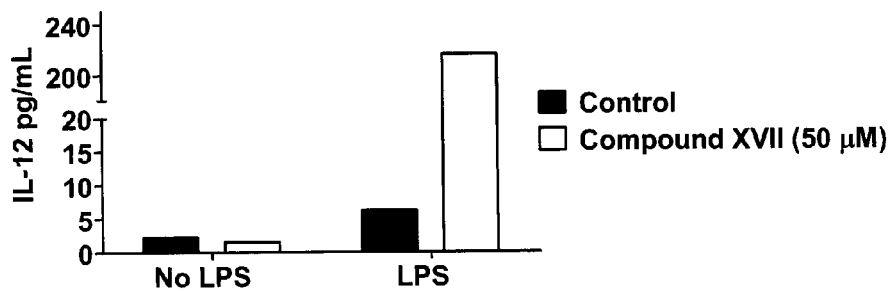
FIG. 1 is a bar graph showing the effects of Compound XVII on IL-12 production in vitro (RAW.264 cells) under non-inflammatory and inflammatory conditions.

The present discloses compounds of Formula I, Formula I.1, Formula I.2, Formula IA, Formula IB, Formula IC and Formula II and compositions comprising same for use in the treatment of cancers. Some compounds according to the invention may be broadly classified as substituted phenyl (phenoxy, thiophenoxy, anilino) benzoic, acetic or propionic acids.

A) Compounds of the Invention

According to one aspect, the invention concerns the pharmaceutical uses for treatment of cancer of compounds represented by Formula I, or pharmaceutically acceptable salts thereof:

Cy-Q                                   Formula I wherein:
Cy is

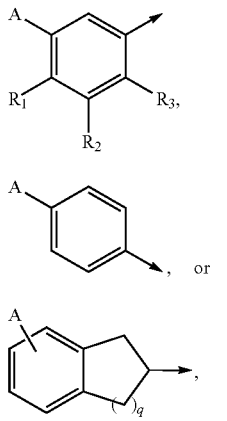

wherein
→ represents a covalent bond connecting Cy to Q;
q is 1, 2, or 3;
A is
  1) $C_1$-$C_8$ alkyl,
  2) $C_2$-$C_6$ alkenyl,
  3) $C_1$-$C_7$ alkyl-Y—,
  4) $C_1$-$C_7$ alkyl-OC(O)—,
  5) phenyl-O-phenyl-$CH_2$—Y, or
  6) $C_1$-$C_7$ alkyl-CH(OH)—;
$R_1$, $R_2$ and $R_3$ are independently selected from H, F, Cl, or OH;
when Cy is Cy1 and Cy2, then Q is
  1) C(O)OH,
  2) $C(CH_3)_2$C(O)OH,
  3) $(CH_2)_m$—C(O)OH,
  4) ZCH(C(O)OH)$C_1$-$C_8$ alkyl,
  5) Z$(CH_2)_m$C(O)OH,
  6) CH($R^c$)C(O)OH,
  7) CH(phenyl)$CH_2$C(O)OH,
  8) CH($R^c$)$CH_2$C(O)OH, or
  9) $CH_2$CH(C(O)OH)$C_1$-$C_8$ alkyl,
wherein
m is 1 or 2;
the phenyl is substituted by an $R^d$ substituent;
Y is O, S, $NR^aR^b$, or C(O);
Z is O, S, or $NR^aR^b$;
when Cy is Cy3, then Q is C(O)OH;
$R^a$ and $R^b$ are independently selected from
  1) H, or
  2) $C_1$-$C_3$ alkyl;
$R^c$ is
  1) H,
  2) $C_1$-$C_4$ alkyl,
  3) $C_2$-$C_4$ alkenyl, or
  4) $C_2$-$C_4$ alkynyl;
$R^d$ is
  1) $OR^e$,
  2) halogen,
  3) $CF_3$, or
  4) phenyl; and
$R^e$ is
  1) H, or
  2) $C_1$-$C_4$ alkyl.

According to another aspect, the invention concerns the pharmaceutical uses for treatment of cancer of compounds represented by Formula I.1, or pharmaceutically acceptable salts thereof:

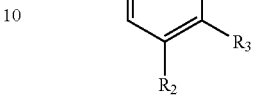

Formula I.1 wherein
A is
  1) $C_1$-$C_8$ alkyl, or
  2) $C_2$-$C_6$ alkenyl,
$R_2$ and $R_3$ are independently selected from H, F, Cl, or OH;
Q is
  1) C(O)OH,
  2) $C(CH_3)_2$C(O)OH,
  3) $(CH_2)_m$—C(O)OH, or
  4) CH($R^c$)C(O)OH,
wherein m is 1; and
$R^c$ is $C_1$-$C_4$ alkyl.

According to another aspect, the invention concerns the pharmaceutical uses for treatment of cancer of compounds represented by Formula IA, or pharmaceutically acceptable salts thereof:

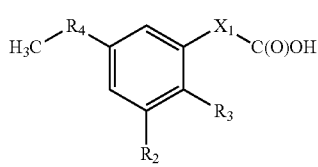

Formula IA wherein
$R_2$ and $R_3$ are independently selected from H, OH, F or Cl;
$X_1$ is CH($CH_3$), C($CH_3$)$_2$, or $(CH_2)_n$, wherein n is 0, 1 or 2; and
$R_4$ is $(CH_2)_{m1}$, $(CH_2)_{q1}$CH=CH, or CH=CH($CH_2$) wherein m1 is 3, 4, 5 or 6 and q1 is 1, 2, or 3.

According to another aspect, the invention concerns the pharmaceutical uses for treatment of cancer of compounds represented by Formula I.2, or pharmaceutically acceptable salts thereof:

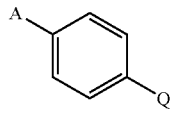

Formula I.2 wherein
Y is O, S, or $NR^aR^b$;
A is
  1) $C_1$-$C_8$ alkyl,
  2) $C_2$-$C_6$ alkenyl,
  3) $C_1$-$C_7$ alkyl-Y—, or
  4) phenyl-O-phenyl-$CH_2$—Y;

Q is
1) CH(phenyl)CH$_2$C(O)OH, or
2) CH(R$^c$)CH$_2$C(O)OH,
wherein the phenyl is substituted by an R$^d$ substituent;
R$^a$ and R$^b$ are independently selected from
1) H, or
2) C$_1$-C$_3$ alkyl;
R$^c$ is
1) H,
2) C$_1$-C$_4$ alkyl,
3) C$_2$-C$_4$ alkenyl, or
4) C$_2$-C$_4$ alkynyl;
R$^d$ is
1) OR$^e$,
2) halogen,
3) CF$_3$, or
4) phenyl; and
R$^e$ is
1) H, or
2) C$_1$-C$_4$ alkyl.

According to another aspect, the invention concerns the pharmaceutical uses for treatment of cancer of compounds represented by Formula IB, or pharmaceutically acceptable salts thereof:

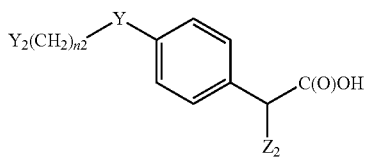

Formula IB wherein
n2 is 0, 1 or 2;
Y is O, NH, NC$_1$-C$_3$ alkyl, or S;
Y$_2$ is CH$_3$ or phenyl substituted by R$_d$;
Z$_2$ is H, C$_1$-C$_4$ alkyl, C$_2$-C$_4$ alkenyl, C$_2$-C$_4$ alkynyl or

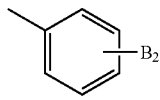

when Y$_2$ is

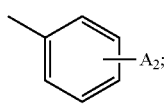

or
Z$_2$ is

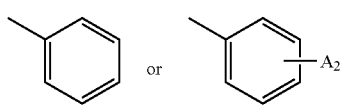

when Y$_2$ is a branched or straight chain C$_1$-C$_4$ alkyl; or
Z$_2$ is

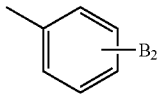

when Y$_2$ is CH$_3$;
R$_d$ is OH, F, Cl, Br, CF$_3$, OC$_1$-C$_4$ alkyl or phenyl;
A$_2$ is OH, F, Cl, Br, CF$_3$, phenyl, or OC$_1$-C$_4$ alkyl; and
B$_2$ is F, Cl, Br, CF$_3$ or phenyl.

According to another aspect, the invention concerns the pharmaceutical uses in the treatment of cancers of compounds represented by Formula IC, or pharmaceutically acceptable salts thereof:

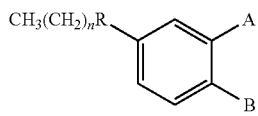

Formula IC wherein
n is 2, 3, 4, 5, or 6;
R is —C(O)—, —OC(O)—, —CH(OH)—, NH, NC$_1$-C$_3$ alkyl, O, S, or CH$_2$;
A is (CH$_2$)$_m$C(O)OH, W(CH$_2$)$_m$C(O)OH, or YCH(C(O)OH)(CH$_2$)$_p$CH$_3$ when B is H;
B is (CH$_2$)$_m$C(O)OH, W(CH$_2$)$_m$C(O)OH or YCH(C(O)OH)(CH$_2$)$_p$CH$_3$ when A is H; or
A and B are covalently bonded to form a 5-, 6-, or 7-membered cycloalkyl substituted with a C(O)OH group;
W is O, S, or NH;
Y is O, S, NH or CH$_2$;
m is 0, 1, or 2; and
p is 1, 2, 3, 4, 5, 6, or 7.

As used herein, the term "alkyl" is intended to include both branched and straight chain saturated aliphatic hydrocarbon groups having the specified number of carbon atoms, for example, C$_1$-C$_8$ as in C$_1$-C$_8$ alkyl is defined as including groups having 1, 2, 3, 4, 5, 6, 7 or 8; C$_1$-C$_7$ as in C$_1$-C$_7$ alkyl is defined as including groups having 1, 2, 3, 4, 5, 6, or 7; C$_1$-C$_6$ as in C$_1$-C$_6$ alkyl is defined as including groups having 1, 2, 3, 4, 5, or 6, carbons in a linear or branched arrangement; for example, C$_1$-C$_4$ as in C$_1$-C$_4$ alkyl is defined as including groups having 1, 2, 3, or 4 carbon atoms in a linear or branched arrangement; or C$_1$-C$_3$ as in C$_1$-C$_3$ alkyl is defined as including groups having 1, 2, or 3. Examples of alkyl defined above include, but are not limited to, methyl, ethyl, n-propyl, i-propyl, n-butyl, t-butyl, i-butyl, pentyl, hexyl, heptyl and octyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regiochemistry and combinations thereof. For example, C$_2$-C$_6$ as in C$_2$-C$_6$ alkenyl is defined as including groups having 2, 3, 4, 5, or 6 carbons in a linear or branched arrangement, at least two of the carbon atoms being bonded together by a double bond, or C$_2$-C$_4$ as in C$_2$-C$_4$ alkenyl is defined as including groups having 2, 3, or 4 carbons in a linear or branched arrangement, at least two of the carbon atoms being bonded together by a double bond. Examples of alkenyl include ethenyl (vinyl), 1-propenyl, 2-propenyl, and 1-butenyl.

As used herein, the term "alkynyl" is intended to mean unsaturated, straight chain hydrocarbon groups having the specified number of carbon atoms therein and in which at least two carbon atoms are bonded together by a triple bond. For example $C_2$-$C_4$ as in $C_2$-$C_4$ alkynyl is defined as including groups having 2, 3, or 4 carbon atoms in a chain, at least two of the carbon atoms being bonded together by a triple bond. Examples of such alkynyls include ethynyl, 1-propynyl, 2-propynyl and the like.

As used herein, the term "halogen" is intended to mean fluorine, chlorine, or bromine.

Examples of compounds of Formula I include, but are not limited to, the Compounds I to XLI listed in Table 1 hereinafter. Specific examples of compounds of Formula IA include, but are not limited to, Compounds I to XIII. Specific examples of compounds of Formula IB include, but are not limited to, Compounds XIV to XVI. Specific examples of compounds of Formula IC include, but are not limited to, Compounds XVII to XLI.

TABLE 1

Examples of compounds of Formula I

| | Structure |
|---|---|
| Compound I | [structure] |
| Compound II | [structure] |
| Compound III | [structure] |
| Compound IV | [structure] |
| Compound V | [structure] |
| Compound VI | [structure] |
| Compound VII | [structure] |
| Compound VIII | [structure] |
| Compound IX | [structure] |
| Compound X | [structure] |

TABLE 1-continued

Examples of compounds of Formula I

| | Structure |
|---|---|
| Compound XI | sodium 4-pentylbenzoate |
| Compound XII | sodium 4-hexylbenzoate |
| Compound XIII | sodium 3-hexylbenzoate |
| Compound XIV | sodium 3-(4-((3-phenoxybenzyl)oxy)phenyl)pent-4-ynoate |
| Compound XV | sodium 3-(4-((3-phenoxybenzyl)amino)phenyl)propanoate |
| Compound XVI | sodium 3-(4-butoxyphenyl)-3-(3-fluorophenyl)propanoate |
| Compound XVII | sodium 2-(4-octanoylphenoxy)decanoate |
| Compound XVIII | sodium 3-octanoylbenzoate |

TABLE 1-continued
Examples of compounds of Formula I
Structure
Compound XIX 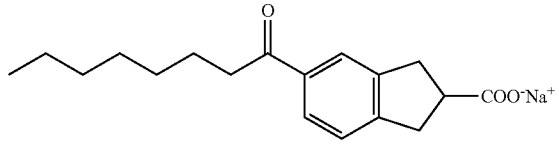
Compound XX 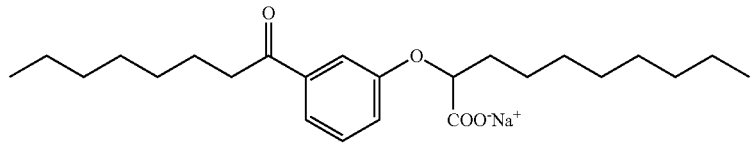
Compound XXI 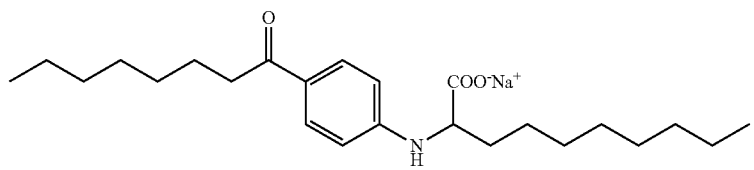
Compound XXII 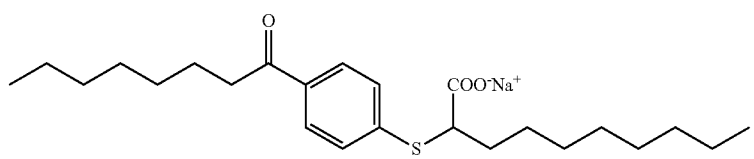
Compound XXIII 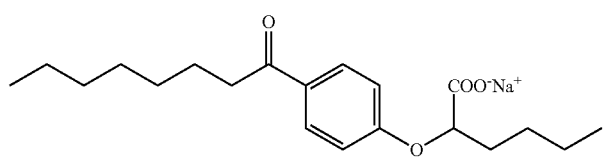
Compound XXIV 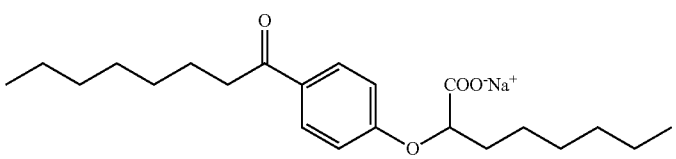
Compound XXV 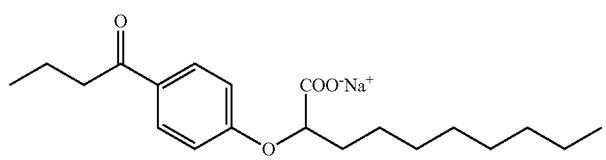
Compound XXVI 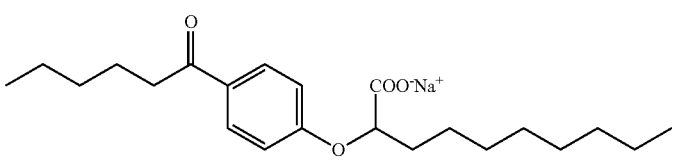
Compound XXVII 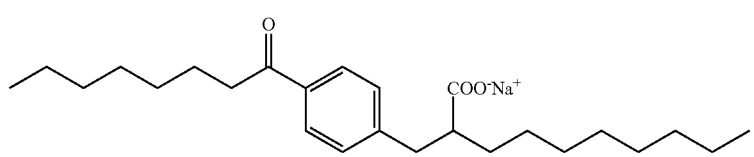
Compound XXVIII 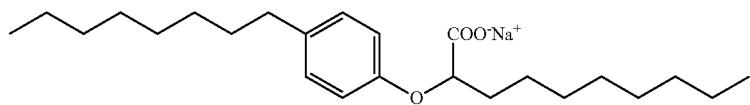

TABLE 1-continued

Examples of compounds of Formula I

Structure

Compound XXIX

Compound XXX

Compound XXXI

Compound XXXII

Compound XXXIII

Compound XXXIV

Compound XXXV

Compound XXXVI

Compound XXXVII

Compound XXVIII

Compound XXXIX

TABLE 1-continued

Examples of compounds of Formula I

Structure

Compound XL

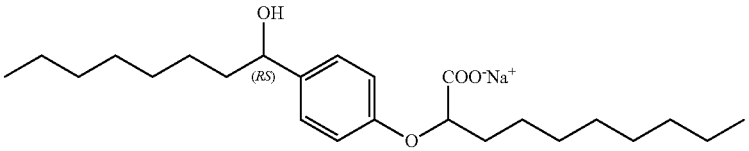

Compound XLI

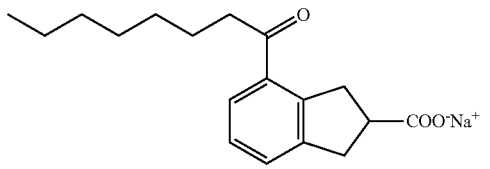

The Applicants have described elsewhere compounds whose structure is related to the structure of some of the compounds of the present invention. Reference is made for instance to the compounds disclosed in Table 2 of international PCT application No. PCT/CA2010/000677 filed on May 3, 2010 entitled "Substituted aromatic compounds and pharmaceutical uses thereof" which is incorporated herein by reference in its entirety. Accordingly, in particular embodiments any one or all the Compounds I to XV and XVIII disclosed in Table 2 of PCT/CA2010/000677 is excluded from the scope of the present invention. In another particular embodiment, the use for the treatment of kidney cancer and/or for the treatment of renal cell carcinoma of any one or all the Compounds I to XIII disclosed in Table 1 of the instant application is excluded from the scope of the present invention. Similarly, in particular embodiments, the uses of compounds of Formula I, Formula I.1, Formula I.2, Formula IA, Formula IB, and/or compounds of Formula IC for the treatment of kidney cancer and/or for the treatment of renal cell carcinoma, are excluded from the scope of the present invention.

In addition to the compounds described by Formula I, Formula I.1, Formula I.2, Formula IA, Formula IB, and Formula IC hereinabove, an additional aspect of the invention concerns the use of pharmaceutically acceptable salts of a compound of Formula II:

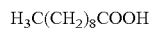   Formula II

In preferred embodiments the compound of Formula II is a metal decanoate salt represented by Formula IIA:

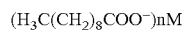   Formula IIA wherein n=1 when M is Na$^+$ or K$^+$ and n=2 when M is Ca$^{++}$ or Mg$^{++}$.

Specific examples of pharmaceutically acceptable metal decanoate salts according to the invention include, but are not limited to: $H_3C(CH_2)_8COO^-Na^+$; $H_3C(CH_2)_8COO^-K^+$; $(H_3C(CH_2)_8COO^-)_2Ca^{++}$ and $(H_3C(CH_2)_8COO^-)_2 Mg^{++}$.

In particular embodiments, the use of compounds of Formula II or IIA for the treatment of pancreatic cancer is excluded from the scope of the invention. In particular embodiments, compounds of Formula II or IIA (e.g., $H_3C(CH_2)_8COO^-Na^+$) are solely for use in cancer monotherapy. In particular embodiments, the use of compounds Formula II or IIA (e.g., $H_3C(CH_2)_8COO^-Na^+$) in combination with another chemotherapeutic agent (e.g., gemcitabine) is excluded from the scope of the invention. In particular embodiments, the use of sodium decanoate ($H_3C(CH_2)_8COO^-Na^+$) for the treatment of pancreatic cancer is excluded from the scope of the invention.

Salts

As used herein, the term "pharmaceutically acceptable salt" is intended to mean base addition salts. Example of pharmaceutically acceptable salts are also described, for example, in Berge et al., "Pharmaceutical Salts", *J. Pharm. Sci.* 66, 1-19 (1977). Pharmaceutically acceptable salts may be synthesized from the parent agent that contains an acidic moiety, by conventional chemical methods. Generally, such salts are prepared by reacting the free acid forms of these agents with a stoichiometric amount of the appropriate base in water or in an organic solvent, or in a mixture of the two. Salts may be prepared in situ, during the final isolation or purification of the agent or by separately reacting a purified compound of the invention in its free acid form with the desired corresponding base, and isolating the salt thus formed.

In an embodiment, the pharmaceutically acceptable salt of the compounds of Formula I, Formula I.1, Formula I.2, Formula IA, Formula IB, Formula IC and Formula II is a base addition salt of sodium, potassium, calcium, magnesium or lithium. In preferred embodiment, the base addition salt is sodium. In some embodiments, the compounds are the sodium salts listed in Table I hereinbefore. Preferably the compound is selected from Compounds I, II, VIII, XIII, XV, XVII, XVIII, XIX and XX as defined herein. More preferably, the compounds are Compounds I, II, XV, XVII and XIX as defined herein.

All acid, salt and other ionic and non-ionic forms of the compounds described are included as compounds of the invention. For example, if a compound is shown as an acid herein, the salt forms of the compound are also included. Likewise, if a compound is shown as a salt and the acid forms are also included.

Prodrugs

In certain embodiments, the compounds of the present invention as represented by generalized Formula I, Formula I.1, Formula I.2, Formula IA, Formula IB, Formula IC and Formula II, wherein said compounds are present in the free carboxylic acid form, may also include all pharmaceutically acceptable salts, isosteric equivalents such as tetrazole and prodrug forms thereof. Examples of the latter include the pharmaceutically acceptable esters or amides obtained upon reaction of alcohols or amines, including amino acids, with the free acids defined by Formula I, Formula I.1, Formula I.2, Formula IA, Formula IB, Formula IC and Formula II.

Chirality

The compounds of the present invention, their pharmaceutically acceptable salts, or prodrugs thereof, may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist in Zwitterionic form and the present invention includes Zwitterionic forms of these compounds and mixtures thereof.

Hydrates

In addition, the compounds of the invention also may exist in hydrated and anhydrous forms. Hydrates of any of the formulas described herein are included as compounds of the invention which may exist as a monohydrate or in the form of a polyhydrate.

B) Methods of Preparation

In general, all compounds of the present invention may be prepared by any conventional methods, using readily available and/or conventionally preparable starting materials, reagents and conventional synthesis procedures. Of particular interest is the work of Hundertmark, T.; Littke, A. F.; Buchwald, S. L.; Fu, G. C. *Org. Lett.* 12, 1729-1731 (2000).

The exemplification section hereinafter provides general schemes and specific, but non limitative, examples for the synthesis of Compounds I, II, IV, V, VII, VIII, X, XI, XIV, XV, XVI, XVII, XVIII, XIX and XX.

C) Pharmaceutical Applications

As indicated and exemplified herein, the compounds of the present invention have beneficial pharmaceutical properties and these compounds may have useful pharmaceutical applications in subjects. Medical and pharmaceutical applications contemplated by the inventors include, but are not limited to, prevention and/or treatment of various cancers. In one embodiment the cancer is selected from bladder, breast, colorectal, kidney, melanoma, non-Hodgkin's lymphoma, leukemia, ovarian, pancreatic, prostate and uterine cancers. In another embodiment, the cancer is selected from breast, colorectal, leukemia, melanoma and pancreatic cancers.

The term "subject" includes living organisms in which cancers can occur, or which are susceptible to such disease. The term "subject" includes animals such as mammals or birds. Preferably, the subject is a mammal. More preferably, the subject is a human. Most preferably, the subject is a human patient in need of treatment.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms "treatment" or "treating" of a subject includes the application or administration of a compound of the invention to a subject (or application or administration of a compound of the invention to a cell or tissue from a subject) with the purpose of delaying, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. In some embodiments, the term "treating" can include increasing a subject's life expectancy and/or delay before additional treatments are required (e.g., dialysis or kidney transplantation for a patient having kidney cancer).

Reference herein to treatment extends to prophylaxis as well as therapy of an established cancer. Accordingly, the compounds of the present invention could be used after surgical removal of the primary tumor, prior to surgery, prior or after aggressive chemotherapy or even when the patient is in remission. The compounds of the invention are expected to have a relative lack of toxicity when compared to standard cancer therapies thereby allowing for a more liberal prophylactic use than would be advisable with standard therapies.

Furthermore, in one embodiment the compounds of the invention are for used monotherapy for the treatment of cancer. In other embodiments, the compounds of the invention is used in combination with already approved anticancer agents such as chemotherapeutic agents, cytokines, radiation therapy agents, etc. Examples of anticancer agents which may be used in combination with the compounds of the present invention include, but are not limited to, decarbazine, doxorubicin, daunorubicin, cyclophosphamide, busulfex, busulfan, vinblastine, vincristine, bleomycin, etoposide, topotecan, irinotecan, taxotere, taxol, 5-fluorouracil, methotrexate, gemcitabine, cisplatin, carboplatin and chlorambucil.

Accordingly, method of treatment according to the present invention may also include co-administration of the at least one compound according to the invention, or a pharmaceutically acceptable salt thereof together with the administration of another therapeutically effective agent. Therefore, an additional aspect of the invention relates to methods of concomitant therapeutic treatment of a subject, comprising administering to a subject in need thereof an effective amount of a first agent and a second agent, wherein the first agent is as defined in Formula I, Formula I.1, Formula I.2, Formula IA, Formula IB, Formula IC or Formula II, and the second agent is for the prevention or treatment of any one of disorder or disease as defined hereinbefore. As used herein, the term "concomitant" or "concomitantly" as in the phrases "concomitant therapeutic treatment" or "concomitantly with" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g., a human).

Accordingly, the invention also relates to a method for preventing, reducing or eliminating a symptom or complication of any one of the above mentioned diseases or conditions. The method comprises administering, to a subject in need thereof, a first pharmaceutical composition comprising at least one compound of the invention and a second pharmaceutical composition comprising one or more additional active ingredients, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes. Preferably the first agent is a compound of Formula I or Formula II as defined herein, or a pharmaceutically acceptable salt thereof, e.g., sodium salt. The second agent may be selected from the list of compounds given hereinbefore.

IL-12 and Inflammation

It is well known to the art that chronic inflammation promotes the development of cancer and that the two processes occur together, often as a result of the activation of the transcription factor NFκB pathway; see for example M. Philip et al. in *Seminars in Cancer Biology* 14, 433-439 (2004). Compounds described in this invention increase IL-12 under an inflammatory process such as cancer. This was demonstrated by an enhancement of the production of IL-12 in the LPS-treated macrophage cell line (RAW264.7). IL-12 is a key regulator of T helper (Th1/Th2) balance, which is critically skewed, one way or the other, in several infections, autoimmunity, atopy and tumors; I. J. Elenkov et al. in *Ann. NY Acad. Sci.* 917, 94-105 (2000). Low levels of IL-12 have been associated with tumor growth, as opposed to tumor regression observed with administration of IL-12 delivered in situ or systemically; M. P. Colombo et al. in *Cancer Res.* 56, 2531-2534 (1996). Furthermore, IL-12 can augment the cytolytic activity of lymphocytes from patients with cancer; R. J. Soiffer et al. in *Blood* 82, 2790-2796 (1993) and the antitumor activity of NK cells. IL-12 has been shown to have potent antitumor effects in murine models of melanoma, sarcoma, kidney, ovarian, renal, lung, colon and breast; M. J. Robertson et al. in *The Oncologist* 1, 88-97 (1996). Current data indicates that CD4 T cells, CD8 T cells, NK cells and interferon γ (IFN-γ) may contribute to the antitumor effects of IL-12 therapy. The results of preclinical studies suggest several potential strategies for the use of IL-12 in cancer therapy. IL-12 can induce the regression of established, bulky murine tumors, but in most preclinical models, IL-12 is more effective in animals with a smaller tumor burden. Thus, although the safety of IL-12 therapy must be confirmed involving patients with advanced cancer, IL-12 may prove more efficacious in the context of minimal residual disease. Patients at high risk for disease recurrence after surgical resection of primary solid tumors or patients with malignancies in complete remission after induction chemotherapy or patients with minimal residual disease after autologous and allogenic peripheral blood stem cell transplantation may be appropriate candidates for treatment with IL-12. It can also be used as an immunoadjuvant. However, administration of systemic IL-12 demonstrated dose-limiting toxicity. Compounds of this invention, which enhance the production of IL-12 in localized inflammatory processes such as tumors, possess an important advantage over systemic administration of IL-12, by limiting the toxicity concomitant with the use of IL-12.

In some embodiment, the compounds and compositions of the invention are useful for: (i) stimulating and/or enhancing IL-12 production under inflammatory conditions, such as cancer; (ii) stimulating cytolytic antitumor activity of lymphocytes and/or NK cells; and/or (iii) inducing regression of established tumors and/or primary solid tumors.

CTGF and Progression of Cancers

Connective Tissue Growth Factor (CTGF) is a valuable target for therapeutic intervention in cancer. CTGF is a member of the CCN family of secreted, matrix-associated proteins encoded by immediate early genes. CTGF plays various roles in angiogenesis and tumor growth. CTGF expression has been shown to be associated with tumor development and progression. For example, the level of CTGF expression is positively correlated with bone metastasis in breast cancer; Y. Kang et al. in *Cancer Cell*. 3, 537-549 (2003), glioblastoma growth; L. H. Pan et al. in *Neurol. Res.* 24, 677-6583 (2002), poor prognosis in esophageal adenocarcinoma; A. Koliopanos et al. in *World J. Surg.* 26, 420-427 (2002), aggressive behavior of pancreatic cancer cells; C. Wenger et al. in *Oncogene* 18, 1073-1080 (1999) and invasive melanoma; M. Jubo et al. in *Br. J. Dermatol.* 139, 192-197 (1998). CTGF is believed to be a multifunctional signaling modulator involved in a wide variety of biologic or pathologic processes, such as angiogenesis, osteogenesis, renal disease, skin disorders, and tumor development, There are at least 21 different human tumors or cancers that express CTGF expression, signifying its influence on the biology and progression of cancer. Of particular interest is the fact that CTGF is expressed in human tumor cells or surrounding stromal cells, including acute lymphoblastic leukemia, breast cancer cells, cervical cancer, cervical cancer, chondrosarcoma, cutaneous fibrohistiocytic and vascular tumors, esophageal cancer, gastric cancer, glioblastoma and gliomas, hepatocellular carcinomas, laryngeal squamous cell carcinoma, non-small-cell lung cancer, melanoma, myofibroblastic tumors, oral SSC, ovarian cancer, pancreatic cancer, prostate cancer, thabdomyosarcoma, and Wilms tumor; C.-Y. Chu et al. in *J. Biomed. Sci* 15, 675-685 (2008).

As shown hereinafter in the examples, the compounds of the invention are capable inhibiting TGF-induced CTGF production in NHDF. These results suggest an ability of the compounds of the present invention to exert an antitumor effect via the inhibition of production and expression of CTGF. Therefore, the compounds of the invention may offer a potential multi-pronged attack on tumor growth and metastasis through inhibition of CTGF-mediated activities.

Accordingly, in some embodiment, the compounds and compositions of the invention are useful for: (i) inhibiting TGF-induced CTGF production; (ii) inhibiting of CTGF-mediated activities in subjects, including but not limited to inhibiting angiogenesis, and inhibiting epithelial to mesenchymal transition (EMT); and/or (iii) inhibiting tumor cell migration and subsequent initiation and establishment of secondary tumors or metastasis.

Additional aspects of the present invention relates to drugs with a novel mechanism of anticancer activity, for instance induction of interleukin-12 (IL-12) and/or inhibition of connective tissue growth factor (CTGF). The compounds/drugs of the invention exhibit reduced toxicity for the treatment of cancers as exemplified hereinafter. The invention also encompasses method of treatment where a practitioner makes a judicious choice of compounds and combination of compounds having appropriate anticancer activity(ies) that is (are) selected to be either distinct from the mechanism of action of standard currently commercialized chemotherapeutic agents or to provide a synergic activity when used in combination with standard chemotherapeutic agents. With such methods it becomes possible to provide novel, more durable (e.g., less susceptible to drug resistance), less toxic therapy for the treatment of certain cancers. Furthermore, endogenous enhancement of IL-12 and/or inhibition of CTGF is not deleterious to normal cellular function and so cancer therapy with the compounds of the invention is expected to be relatively non-toxic, especially in comparison with standard chemotherapeutic agents.

D) Pharmaceutical Compositions and Formulations

A related aspect of the invention concerns pharmaceutical compositions comprising a therapeutically effective amount one or more of the compounds of the invention described herein (e.g., a compound of Formula I, Formula I.1, Formula I.2, Formula IA, Formula IB, Formula IC and Formula II). As indicated hereinbefore, the pharmaceutical compositions of the invention may be useful in prevention and/or treatment of various cancers; in stimulating and/or enhancing IL-12 production under inflammatory conditions, such as cancer; in stimulating cytolytic antitumor activity of lymphocytes and/or NK cells; in inducing regression of established tumors and/or primary solid tumors; and/or in inhibiting TGF-induced CTGF production and subsequent inhibition of CTGF-mediated activities in subjects.

As used herein, the term "therapeutically effective amount" means the amount of compound that, when administered to a subject for treating or preventing a particular disorder, disease or condition, is sufficient to effect such treatment or prevention of that disorder, disease or condition. As used herein, the term "therapeutically effective amount" further means the amount of compound that stimulates and/or enhancing IL-12 production under inflammatory conditions, such as cancer; stimulates cytolytic antitumor activity of lymphocytes and/or NK cells; induces regression of established tumors and/or primary solid tumors; inhibits TGF-induced CTGF production; and/or inhibits CTGF-mediated activities in subjects. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject (e.g., total or partial response as evidenced by factors which include reduction in tumor burden and/or tumor size as well as increase in survival time and/or quality of life which is associated with a reduction in amount and/or duration of treatment with standard but more toxic anticancer agents), the properties of the compounds (e.g., bioavailability, stability, potency, toxicity, etc.), and the particular disorder(s) the subject is suffering from. In addition, the therapeutically effective amount may depend on the subject's blood parameters (e.g., lipid profile, insulin levels, glycemia), the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained. The dose to be administered will ultimately be at the discretion of the oncologist. In general, however, the dose will be in the range from about 1 to about 100 mg/kg per day when administered orally; and in the range from about 0.01 to about 10 mg/kg per day when administered intravenously or subcutaneously.

As used herein, the term "pharmaceutical composition" refers to the presence of at least one compound of the invention according to Formula I, Formula I.1, Formula I.2, Formula IA, Formula IB, Formula IC or Formula II as defined herein and at least one pharmaceutically acceptable carrier, diluent, vehicle or excipient. As used herein, the term "pharmaceutically acceptable carrier", "pharmaceutically acceptable diluent" or "pharmaceutically acceptable excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethyleneglycol matrix, which is acceptable for use in subjects, preferably humans. It preferably refers to a compound or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

The composition of the present invention may include one or more compounds of Formula I, Formula I.1, Formula I.2, Formula IA, Formula IB, Formula IC or Formula II as defined herein or pharmaceutically acceptable derivatives, salts prodrugs, analogues and isomers or enantiomers thereof. Formulations of the active compound may be prepared so as to provide a pharmaceutical composition in a form suitable for enteral, mucosal (including sublingual, pulmonary and rectal), parenteral (including intramuscular, intradermal, subcutaneous and intravenous) or topical (including ointments, creams or lotions) administration. The formulation may, where appropriate, be conveniently presented in discrete dosage units and may be prepared by any of the methods well-known in the art of pharmaceutical formulation. All methods include the step of bringing together the active pharmaceutical ingredient with liquid carriers or finely divided solid carriers or both as the need dictates. When appropriate, the above-described formulations may be adapted so as to provide sustained release of the active pharmaceutical ingredient. Sustained release formulations well-known to the art include the use of a bolus injection, continuous infusion, biocompatible polymers or liposomes.

E) Kits

The compound(s) of the invention may be packaged as part of a kit, optionally including a container (e.g., packaging, a box, a vial, etc.). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compound(s) of the invention may or may not be administered to a patient at the same time or by the same route of administration. Therefore, the methods of the invention encompass kits which, when used by the medical practitioner, can simplify the administration of appropriate amounts of two or more active ingredients to a patient.

A typical kit of the invention comprises a unit dosage form of at least one compound according to the invention as defined by Formula I, Formula I.1, Formula I.2, Formula IA, Formula IB, Formula IC or Formula II as defined herein, or a pharmaceutically acceptable salt thereof, and a unit dosage form of at least one additional active ingredient. Examples of additional active ingredients that may be used in conjunction with the compounds of the invention include, but are not limited to, any of the anticancer agents indicated hereinbefore that could be used in combination with the compound(s) of the invention.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles are provided hereinbefore.

EXAMPLES

The following examples further illustrate the practice of this invention but are not intended to be limiting thereof.

Instrumentation:

All HPLC chromatograms and mass spectra were recorded on an HP 1100 LC-MS Agilent instrument using an analytical C18 column (250×4.6 mm, 5 microns) with a gradient over 5 min of 15-99% CH$_3$CN—H$_2$O with 0.01% TFA as the eluant and a flow of 2 mL/min.

Example 1

Preparation of Substituted Phenylacetic Acid Compounds

Compound I: Synthesis of sodium salt of (3-pentylphenyl) acetic acid using a modified Sonogashira procedure

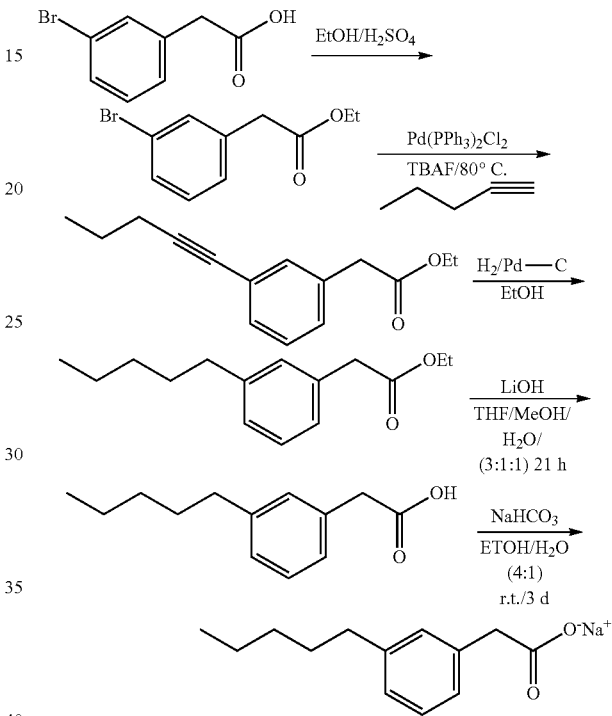

Step 1: To a solution/suspension of 3-bromophenylacetic acid (5.02 g, 23.33 mmol) in ethanol (100 mL) at room temperature was added concentrated sulfuric acid (1 mL). The colorless solution was then stirred overnight at 80° C. The solution was concentrated under reduced pressure. The residue was diluted with ethyl acetate (25 mL), water (25 mL) and the two layers were separated. The aqueous layer was extracted with ethyl acetate (2×25 mL) and brine (20 mL). The combined organic layers were washed with saturated solution of NaHCO$_3$ (2×25 mL), brine (25 mL) and dried over sodium sulfate. After filtration the solution it was evaporated to dryness. This gave a light yellow oil (5.4 g, 95%). $^1$H-NMR (400 MHz, CDCl$_3$): δ 1.26 (t, J=4.7 Hz, 3H), 3.57 (s, 2H), 4.15 (Q, J=7.0 and 14.3 Hz, 2H), 7.17-7.26 (m, 2H), 7.38-7.44 (m, 1H), 7.44 (d, J=1.56 Hz, 1H).

Step 2: A mixture of ethyl(3-bromophenyl)acetate (0.3 g, 1.24 mmol) and tetrabutylammonium fluoride hydrate (0.97 g, 3.72 mmol), was treated with PdCl$_2$(PPh$_3$)$_2$(26 mg, 0.037 mmol; 3 mole %) and 1-pentyne (367 μL, 3.72 mmol) in a sealed tube. The tube was heated at 80° C. for 2 h. The mixture was treated with water, and was extracted with diethyl ether. The organic extract was dried over sodium sulfate, filtered and evaporated in vacuo to give the crude product. Purification on a Biotage™ 25 M column (silica), eluting with ethyl acetate/hexane 0:1 to 2:98, gave ethyl (3-(pentyne-1-yl)phenyl)acetate as a pale yellow oil (0.23 g, 79%).

Step 3: To ethyl[3-[pentyne-1-yl]phenyl]-acetate (0.23 g, 0.98 mmol) in ethanol (5 mL) under nitrogen atmosphere was added Pd on carbon (10%, 25 mg, 10% w/w). The mixture was vigorously stirred under hydrogen atmosphere at room temperature overnight. The solution was filtered and the palladium/carbon was washed with ethanol (20 mL). The filtrate was concentrated with silica gel. The crude product was purified by flash chromatography using a mixture of 10% hexanes/ethyl acetate. A clear oil was obtained (0.21 g, 90%).

Step 4: To a solution of the ester (0.2 g, 0.9 mmol) in tetrahydrofuran (5 mL), methanol (1.5 mL) and water (1.5 mL) was added lithium hydroxide (0.09 g, 3.6 mmol) at 0° C. The reaction mixture was stirred overnight at room temperature. Insolubles were filtered and the filtrate was concentrated under reduced pressure. The residue was then treated with 2 M HCl and extracted with ethyl acetate. The organic phase was dried over sodium sulfate and evaporated under reduced pressure. The crude material was purified on a 40 L Biotage™ column (silica) using ethyl acetate/hexanes (0:10 to 4:6) as eluant. This gave pure (3-pentylphenyl)acetic acid (0.19 g, 99%) as a white gummy solid. $^1$H NMR (400 MHz, $CD_3OD$): δ 0.90 (t, J=7.0 Hz, 3H), 1.28-1.38 (m, 4H), 1.61 (qt, J=7.6 Hz, 15.0 Hz, 2H), 2.58 (t, J=7.6 Hz, 2H), 3.56 (s, 2H), 7.07 (m, 3H), 7.20 (m, 1H); LRMS (ESI): m/z 207 ($MH^+$); HPLC: 4.3 min.

Step 5: To a stirred solution of the acid (0.19 g, 0.82 mmol) in ethanol (4 mL) and water (1 mL) was added sodium bicarbonate (0.07 g, 0.82 mmol). The reaction mixture was stirred at room temperature overnight. The solvent was evaporated and the white gummy solid was dissolved in water and the solution lyophilized. This gave pure sodium salt of (3-pentylphenyl)acetic acid (0.17 g, 92%) as a white solid. mp 124-126° C.; $^1$H NMR (400 MHz, $CD_3OD$): δ 0.89 (t, J=6.8 Hz, 3H), 1.28-1.37 (m, 4H), 1.60 (qt, J=7.4 Hz, 15.0 Hz, 2H), 2.56 (t, J=7.6 Hz, 2H), 3.43 (s, 2H), 6.96 (m, 1H), 7.12 (m, 3H); LRMS (ESI): m/z 207 (($MH^+$); HPLC: 4.3 min.

Compound II, Sodium salt of 3-(3-pentylphenyl)propionic acid

The above compound was prepared as for Compound I starting with 3-Oxo-3-bromophenylpropionic acid ethyl ester. The ketone group and the double bond were simultaneously reduced using palladium/carbon in ethanol under hydrogen pressure. White solid; $^1$H NMR (400 MHz, $CDCl_3$): δ 7.14-7.10 (m, 1H), 7.04-7.00 (m, 2H), 6.95-6.93 (m, 1H), 2.88-2.84 (m, 2H), 2.55 (t, J=7.4 Hz, 2H), 2.44-2.40 (m, 2H), 1.63-1.55 (m, 2H), 1.35-1.28 (m, 4H), 0.90 (m, 3H); $^{13}$C NMR (101 MHz, $CD_3OD$): δ 179.3, 141.2, 140.8, 126.7, 126.4, 124.0, 123.8, 38.6, 34.2, 31.2, 29.9, 29.8, 20.9, 11.7; LRMS (ESI): m/z 203 ($MH^+$—CO—NaOH); HPLC: 4.5 min.

Compound IV, Sodium salt of e-(3-pent-1-enyl-phenyl)acetic acid

The above compound was prepared as for Compound I starting with E-(3-pent-1-enyl-phenyl)acetic acid methyl ester. The latter was prepared by reacting 3-bromophenyl acetic acid methyl ester with trans-1-pentenylboronic acid pinacol ester under Suzuki conditions. White solid; $^1$H NMR (400 MHz, $CD_3OD$): δ=7.32 (s, 1H), 7.11-7.18 (m, 3H), 6.35 (d, J=15.7 Hz, 1H), 6.20-6.27 (m, 1H), 3.44 (s, 2H), 2.19 (m, 2H), 1.45-1.54 (m, 2H), 0.96 (t, J=7.4, 3H); $^{13}$C NMR (101 MHz, $CD_3OD$): δ=179.26, 138.25, 137.92, 130.32, 130.04, 128.06, 127.59, 126.60, 123.52, 45.21, 35.06, 22.52, 12.89; LRMS (ESI): m/z 205 ($MH^+$); HPLC: 4.1 min.

Compound V, Sodium salt of E/Z-(3-Pent-3-enylphenyl)acetic acid

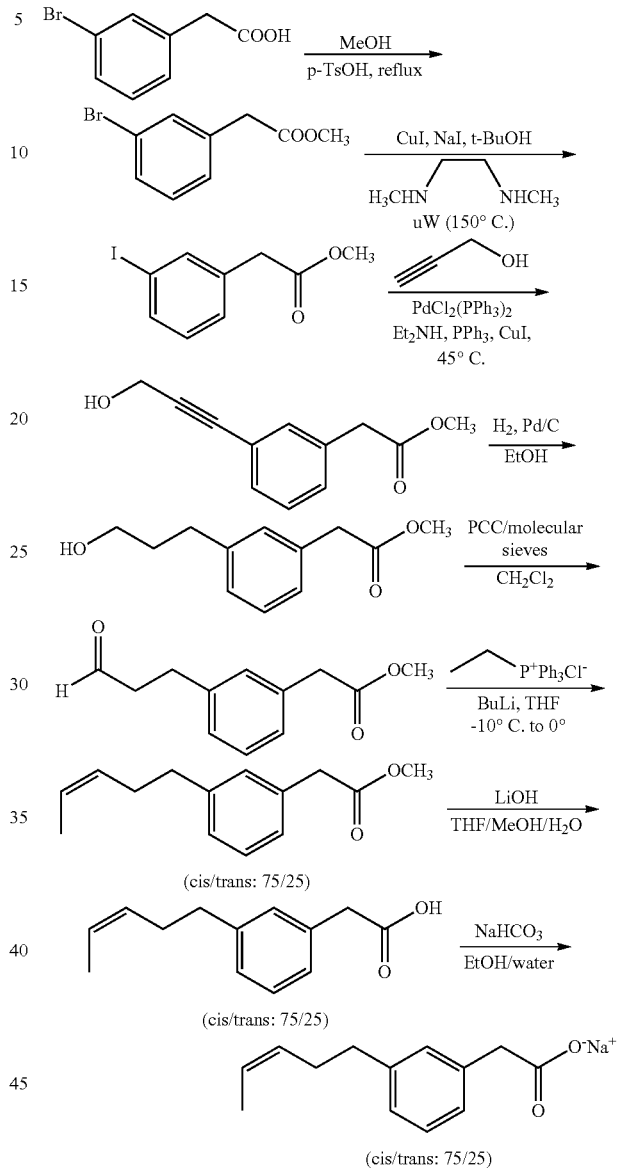

(cis/trans: 75/25)

(cis/trans: 75/25)

(cis/trans: 75/25)

Step 1: To a solution of (3-bromophenyl)acetic acid (12.2 g, 56.8 mmol) in methanol (150 mL) was added p-toluenesulfonic acid (5.4 g, 28.4 mmol). The reaction mixture was stirred at reflux for 3 h. The solvent was evaporated and the residue was dissolved in a mixture of ethyl acetate/water (3:2). The organic layer was dried over sodium sulfate and concentrated. The residue was purified using a silica pad eluting with a mixture of hexanes/ethyl acetate (9:1). This gave (3-bromophenyl)acetic acid methyl ester as a colorless oil (11.7 g, 90%). $^1$H NMR (400 MHz, $CD_3OD$): δ=7.46 (m, 1H), 7.41 (m, 1H), 7.22 (m, 2H), 3.68 (s, 3H), 3.65 (s, 2H); LRMS (ESI): m/z=229 ($MH^+$); HPLC: 3.8 min.

Step 2: To a solution of the ester (6.0 g, 26.2 mmol) in tert-butanol (24 mL) was added under nitrogen, sodium iodide (7.8 g, 52.4 mmol), N,N'-dimethylethylenediamine (0.3 mL, 2.6 mmol) and copper iodide (0.3 g, 1.3 mmol). The reaction mixture was heated in a microwave apparatus at 145°

C. for 1 h. Water (100 mL) was added and the product was extracted with ethyl acetate (3×50 mL). The organic layer was dried over sodium sulfate and concentrated. The residue was purified by flash chromatography on silica gel with a mixture of hexanes/ethyl acetate (8:2). This gave 3-iodophenylacetic acid methyl ester as a colorless oil (6.6 g, 86%). $^1$H NMR (400 MHz, CDCl$_3$): δ=7.63 (m, 1H), 7.58-7.61 (m, 1H), 7.23-7.26 (m, 1H), 7.05 (dd, J=7.8 Hz, 1H), 3.69 (s, 3H), 3.56 (s, 2H); LRMS (ESI): m/z=277 (MH$^+$).

Step 3: The iodoester (6.2 g, 22.5 mmol) was mixed with palladium chloride (0.16 g, 0.22 mmol), triphenylphosphine (59.0 mg, 0.22 mmol) and diethylamine (60 mL) under nitrogen. To this mixture was added copper(1) iodide (43 mg, 0.22 mmol) and propargyl alcohol (1.57 g, 28.1 mmol) and the reaction mixture was stirred overnight at 45° C. Diethylamine was removed under reduced pressure and 100 mL of water was added. The mixture was then extracted with ethyl acetate (3×30 mL) and the crude product was purified by flash chromatography using a mixture of ethyl acetate/hexanes (30%). This gave pure [3-(3-hydroxyprop-1-ynyl)phenyl]acetic acid methyl ester as a brownish oil (3.8 g, 84%). $^1$H NMR (400 MHz, CDCl$_3$): δ=7.33-7.37 (m, 2H), 7.23-7.30 (m, 2H), 4.49 (d, J=6.1 Hz, 2H), 3.69 (s, 3H), 3.60 (s, 2H), 1.68 (t, J=6.3 Hz, 1H); LRMS (ESI): m/z=227 (MNa$^+$); HPLC: 2.7 min.

Step 4: To the methyl ester (3.8 g, 18.7 mmol) in ethanol (70 mL) under nitrogen was added 10% palladium/carbon (0.30 g). The atmosphere was changed for hydrogen. The mixture was vigorously stirred at room temperature overnight. The solution was filtered and the palladium/carbon washed with ethanol (50 mL). The filtrate was concentrated and the crude product was purified by flash chromatography using a mixture of hexanes/ethyl acetate (3:2). This gave pure 3-(3 hydroxypropyl)phenyl]acetic acid methyl ester as a colorless oil (3.20 g, 82%). $^1$H NMR (400 MHz, CD$_3$OD): δ=7.21 (t, J=7.6 Hz, 1H), 7.11 (s, 1H), 7.07 (m, 2H), 3.67 (s, 3H), 3.61 (s, 2H), 3.56 (t, J=7.6 Hz, 2H), 2.66 (t, J=7.6 Hz, 2H), 1.78-185 (m, 2H); LRMS (ESI): m/z=209 (MH$^+$); HPLC: 2.6 min.

Step 5: At 0° C. under nitrogen, pyridinium chlorochromate (1.44 g, 6.70 mmol) and molecular sieves were added to a solution of the methyl ester (0.9 g, 4.4 mmol) in dry dichloromethane (20 mL). The reaction mixture was stirred for 20 min at 0° C. and 3 h at room temperature. Ether (20 mL) was added and the precipitate was filtered and washed with ether (40 mL). The filtrate was evaporated to give [3-(3-oxopropyl) phenyl]acetic acid methyl ester as a brownish oil (0.9 g, 97%). The aldehyde was used in the next step without further purification. $^1$H NMR (400 MHz, CDCl$_3$): δ=9.82 (t, J=1.4 Hz, 1H), 7.24-7.28 (m, 2H), 7.11 (m, 2H), 3.69 (s, 3H), 3.60 (s, 2H), 2.95 (t, J=7.6 Hz, 2H), 2.80 (t, J=7.0 Hz, 2H).

Step 6: The aldehyde (0.9 g, 4.3 mmol) was dissolved in tetrahydrofuran (9 mL). In a separate flask containing a solution of (ethyl)triphenylphosphonium bromide (2.1 g, 5.6 mmol) in dry tetrahydrofuran (17 mL) at −10° C. was added a solution of 2.3 M n-butyllithium (1.94 mL, 5.8 mmol). The orange solution was stirred at this temperature for 20 min and at 0° C. for 40 min. To this solution was added the aldehyde and the mixture stirred for 1 h at 0° C. and at room temperature overnight. Water (30 mL) was added and the organic layer was extracted with ether (3×30 mL). The combined ether layers were washed with brine and dried. The solvent was evaporated and the residue was purified using a mixture of petroleum ether/ethyl acetate (95%) as eluent. This gave pure E/Z-(3-pent-3-enyl-phenyl)acetic acid methyl ester as a colorless oil (0.25 g, 27%). $^1$H NMR (400 MHz, CDCl$_3$): δ=7.13-7.18 (m, 1H), 7.06-7.08 (m, 3H), 5.31-5.44 (m, 2H), 3.62 (s, 3H), 3.52 (d, J=7.2 Hz, 2H), 2.57 (t, J=7.8 Hz, 2H), 2.25-2.31 (m, 2H), 1.57 (dd, J=3, 3, 1.4 Hz, 3H).

Step 7: To a solution of the olefin (0.13 g, 0.60 mmol) in tetrahydrofuran (3 mL), methanol (1.5 mL) and water (1.5 mL) was added lithium hydroxide (73 mg, 3.1 mmol) at 0° C. The reaction mixture was stirred overnight at room temperature. The solvent was concentrated, acidified with 2 M hydrochloric acid and extracted with ethyl acetate (3×15 mL). The organic phase was dried and evaporated under high vacuum. The crude product was purified on a silica pad with ethyl acetate/hexanes (20%). This gave pure E/Z-(3-Pent-3-enylphenyl)acetic acid (0.12 g, 100%) as colorless oil. $^1$H NMR (400 MHz, CDCl$_3$): δ=10.70-11.50 (br s, 1H), 7.26-7.30 (m, 1H), 7.13-7.20 (m, 3H), 5.44-5.53 (m, 2H), 3.65 (s, 2H), 2.67-2.71 (m, 2H), 2.33-2.42 (m, 2H), 1.58-1.68 (m, 3H).

Step 8: To a stirred solution of the acid (0.12 g, 0.6 mmol) in ethanol (3 mL) and water (2 mL) was added sodium bicarbonate (50 mg, 0.6 mmol). The reaction mixture was stirred at room temperature overnight. The solvent was concentrated and the residue was diluted in water (70 mL) and the solution was lyophilized. This gave pure sodium salt E/Z-(3-pent-3-enylphenyl)acetic acid as a white solid (0.14 g, 90%). $^1$HNMR (400 MHz, D$_2$O): (major, E-isomer) δ=7.12 (dd, J=7.4 Hz, 1H), 7.00 (s, 1H), 6.99 (d, J=7.4 Hz, 1H), 6.95 (d, J=7.6 Hz, 1H), 5.27-5.38 (m, 2H), 3.33 (s, 2H), 2.53-2.48 (m, 2H), 2.13-2.24 (m, 2H), 1.35-1.44 (m, 3H).

Compound VII, Sodium salt of 3-(4-fluoro-3-pentylphenyl) propionic acid

The above compound was prepared as for Compound I starting with E-methyl 3-(3-bromo-4-fluorophenyl)acrylate. The latter was prepared by mixing a solution of 3-bromo-4-fluorobenzaldehyde and ethoxycarbonylmethylenetriphenylphosphorane in dry dichloromethane at room temperature. White solid; $^1$H NMR (400 MHz, CD$_3$OD): δ=6.67-6.74 (m, 2H), 6.58 (m, 1H), 2.49 (t, J=7.6 Hz, 2H), 2.23 (t, J=7.4 Hz, 2H), 2.15 (m, 2H), 1.25 (m, 2H), 0.99-1.06 (m, 4H), 0.61 (t, J=6.7 Hz, 3H); $^{13}$C NMR (101 MHz, D$_2$O): δ=182.38, 160.69, 158.28, 137.37, 130.34, 129.58, 126.84, 114.99, 39.68, 31.51, 29.92, 28.90, 22.31, 16.66; LRMS (ESI): m/z 221 (MH$^+$—H$_2$O); HPLC: 4.5 min.

Compound VIII, Sodium salt of [3-Hydroxy-5-pentylphenyl] acetic acid

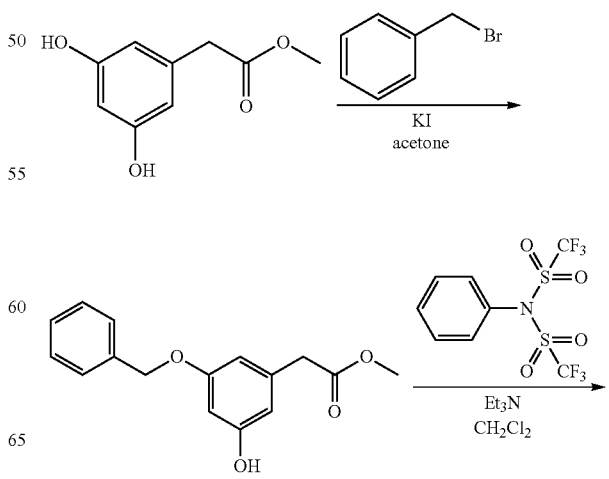

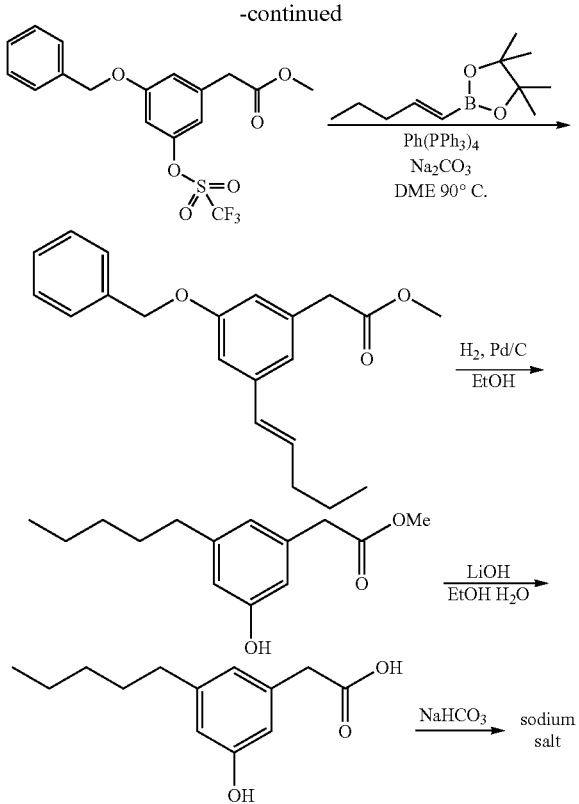

Step 1: A solution of methyl [3,5-dihydroxyphenyl]acetate (2.1 g, 11.5 mmol) in acetone (100 mL) was treated with potassium carbonate (2.4 g, 17.4 mmol), potassium iodide (0.38 g, 2.31 mmol) and benzyl bromide (1.5 mL, 12.7 mmol), and the mixture was stirred at room temperature overnight. The reaction was diluted with water, and was extracted with dichloromethane (×3). Combined organic extracts were dried over sodium sulfate and evaporated in vacuo. The crude material was purified on a Biotage™ 40 M column (silica), eluting with 40% ethyl acetate/hexane, to give methyl [3-benzyloxy-5-hydroxyphenyl]acetate (1.0 g, 33%). $^1$H NMR (400 MHz, CDCl$_3$): δ 7.32-7.42 (m, 5H), 6.48 (d, J=1.4 Hz, 1H), 6.38-6.39 (m, 2H), 4.99 (s, 2H), 3.69 (s, 3H), 3.53 (s, 2H).

Step 2: A solution of the benzyl ether (1.04 g, 3.8 mmol) in dichloromethane (15 mL) at 0° C., was treated with N-phenyl-bis(trifluorosulfonyl)imide (1.40 g, 3.9 mmol), and then triethylamine (0.6 mL, 4.1 mmol) was added slowly. The reaction was stirred at 0° C. for 1 h, and then at room temperature for 1 h. The reaction mixture was diluted with water, and then extracted with diethylether (×2). Combined organic extracts were washed with 1 M aqueous sodium hydroxide, water (×2) and saturated aqueous sodium chloride, then dried over sodium sulfate, filtered and evaporated in vacuo, to give the crude product. Purification on a Biotage™ 40 M column (silica), eluting with ethyl acetate/hexane 0:1 to 1:4, gave methyl [3-benzyloxy-5-trifluoromethanesulfonyloxyphenyl] acetate (1.2 g, 79%). $^1$H NMR (400 MHz, CDCl$_3$): δ 7.36-7.46 (m, 5H), 6.98 (s, 1H), 6.97 (s, 1H), 6.84 (s, 1H), 5.06 (s, 2H), 3.72 (s, 3H), 3.63 (s, 2H).

Step 3: A solution of E-1-penten-1-ylboronic acid pinacol ester (0.8 g, 3.9 mmol) in dimethoxyethane (5 mL) was treated with a solution of the triflate (1.2 g, 3.0 mmol) in dimethoxyethane (5 mL). The solution was treated with palladium zero (0.7 g, 0.6 mmol) and 2M aqueous sodium carbonate (1.3 mL, 2.6 mmol). The mixture was then heated at 90° C. for 3 days. The reaction was cooled to room temperature and filtered through celite. The filtrate was evaporated in vacuo, and the crude material was purified on a Biotage™ 25 M column (silica), eluting with ethyl acetate/hexane 0:1 to 5:95, to give methyl [3-benzyloxy-5-[pent-1-enyl]phenyl]acetate (0.4 g, 40%). $^1$H NMR (400 MHz, CDCl$_3$): δ 7.36-7.47 (m, 5H), 6.90-6.92 (m, 2H), 6.79 (dd, J=2.0, 2.0 Hz, 1H), 6.35 (d, J=15.9 Hz, 1H), 6.24 (dt, J=15.9, 6.8 Hz, 1H), 5.07 (s, 2H), 3.70 (s, 3H), 3.59 (s, 2H), 2.20 (td, J=7.4, 6.8 Hz, 2H), 1.51 (dt, J=7.4 Hz, 2H), 0.98 (t, J=7.4 Hz, 3H).

Step 4: A solution of the alkene (0.4 g, 1.2 mmol) in ethanol (13 mL) was treated with 1% palladium on carbon (40 mg). The mixture was stirred under 1 atm. of hydrogen at room temperature overnight. The reaction was filtered, evaporated in vacuo, and purified on a Biotage™ 25 S column (silica), eluting with ethyl acetate/hexane 0:1 to 15:85 to give methyl [3-hydroxy-5-pentylphenyl]acetate (0.3 g, 93%). $^1$H NMR (400 MHz, CDCl$_3$): δ 6.64 (s, 1H), 6.58-6.60 (m, 2H), 3.70 (s, 3H), 3.55 (s, 2H), 2.51 (t, J=7.7 Hz, 2H), 1.55-1.59 (m, 2H), 1.28-1.34 (m, 4H), 0.88 (t, J=7.0 Hz, 3H).

Step 5: A solution of the ester (0.3 g, 1.3 mmol) in ethanol (12 mL) was treated with water (3 mL) and lithium hydroxide (155 mg, 6.4 mmol), and the mixture was stirred vigorously at room temperature overnight. The reaction mixture was diluted with water (100 mL); washed with dichloromethane; then acidified to pH 1 with 1 M hydrochloric acid and extracted with dichloromethane (×3). Combined organic extracts were dried over sodium sulfate (0.3 g, 95%). This material was used without further purification. $^1$H NMR (400 MHz, CDCl$_3$): δ 6.66 (s, 1H), 6.58-6.59 (m, 2H), 3.55 (s, 2H), 2.52 (t, J=7.7 Hz, 2H), 1.55-1.59 (m, 2H).

Step 6: A solution of the acid (0.27 g, 1.23 mmol) in ethanol (6 mL) and water (6 mL) was treated with sodium bicarbonate (0.1 g, 1.2 mmol), and the reaction was stirred at room temperature for a few hours. Solvent was concentrated in vacuo, and the solution was diluted with water, filtered (0.2 μm), and lyophilized to give sodium [3-hydroxy-5-pentylphenyl]acetate as a white solid (0.3 g, 95%). mp 263-266° C.; $^1$H NMR (400 MHz, CD$_3$OD): δ 6.63 (s, 1H), 6.58 (s, 1H), 6.42 (s, 1H), 3.36 (s, 2H), 2.48 (t, J=7.6 Hz, 2H), 1.55-1.62 (m, 2H), 1.26-1.38 (m, 4H), 0.89 (t, J=6.8 Hz, 3H); $^{13}$C NMR (101 MHz, CD$_3$OD): δ 177.79, 155.31, 142.36, 137.62, 119.08, 111.66, 111.18, 43.70, 34.17, 29.95, 29.56, 20.87, 11.64; LRMS (ESI): m/z 445.2 (2M−2Na$^+$+3H$^+$), m/z 223 (M−Na$^+$+2H$^+$); HPLC: 3.5 min.

Compound IX, Sodium 2-[4-Hydroxy-3-pentylphenyl]acetate

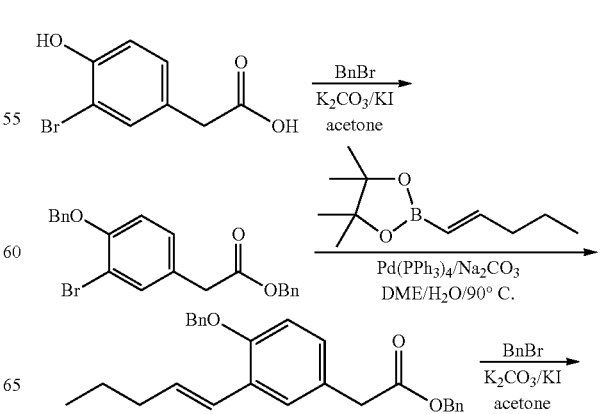

-continued

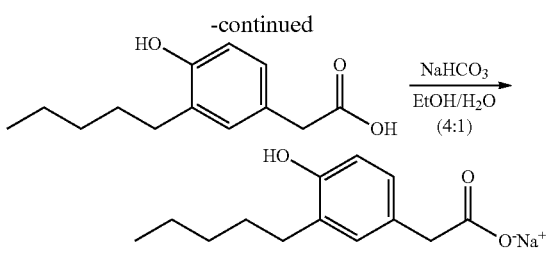

A mixture of 2-[3-bromo-4-hydroxyphenyl]acetic acid (2.0 g, 8.7 mmol), potassium carbonate (3.7 g, 26.7 mmol) and potassium iodide (577 mg, 3.5 mmol) in acetone (25 mL) was treated with benzyl bromide (2.6 mL, 22.0 mmol), and the reaction was stirred at room temperature for 3 days. The reaction mixture was partitioned between ethyl acetate (100 mL) and 1M hydrochloric acid (100 mL); and the organic phase was then washed with saturated sodium hydrochloric acid (50 mL); dried over sodium sulfate; filtered and evaporated in vacuo to give the crude product. Purification on a Biotage™ SP1 system (40M silica; eluting with 0-50% ethyl acetate over 25CV) gave benzyl 2-[4 benzyloxy-3-bromophenyl]acetate (3.4 g, 94%) as a colourless oil. $^1$H NMR (400 MHz, CDCl$_3$): δ 7.47-7.52 (m, 3H), 7.32-7.42 (m, 8H), 7.15 (d, J=8.2 Hz, 1H), 6.89 (d, J=8.4 Hz, 1H), 5.15 (s, 2H), 5.14 (s, 2H), 3.59 (s, 2H). Suzuki coupling of benzyl 2-[4-benzyloxy-3-bromophenyl]acetate (3.1 g, 7.5 mmol) according to standard protocol, gave benzyl (E)-2-[4-benzyloxy-3-[pent-1-enyl]phenyl]acetate (2.2 g, 72%). $^1$H NMR (400 MHz, CDCl$_3$): δ 7.32-7.47 (m, 11 H), 7.08 (dd, J=8.3, 2.2 Hz, 1H), 6.89 (d, J=8.4 Hz, 1H), 6.77 (d, J=16.0 Hz, 1H), 6.23 (dt, J=16.0, 7.0 Hz, 1H), 5.15 (s, 2H), 5.10 (s, 2H), 3.62 (s, 2H), 2.21 (tdd, J=7.2, 7.2, 1.4 Hz, 2H), 1.50 (qt, J=7.4, 7.2 Hz, 2H), 0.97 (t, J=7.4 Hz, 3H). A solution of the ester (2.2 g, 5.4 mmol) in ethyl acetate (20 mL) was then treated with palladium on carbon (10% w/w Pd; 215 mg). The mixture was thoroughly degassed in vacuo under hydrogen. The reaction was stirred at ambient temperature under one atmosphere of hydrogen for 17 h, then filtered through celite and evaporated in vacuo to give the crude product. Purification on a Biotage™ SP1 system (25M silica cartridge; eluting with 0-50% ethyl acetate over 30CV) gave 2-[4-hydroxy-3-pentylphenyl]acetic acid (1.1 g, 91%). $^1$H NMR (400 MHz, CDCl$_3$): δ 7.02 (d, J=2.3 Hz, 1H), 6.97 (dd, J=8.1, 2.2 Hz, 1H), 6.63 (d, J=8.0 Hz, 1H), 3.34 (s, 2H), 2.53 (t, J=7.8 Hz, 2H), 1.56-1.63 (m, 2H), 1.31-1.37 (m, 4H), 0.89 (t, J=7.0 Hz, 3H); $^{13}$C NMR (101 MHz, CDCl$_3$): δ 178.60, 153.19, 131.34, 129.40, 127.98, 125.32, 115.61, 40.55, 32.01, 30.17, 29.64, 22.80, 14.29. The resulting acid (1.1 g, 5.1 mmol) was then converted to the sodium salt by standard protocol, to give sodium 2-[4-hydroxy-3-pentylphenyl]acetate (1.3 g, quantitative yield) as a white solid. mp 193-197° C.; $^1$H NMR (400 MHz, CD$_3$OD): δ 7.01 (d, J=2.0 Hz, 1H), 6.93 (dd, J=8.1, 2.3 Hz, 1H), 6.71 (d, J=8.0 Hz, 1H), 3.55 (s, 2H), 2.56 (t, J=7.8 Hz, 2H), 1.54-1.59 (m, 2H), 1.28-1.38 (m, 4H), 0.90 (t, J=7.0 Hz, 3H); $^{13}$C NMR (101 MHz, CD$_3$OD): δ 180.18, 153.17, 130.54, 128.83, 128.74, 127.08, 114.45, 44.44, 31.83, 30.08, 29.72, 22.51, 13.28; LRMS (ESI): m/z 445.6 (2M−2Na$^+$+3H$^+$), 223.2 (M−Na$^+$+2H$^+$), 177.2 (tropylium ion); HPLC: 2.2 min.

Compound X, Sodium salt of (2-hydroxy-5-pentylphenyl) acetic acid.

The above compound was prepared as for Compound I starting with 5-bromo-2-methoxyphenylacetic acid methyl ester. Demethylation of the methoxy group was undertaken using a solution of boron tribromide (1 M/CH$_2$Cl$_2$) at −78° C. for 1 h then at 00° C. during 20 min. White solid; $^1$H NMR (400 MHz, CD$_3$OD): δ=6.88 (m, 2H), 6.71 (d, J=8.6 Hz, 1H), 3.50 (s, 2H), 2.49 (t, J=7.6 Hz, 2H), 1.54-1.62 (m, 2H), 1.29-1.38 (m, 4H), 0.91 (t, J=7.0 Hz, 3H); $^{13}$C NMR (101 MHz, CD$_3$OD): δ=180.08, 154.04, 134.03, 130.26, 127.36, 124.15, 116.57, 42.48, 34.91, 31.60, 31.42, 22.45, 13.24; LRMS (ESI): m/z 177 (MH$^+$−CO−NaOH); HPLC: 3.7 min.

Compound XI, Sodium salt of 4-pentylbenzoic acid.

The above compound was prepared as for Compound I starting with 4-pentylbenzoic acid. White solid; $^1$H NMR (400 MHz, D$_2$O): δ 7.61 (d, J=8.3 Hz, 2H), 7.12 (d, J=8.5 Hz, 2H), 2.46 (t, J=7.5 Hz, 2H), 1.38-1.45 (m, 2H), 1.04-1.15 (m, 4H), 0.65 (t, J=7.0 Hz, 3H); $^{13}$C NMR (101 MHz, D$_2$O): δ 175.79, 147.29, 133.55, 129.15, 128.47, 35.07, 30.81, 30.45, 22.00, 13.42; LRMS (ESI): m/z 193 (M−Na$^+$+2H$^+$); HPLC: 4.3 min.

Compound XIII, Sodium salt of 3-hexylbenzoate

3-Hexylbenzoic acid was converted to the sodium salt by the standard procedure. mp 197-199° C.; $^1$H NMR (400 MHz, CDCl$_3$): δ 7.79 (s, 1H), 7.75 (ddd, J=7.0, 1.7, 1.7 Hz, 1H), 7.25 (dd, J=7.6, 7.0 Hz, 1H), 7.21 (ddd, J=7.6, 1.8, 1.8 Hz, 1H), 2.63 (t, J=7.5 Hz, 2H), 1.63 (tt, J=7.5, 7.0 Hz, 2H), 1.27-1.38 (m, 6H), 0.89 (t, J=7.5 Hz, 3H); $^{13}$C NMR (101 MHz, CDCl$_3$): δ 174.64, 142.29, 137.65, 130.28, 129.13, 127.47, 126.50, 35.73, 31.74, 31.55, 28.89, 22.52, 13.28; LRMS (ESI): m/z 207.2 (M−Na$^+$+2H$^+$); HPLC: 3.0.

Example 2

Preparation of Substituted Phenylpropionic Acid Compounds

General scheme :

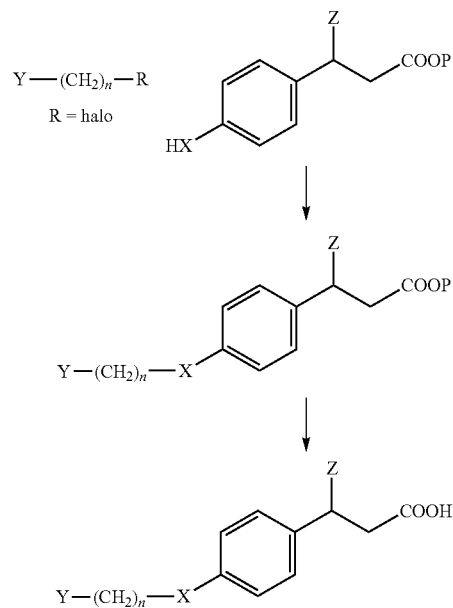

P = protecting group
X, Y, Z, n defined as above

Compound XIV, (±)3-(4-[4-methoxyphenyl)methoxy]phenyl)-hex-4-ynoic acid.

Representative procedure where n=1, Z=—C≡C—CH$_3$, X=O and Y=3-O—CH$_2$—C$_6$H$_5$—O—C$_6$H$_5$.

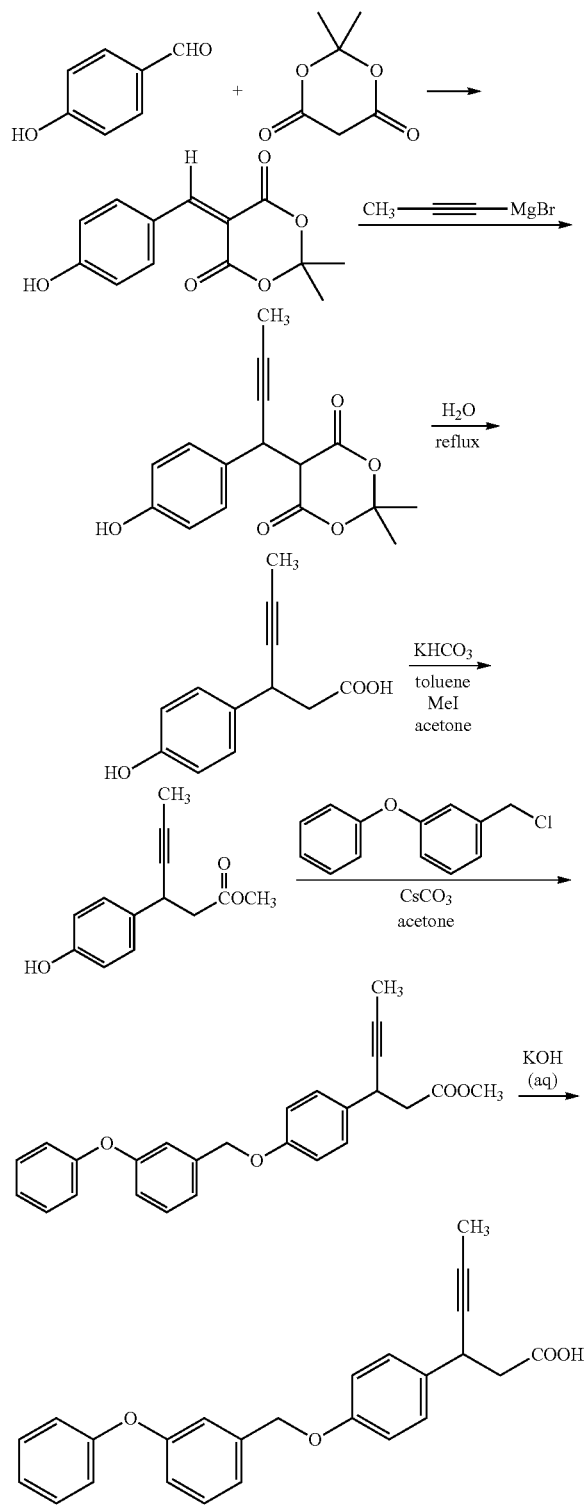

A 2-liter flask was charged with 4-hydroxybenzaldehyde (50 g, 409 mmol) and water (400 mL). The temperature of the reaction was kept at 75° C. and Meldrum's acid (62 g, 430 mmol) was added as a slurry in water (400 mL). The mixture was stirred for 2 h then cooled in an ice bath for 2 h. The product was filtered, rinsed with cold water and dried under vacuum. This gave 5-(4-hydroxybenzylidene)-2,2-dimethyl-[1,3]dioxane-4,6-dione (95 g, 94%) as a yellow solid. $^1$H NMR (500 MHz) (DMSO-d$_6$) δ 9.75 (br, s, 1H); 8.27 (s, 1H); 8.24 (d, 2H, J=10 Hz); 6.98 (d, 2H, J=10 Hz); 1.76 (s, 6H). MS ESI m/e: 519 (2M+Na). This compound was dissolved in anhydrous tetrahydrofuran (350 mL) and added slowly to a solution of 1-propylmagnesium bromide in tetrahydrofuran (0.5 N, 600 mL). The reaction mixture changed to a yellow suspension that was stirred for 15 min. This was quenched with aqueous ammonium chloride (0.6N, 750 mL) and diluted with hexanes (800 mL). The aqueous layer was then acidified to pH 2 with saturated potassium hydrogen sulfate and extracted with ethyl acetate (2×400 mL). The combined extracts were washed with brine, dried over magnesium sulfate, filtered, and concentrated to give (±)-5-[1-(4-hydroxyphenyl)but-2-ynyl]-2,2-dimethyl-[1,3]dioxane-4,6-dione (37.0 g, 91%) as a pale yellow solid. $^1$H NMR (500 MHz) (acetone-d$_6$) δ 8.26 (s, 1H); 7.39 (d, 2H, J=8.5 Hz); 6.76 (d, 2H, J=8.4 Hz); 4.73 (br, s, 1H); 4.46 (d, 1H, J=2.4 Hz); 1.82 (s, 3H); 1.81 (s, 3H); 1.64 (s, 3H). MS ESI m/e: 599 (2M+Na). The phenol derivative (37 g) was suspended in a mixture of diethyl ketone (160 mL) and water (80 mL), then heated to reflux for 48 h. The aqueous layer was saturated with sodium chloride and separated. The organic layer was dried over magnesium sulfate, filtered, and concentrated to a pale brown oil which was crystallized from hot ethyl acetate:hexanes (1:2). This gave (±)3-(4-hydroxyphenyl)-hex-4-ynoic (20.0 g, 77%) as a white powder. $^1$H NMR (500 MHz) (DMSO-d$_6$) δ 12.2 (s, 1H); 9.27 (s, 1H); 7.12 (d, 2H, J=8.5 Hz); 6.67 (d, 2H, J=8.6 Hz); 3.87 (m, 1H); 2.54 (m, 2H); 1.82 (d, 3H, J=2.4 Hz); MS ESI m/e: 205 (M+H); 227 (M+Na). The acid (23.5 g, 115 mmol) was dissolved in acetone (230 mL) and treated with potassium bicarbonate (11.5 g, 115 mmol). After 15 min, methyl iodide (5 mL, 80 mmol) was added and the reaction stirred at 40° C. overnight. An additional portion of methyl iodide (3 mL, 48 mmol) was added and heating was continued for 24 h. Insolubles were removed by filtration and rinsed with acetone. The filtrate was concentrated to an oil which was purified on silica gel using 2.5% methanol in dichloromethane as eluent. This gave 3-(4-hydroxyphenyl)hex-4-ynoic acid methyl ester (21.5 g, 85%) as a pale yellow oil. $^1$H NMR (500 MHz) (acetone-d$_6$) δ 8.2 (br, s, 1H); 7.20 (d, 2H, J=9.5 Hz); 6.77 (d, 2H, J=9.0 Hz); 3.98 (m, 1H); 3.60 (s, 3H); 2.65 (m, 2H); 1.78 (d, 3H, J=2.5 Hz). MS ESI m/e: 219.1 (M+H); 241 (M+Na). The phenol (0.96 g, 4.4 mmol) and 4-methoxybenzyl chloride (0.72 mL, 5.3 mmol) were dissolved in acetone (9 mL) and treated with cesium carbonate (1.45 g, 4.4 mmol). The reaction mixture was stirred at room temperature overnight. Insolubles were filtered and the solution was evaporated under reduced pressure. This gave 3-[4-(4-methoxybenzyloxy)-phenyl]-hex-4-ynoic acid methyl ester (1.67 g, 95%) as a white powder which was used without further purification. To a solution of the ester (1.7 g, 4.25 mmol) in methanol (30 mL) was added 2 N potassium hydroxide (aq., 3.2 mL). The reaction was stirred at room temperature overnight. The aqueous solution was adjusted to pH 2 with 1N HCl (aq) and extracted with ethyl acetate. The combined organic layers were washed with water, brine and the solvent was removed under reduced pressure. This gave an off-white solid. Recrystallization from ethanol gave pure (±)3-(4-[4-methoxyphenyl)methoxy]phenyl)-hex-4-ynoic acid (1.2 g, 73%) as a white powder. $^1$H NMR (500 MHz) (D$_2$O) δ 7.34-7.18 (m, 6H); 6.95 (d, 2H, J=6.5 Hz); 5.05 (s, 2H); 3.88 (m, 1H); 2.47 (d, 2H, J=8.5 Hz); 2.28 (s, 3H); 1.72 (d, 3H, J=2.5 Hz). MS ESI m/e: 309.1 (M+H); 331.0 (M+Na).

Compound XV, 3-(4-(3-phenoxy-benzylamino)phenyl)propionic acid.

Representative procedure where n=1, Z=H, X=NH and Y=3-C$_6$H$_5$—O—C$_6$H$_5$.

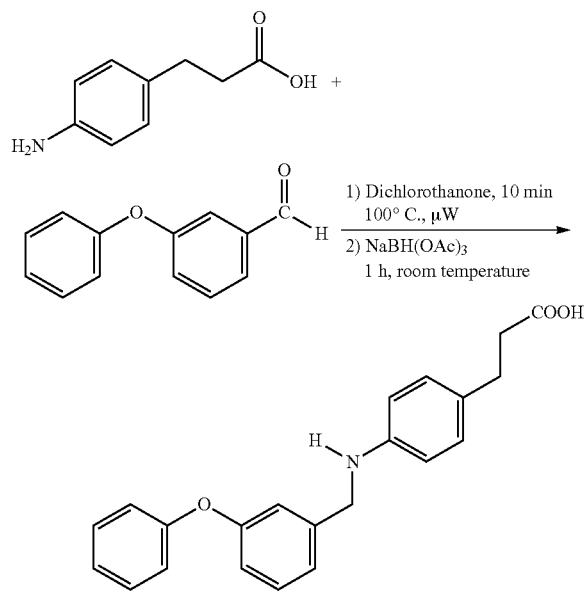

To a solution of 3-phenoxybenzaldehyde (3.2 mL, 18.5 mmol) in dichloroethane (60 mL) was added 3-(4-aminophenyl)propionic acid (3.0 g, 18.5 mmol). The mixture was sonicated and transferred in a microwave vial (20 mL). The reaction was irradiated at 100° C. for 10 min in the microwave. The solution was transferred to a 500 mL round bottom flask and sodium triacetoxy borohydride (7.8 g, 36.9 mmol) was added in a small portion to the mixture. The reaction was stirred at room temperature for 1 h. To the resulting slurry was added water (100 mL) and the organic layer was separated. The latter was extracted twice with water (100 mL) and dried over sodium sulfate. Solvent was then removed and the crude product purified by column chromatography on silica gel using hexanes:ethylacetate (1:1) with trace acetic acid. This gave pure 3-(4-(3-phenoxy-benzylamino)phenyl)propionic acid (5.5 g, 86%) as a low melting point solid. $^1$H NMR (CDCl$_3$) δ 2.40 (t, 2H); 2.63 (t, 2H); 4.21 (s, 2H); 6.09 (bs, 1H); 6.44-6.47 (m, 2H); 6.81-6.83 (m, 1H); 6.87-6.89 (m, 2H); 6.94-6.97 (m, 2H); 7.07 (bs, 1H); 7.11-7.18 (m, 2H); 7.29-7.33 (m, 1H); 7.35-7.38 (m, 2H); 12.09 (bs, 1H); MS m/z=348 (M+H$^+$).

Compound XVI, 3-(4-butoxyphenyl)-3-(3-fluorophenyl)-propionic acid.

Representative procedure where n=4, Z=3-F—CH$_5$, X=0 and Y=zero.

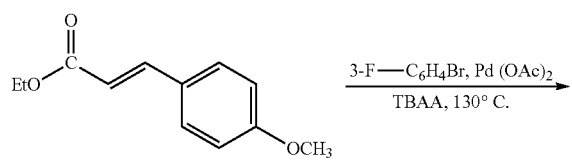

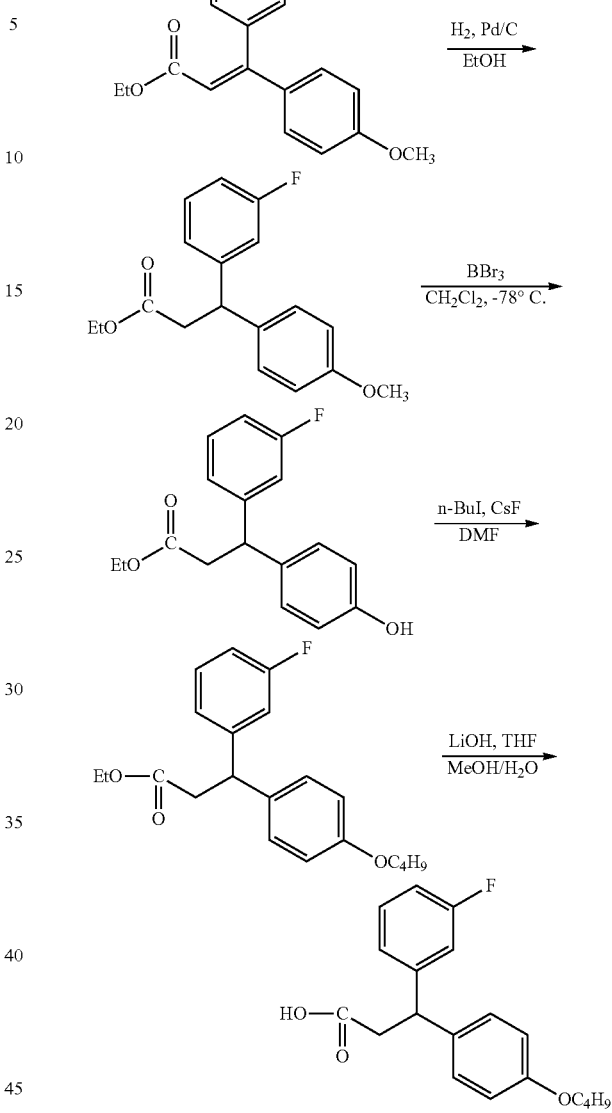

Tetrabutyl ammonium bromide (1.6 g) was melted at 135° C. Ethyl-4-methoxycinnamate (0.6 g, 3.0 mmol), 1-bromo-3-fluorobenzene (0.8 g, 4.5 mmol), palladium acetate (20 mg, 0.1 mmol), and then tetrabutyl ammonium acetate (2.3 g, 7.5 mmol) were added to the ammonium salt. The reaction mixture was stirred at 135° C. for 30 h. Water was added to the cooled mixture and it was extracted with hexane thrice. The combined extracts were washed twice with water and brine, and then dried over sodium sulfate. Solvent was removed under reduced pressure and the crude product was purified by column chromatography using 10:1 hexanes/ethyl acetate as eluant. This gave pure racemic 3-(3-fluorophenyl)-3-(4-methoxyphenyl)acrylic acid ethyl ester (0.8 g, 88%). This compound was dissolved in ethanol (50 mL) with Pd/C (10% w/w, 450 mg) and then shaken under hydrogen in a parr shaker overnight. Insolubles were filtered and the solvent was concentrated under vacuum. The crude product was purified by column chromatography on silica gel using 20:1 hexanes/ethyl acetate as eluant. This gave pure 3-(3-fluorophenyl)-3-(4-methoxyphenyl)-propionic acid ethyl ester (0.4 g, 46%) as a colorless oil. $^1$H NMR (400 MHz, CDCl$_3$) 7.26-7.20 (m, 1H); 7.14 (d, J=8.0 Hz, 2H); 7.01 (d, J=8.0 Hz, 1H); 6.92-6.84 (m, 2H), 6.83 (d, J=8.0 Hz, 2H); 4.49 (t, J=7.8 Hz, 1H); 4.04 (q, J=8.0 Hz, 2H), 3.77 (s, 3H), 2.99 (d, J=7.8 Hz, 2H), 1.12 (t, J=8.0 Hz, 3H); MS (ES) m/z 325 (M+Na$^+$). Methyl ether (160 mg, 0.53 mmol in dichloromethane (6 mL) at −78° C. was treated with boron tribromide (1.0 M in dichloromethane, 0.8 mL, 0.8 mmol). The mixture was stirred at 0° C. for 2 h and then at room temperature overnight. Saturated sodium bicarbonate was added to the cooled mixture. The mixture was extracted with ethyl acetate thrice. The combined extracts were washed with water and brine, and then dried over sodium sulfate. Solvent was then evaporated under reduced pressure and the crude product was purified by chromatography on silica gel using 4:1 hexanes/ethyl acetate. This gave pure 3-(3-fluorophenyl)-3-(4-hydroxyphenyl)propionic acid ethyl ester (132 mg, 87%) as a colorless oil. This compound (22 mg, 0.07 mmol) in DMF (0.6 mL) was treated with cesium fluoride (30 mg, 0.2 mmol) and n-butyl iodide (15 mg, 0.08 mmol). The reaction mixture was stirred at room temperature overnight. Insolubles were removed by filtration and the solvent was evaporated under reduced pressure. The crude was then purified by chromatography on silica gel using 20:1 hexanes/ethyl acetate as eluant. This gave pure 3-(4-butoxyphenyl)-3-(3-fluorophenyl)propionic acid ethyl ester (18 mg, 78%) as a colorless oil. A solution of the butoxy ether (46 mg, 0.12 mmol) in tetrahydrofuran/methanol/water (4:1:1 v/v/v, 6 mL) was treated with lithium hydroxyde (1 mL, 1 mmol, 1N). The mixture was stirred at room temperature overnight. 1N hydrochloric acid solution was added and the mixture was extracted three times with ethyl acetate. The combined extracts were washed with brine and dried over sodium sulfate. Solvent was evaporated under reduced pressure and the crude was purified by chromatography on silica gel using 20:1 methylene chloride/methanol as eluant. This gave pure 3-(4-butoxyphenyl)-3-(3-fluorophenyl)-propionic acid (25 mg, 58%) as a white solid. $^1$H NMR (400 MHz, CDCl$_3$) δ 7.26-7.20 (m, 1H); 7.11 (d, J=8.0 Hz, 2H); 7.00 (d, J=8.0 Hz, 1H); 6.90-6.83 (m, 2H), 6.82 (d, J=8.0 Hz, 2H); 4.45 (t, J=7.8 Hz, 1H); 3.92 (t, J=8.0 Hz, 2H), 3.02 (d, J=7.8 Hz, 2H), 1.78-1.69 (m, 2H); 1.52-1.40 (m, 2H), 0.96 (t, J=8.0 Hz, 3H); MS (ES) m/z 339 (M+Na$^+$).

Example 3

Preparation of Substituted Octanoyl Phenyl Compounds

Compound XVII, Sodium (RS)-2-[4-octanoylphenoxy]decanoate.

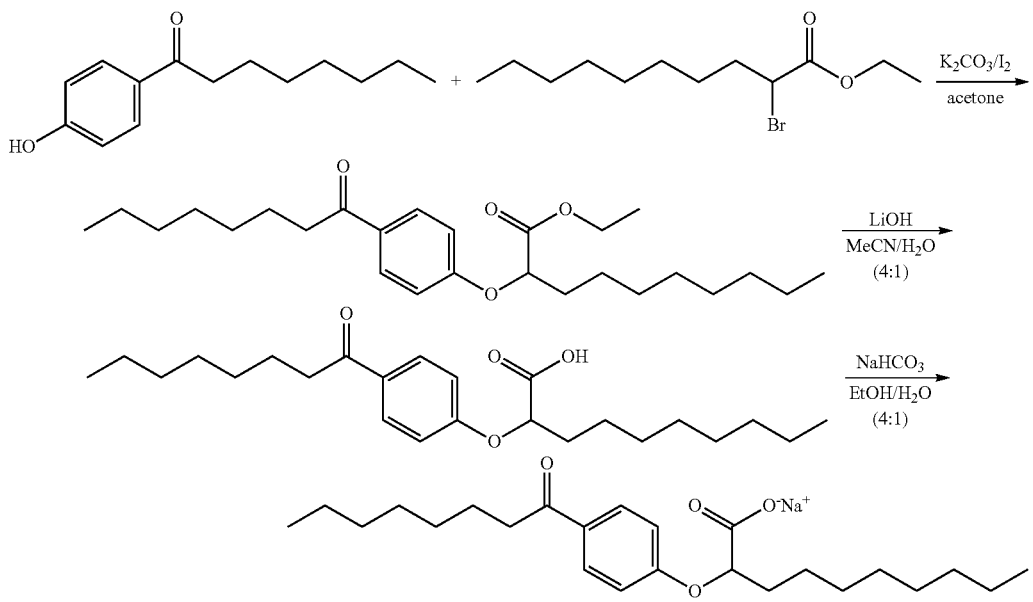

A mixture of 1-[4-hydroxyphenyl]octan-1-one (10.0 g, 45.4 mmol), K$_2$CO$_3$ (9.4 g, 68.1 mmol) and iodine (1.5 g, 9.1 mmol) in acetone (100 mL), was treated with ethyl 2-bromodecanoate (13.9 g, 49.9 mmol), and the reaction was stirred at room temperature, under nitrogen, overnight. Solvent was evaporated in vacuo, and the residue partitioned between ethyl acetate and water. The organic phase was washed with saturated sodium chloride, dried over magnesium sulfate, filtered and evaporated in vacuo. The crude material was purified on a silica gel pad, eluting with 5% ethyl acetate/hexane to give ethyl (RS)-2-[4-octanoylphenoxy]decanoate (11.9 g, 62%) as a colourless oil. $^1$H NMR (400 MHz, CDCl$_3$): δ 7.92 (d, J=9.0 Hz, 2H), 6.89 (d, J=9.0 Hz, 2H), 4.66 (dd, J=7.5, 5.2 Hz, 1H), 4.21 (q, J=7.0 Hz, 2H), 2.89 (t, J=7.4 Hz, 2H), 1.90-2.03 (m, 2H), 1.66-1.74 (m, 2H), 1.43-1.56 (m, 2H), 1.24-1.37 (m, 18H), 1.24 (t, J=7.2 Hz, 2H), 0.85-0.89 (m, 6H). A solution of ethyl ester (11.9 g, 28.3 mmol) in a mixture of tetrahydrofuran (360 mL), methanol (90 mL) and water (90 mL), was treated with lithium hydroxide monohydrate (5.9 g, 141.5 mmol), and the mixture was stirred at room temperature for 20 h. A second portion of lithium hydroxide monohydrate (2.3 g, 54.8 mmol) was added and the reaction was stirred at room temperature for an additional 3 h. The reaction mixture was concentrated in vacuo and the residue partitioned between ethyl acetate and water. The organic phase was washed with saturated sodium chloride, dried over magnesium sulfate, filtered and evaporated in vacuo, to give the crude product. Purification on a silica gel pad, eluting with 40% ethyl acetate/hexane; and recrystallization from hexanes gave (RS)-2-[4-octanoylphenoxy]decanoic acid (9.46 g, 86%) as a white solid. m.p. 45-47° C.; $^1$H NMR (400 MHz, CDCl$_3$): δ 7.93 (d, J=9.0 Hz, 2H), 6.91 (d, J=9.0 Hz, 2H), 4.72 (dd, J=6.8, 5.7 Hz, 1H), 2.90 (t, J=7.4 Hz, 2H), 1.98-2.04 (m, 2H), 1.67-1.74 (m, 2H), 1.46-1.59 (m, 2H), 1.24-1.37 (m, 18H), 0.87 (t, J=6.9 Hz, 3H), 0.88 (t, J=6.9 Hz, 3H). A solution of the acid (9.4 g, 24.1 mmol) in ethanol (200 mL) was treated with a solution of sodium bicarbonate (2.0 g, 24.1 mmol) in water (50 mL), and the reaction was stirred at room temperature for 5 h. Solvents were concentrated in vacuo, and the solution was diluted with water (950 mL), filtered (0.2 μm), and lyophilised to give sodium (RS)-2-[4-octanoylphenoxy]decanoate as a white solid (8.8 g, 88%). mp 275-280° C.; $^1$H NMR (400 MHz, CD$_3$OD): δ 7.96 (d, J =9.0 Hz, 2H), 6.97 (d, J =9.0 Hz, 2H), 4.72 (dd, J =6.2, 5.9 Hz, 1H), 2.95 (t, J =7.4 Hz, 2H), 1.94-1.99 (m, 2H), 1.64-1.72 (m, 2H), 1.49-1.57 (m, 2H), 1.28-1.40 (m, 18H), 0.90 (t, J =6.9 Hz, 3H), 0.89 (t, J=6.9 Hz, 3H); $^{13}$C NMR (101 MHz, CD$_3$OD): δ 200.72, 177.83, 163.37, 130.20, 129.61, 114.70, 79.55, 37.94, 33.19, 31.87, 31.76, 29.45, 29.38, 29.24, 29.22, 29.16, 25.74, 24.85, 22.57, 22.52, 13.29, 13.28; LRMS (ESI): m/z 391 (M−Na$^+$+ 2H$^+$); HPLC: 6 min.

Resolution of the enantiomers of Compound I.

Sodium Salts of (R)- & (S)-2-[4-Octanoylphenoxy]decanoate

1) Formation and separation of (S)-lactamide esters: A solution of (RS)-2-[4-octanoylphenoxy]decanoic acid (0.9 g, 2.4 mL) in dichloromethane (20 mL) was treated dropwise with oxalyl chloride (0.26 mL, 3.1 mmol), and the reaction was stirred at room temperature for 1 h. Triethylamine (0.51 mL, 3.7 mmol) was added, followed by (S)-lactamide (0.5 g, 6.1 mmol), and the reaction was stirred at room temperature for 20 h. The solution was then diluted with ethyl acetate (100 mL), and washed with 1M aqueous HCl (100 mL), water (100 mL) and saturated aqueous sodium chloride (50 mL), then dried over sodium sulphate and evaporated in vacuo. The two diastereomers were separated on a Biotage™ 40 L column (silica), eluted with diethyl ether/hexane 1:4 to 1:1, then with ethyl acetate/hexane 1:4 to 1:1. This gave the separate pure diastereomers.

First diastereomer (0.51 g, 45%) as a white, waxy solid:
hu 1H NMR (400 MHz, CDCl$_3$): δ 7.93 (d, J=9.0 Hz, 2H), 6.91 (d, J=8.8 Hz, 2H), 5.68 (br s, 1H), 5.54 (br s, 1H), 5.22 (q, J=6.8 Hz, 1H), 4.77 (dd, J=7.3, 5.2 Hz, 1H), 2.88 (t, J=7.5 Hz, 2H), 1.92-2.08 (m, 2H), 1.69, (tt, J=7.3, 7.3 Hz, 2H), 1.46-

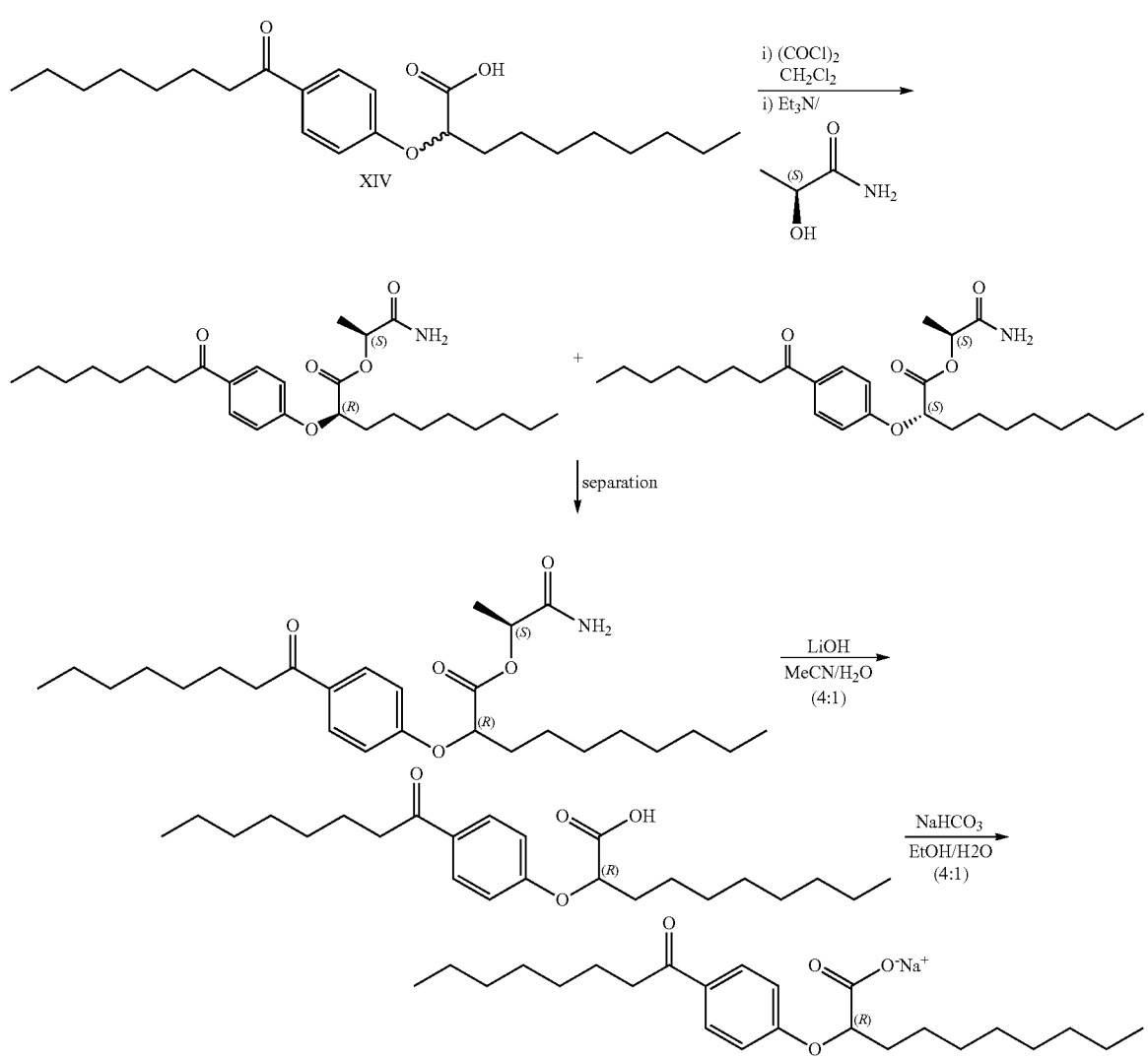

The same procedure was repeated for the (S) isomer 1.56 (m, 2H), 1.47, (d, J=6.8 Hz, 3H), 1.23-1.38 (m, 18H), 0.86 (t, J=6.6 Hz, 6H); $^{13}$C NMR (101 MHz, CDCl$_3$): δ 199.15, 172.34, 170.09, 161.35, 131.47, 130.82, 114.56, 76.70, 71.16, 38.59, 32.90, 32.00, 31.93, 29.57, 29.52, 29.35 (3C), 25.26, 24.68, 22.84 (2C), 17.85, 14.29 (2C).

Second diastereomer (0.5 g, 42%) as a viscous, colourless oil:
$^1$H NMR (400 MHz, CDCl$_3$): δ 7.90 (d, J=9.0 Hz, 2H), 6.91 (d, J=9.0 Hz, 2H), 6.25 (br s, 1H), 6.15 (br s, 1H), 5.20 (q, J=6.9 Hz, 1H), 4.79 (dd, J=6.6, 5.9 Hz, 1H), 2.88 (t, J=7.5 Hz, 2H), 1.95-2.01 (m, 2H), 1.68, (tt, J=7.3, 7.3 Hz, 2H), 1.47-1.55 (m, 2H), 1.39, (d, J=6.8 Hz, 3H), 1.22-1.37 (m, 18H), 0.86 (t, J=6.8 Hz, 6H); $^{13}$C NMR (101 MHz, CDCl$_3$): δ 199.43, 172.71, 170.29, 161.52, 131.31, 130.60, 114.84, 76.48, 71.13, 38.59, 32.80, 32.00, 31.93, 29.58, 29.53, 29.36 (3C), 25.36, 24.76, 22.84, 17.69, 14.29 (2C).

2) Conversion of Diastereomers to the Corresponding Sodium Salt:

General Procedure:

A solution of diastereomeric ester (1.7 g, 3.7 mmol) in acetonitrile (72 mL) was treated with a solution of lithium hydroxide (0.5 g, 18.7 mmol) in water (18 mL), and the reaction was stirred at room temperature for 17 h. The reaction was quenched by addition of 1M aqueous HCl (150 mL), and extracted with ethyl acetate (2×100 mL). Combined extracts were washed with water (150 mL) and saturated sodium chloride (150 mL); then dried over sodium sulfate, filtered and evaporated in vacuo to give the crude acid.

First Enantiomer (Higher R$_f$, Silica Gel):

Purification on a Biotage™ 40 L column (silica), eluted with ethyl acetate/hexane 1:9 to 7:3, gave the purified acid enantiomer as a white solid (1.3 g, 87%). $^1$H NMR (400 MHz, CDCl$_3$): δ 11.50 (s, 1H), 7.92 (d, J=8.8 Hz, 2H), 6.90 (d, J=9.0 Hz, 2H), 4.71 (dd, J=6.4, 5.9 Hz, 1H), 2.89 (t, J=7.4 Hz, 2H), 1.97-2.03 (m, 2H), 1.69, (tt, J=7.1, 7.1 Hz, 2H), 1.45-1.59 (m, 2H), 1.21-1.38 (m, 18H), 0.862 (t, J=7.0 Hz, 3H), 0.859 (t, J=6.8 Hz, 3H); $^{13}$C NMR (101 MHz, CDCl$_3$): δ 200.20, 176.59, 161.76, 131.00, 130.77, 114.83, 76.15, 38.59, 32.80, 32.03, 31.93, 29.59, 29.53, 29.39, 29.37 (2C), 25.38, 24.91, 22.89 (2C), 14.30 (2C). A solution of the acid (1.3 g, 3.2 mmol) in ethanol (20 mL) was treated with a solution of sodium bicarbonate (0.3 g, 3.2 mmol) in water (5 mL), and the reaction was stirred at room temperature for 3 days. Solvents were evaporated in vacuo to give the crude salt as a white waxy solid. This material was dissolved in water (130 mL), filtered (0.2 micron; nylon) and lyophilised to give the pure enantiomer as a white solid (1.1 g, 97%). $^1$H NMR (400 MHz, CD$_3$OD): δ 7.91 (d, J=8.6 Hz, 2H), 6.96 (d, J=8.8 Hz, 2H), 4.46 (t, J=6.2 Hz, 1H), 2.92 (t, J=7.3 Hz, 2H), 1.90-1.95 (m, 2H), 1.66, (tt, J=7.2, 7.2 Hz, 2H), 1.44-1.61 (m, 2H), 1.24-1.39 (m, 18H), 0.890 (t, J=6.7 Hz, 3H), 0.882 (t, J=6.7 Hz, 3H); $^{13}$C NMR (101 MHz, CD$_3$OD): δ 200.66, 177.83, 163.37, 130.24, 129.64, 114.73, 79.59, 37.96, 33.20, 31.87, 31.76, 29.46, 29.40, 29.26, 29.22, 29.16, 25.75, 24.86, 22.57, 22.53, 13.32, 13.29; other data to be collected.

Second Enantiomer (Lower R$_f$, Silica Gel):

Purification on a Biotage™ 40L column (silica), eluted with ethyl acetate/hexane 1:9 to 7:3, gave the purified acid enantiomer as a white solid (1.1 g, 87%). $^1$H NMR (400 MHz, CDCl$_3$): δ 11.51 (s, 1H), 7.91 (d, J=9.0 Hz, 2H), 6.90 (d, J=9.0 Hz, 2H), 4.71 (dd, J=6.6, 5.9 Hz, 1H), 2.89 (t, J=7.5 Hz, 2H), 1.97-2.03 (m, 2H), 1.69, (tt, J=7.1, 7.1 Hz, 2H), 1.45-1.58 (m, 2H), 1.21-1.37 (m, 18H), 0.862 (t, J=7.0 Hz, 3H), 0.858 (t, J=7.0 Hz, 3H); $^{13}$C NMR (101 MHz, CDCl$_3$): δ 200.16, 176.47, 161.77, 131.03, 130.76, 114.84, 76.18, 38.58, 32.79, 32.02, 31.93, 29.58, 29.52, 29.37, 29.36 (2C), 25.36, 24.91, 22.84 (2C), 14.35, 14.28. A solution of the acid (1.1 g, 2.7 mmol) in ethanol (16 mL) was treated with a solution of sodium bicarbonate (0.2 g, 2.7 mmol) in water (4 mL), and the reaction was stirred at room temperature for 18 h. Solvent was evaporated in vacuo to give the crude salt as a clear, colourless syrup. This material was dissolved in water (100 mL), filtered (0.2 micron; nylon) and lyophilised to give the pure enantiomer as a white solid (1.1 g, 99%). $^1$H NMR (400 MHz, CD$_3$OD): δ 7.91 (d, J=9.0 Hz, 2H), 6.96 (d, J=9.0 Hz, 2H), 4.46 (t, J=6.2 Hz, 1H), 2.92 (t, J=7.4 Hz, 2H), 1.90-1.95 (m, 2H), 1.66, (tt, J=7.1, 7.1 Hz, 2H), 1.45-1.61 (m, 2H), 1.24-1.39 (m, 18H), 0.890 (t, J=6.8 Hz, 3H), 0.881 (t, J=6.9 Hz, 3H); $^{13}$C NMR (101 MHz, CD$_3$OD): δ 200.65, 177.82, 163.37, 130.20, 129.65, 114.74, 79.58, 37.96, 33.19, 31.87, 31.76, 29.46, 29.40, 29.26, 29.22, 29.16, 25.75, 24.86, 22.57, 22.53, 13.32, 13.29.

Compound XVIII, Sodium 3-octanoylbenzoate.

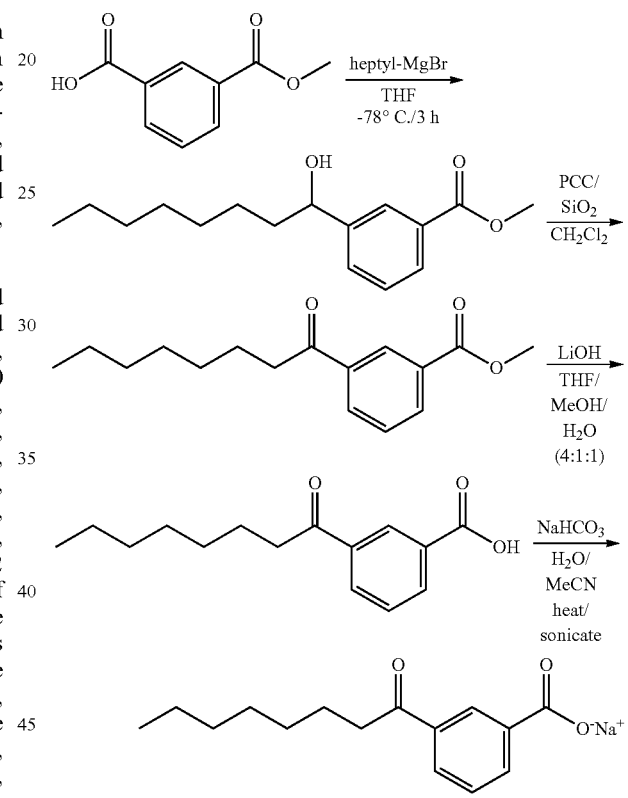

A solution of methyl 3-formylbenzoate (2.0 g, 12.2 mmol) in tetrahydrofuran (40 mL) was cooled to −78° C. under nitrogen. A solution of n-heptylmagnesium bromide in tetrahydrofuran (1 M; 12.2 mL, 12.2 mmol) was added dropwise over 30 min, and the reaction was stirred at −78° C. for 3 h. The reaction was quenched by addition of aqueous hydrochloric acid (1 M), and the mixture was extracted (×3) with ethyl acetate. Extracts were combined, dried over sodium sulfate, filtered and evaporated in vacuo. The crude material was purified on a Biotage™ 40 M column (silica), eluting with 10% ethyl acetate/hexane to give methyl (RS)-3-[1-hydroxyoctyl]benzoate (2.2 g, 69%) as a colourless oil. $^1$H NMR (400 MHz, CDCl$_3$): δ 7.98 (s, 1H), 7.91 (d, J=7.8 Hz, 1H), 7.53 (d, J=7.8 Hz, 1H), 7.39 (dd, J=7.8, 7.8 Hz, 1H), 4.65-4.71 (s, 1H), 3.89 (s, 3H), 2.33 (d, J=3.1 Hz, 1H), 1.62-1.80 (m, 2H), 1.18-1.41 (m, 10H), 0.85 (t, J=6.9 Hz, 3H). A solution of the secondary alcohol (2.0 g, 7.5 mmol) in dichloromethane (50 mL) was treated with silica gel (16 g) and pyridinium chlorochromate (3.2 g, 15.0 mmol), and the reaction was stirred at room temperature overnight. The reaction mixture was filtered through silica gel, and the residue was washed with dichloromethane. Combined filtrate and washings were evaporated in vacuo to give methyl 3-octanoylbenzoate (9.5 g, 86%). $^1$H NMR (400 MHz, CDCl$_3$): δ 8.58-8.59 (m, 1H), 8.20-8.23 (m, 1H), 8.14-8.17 (m, 1H), 7.53-7.57 (m, 1H), 3.95 (s, 3H), 3.00 (t, J=7.3 Hz, 2H), 1.74 (tt, J=7.3, 7.3 Hz, 2H), 1.24-1.40 (m, 8H), 0.88 (t, J=6.9 Hz, 3H). A solution of the methyl ester (1.0 g, 3.8 mmol) in tetrahydrofuran (30 mL), was treated with a solution of lithium hydroxide monohydrate (800 mg, 19.1 mmol) in water (7 mL). Methanol (7 mL) was then added, and the mixture was stirred at room temperature for 24 h. The reaction mixture was treated with aqueous HCl (1 M) until the pH was below 5, and was then extracted with ethyl acetate (×3). Organic extracts were combined, washed with saturated aqueous sodium chloride, dried over sodium sulfate, filtered and evaporated in vacuo, to give 3-octanoylbenzoic acid (919 mg, 97%). $^1$H NMR (400 MHz, CD$_3$OD): δ 8.59 (dd, J=1.7, 1.2 Hz, 1H), 8.18-8.24 (m, 2H), 7.61 (ddd, J=7.8, 7.8, 0.4 Hz, 1H), 3.05 (t, J=7.3 Hz, 2H), 1.71 (tt, J=7.3, 7.3 Hz, 2H), 1.27-1.41 (m, 8H), 0.90 (t, J=7.0 Hz, 3H). A mixture of the acid (919 mg, 3.7 mmol) and sodium bicarbonate (311 mg, 3.7 mmol) was treated with water (20 mL), and the reaction heated with sonication and stirred until most of the solids dissolved. Acetonitrile was added and the mixture was filtered (0.45 μm), and lyophilised to give sodium 3-octanoylbenzoate as a white solid (1.0 g, 100%). $^1$H NMR (400 MHz, D$_2$O): δ 8.14 (s, 1H), 7.81 (d, J=7.8 Hz, 1H), 7.61 (d, J=8.0 Hz, 1H), 7.18 (dd, J=8.0, 7.8 Hz, 1H), 2.69 (t, J=6.8 Hz, 2H), 1.33 (tt, J=7.0, 7.0 Hz, 2H), 0.88-1.03 (m, 8H), 0.54 (t, J=7.0 Hz, 3H). $^{13}$C NMR (101 MHz, D$_2$O): δ 203.93, 173.62, 137.25, 136.27, 133.92, 130.27, 128.59, 128.48, 38.58, 31.41, 28.82, 28.79, 24.25, 22.32, 13.60; LRMS (ESI): m/z 249 (M−Na$^+$+2H$^+$); HPLC: 4 min.

Compound XIX, Sodium (RS)-5-octanoylindane-2-carboxylate.

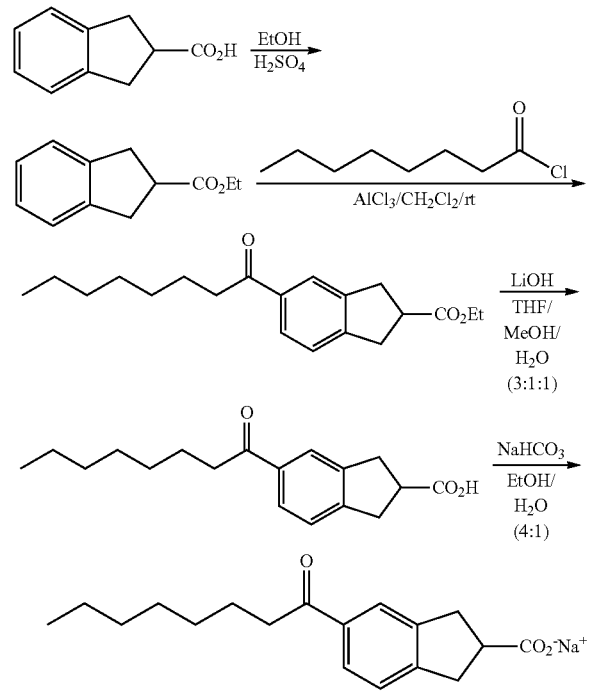

A solution of indane-2-carboxylic acid (504 mg, 3.1 mmol) and sulphuric acid (2 mL) in dry ethanol, was heated at 75° C. for 3 days. The solution was concentrated in vacuo, and then partitioned between dichloromethane and water. The pH of the aqueous layer was adjusted to 13-14 with aqueous sodium hydroxide (5 M), and the layers were separated. The aqueous phase was diluted with saturated sodium chloride, and extracted (2×) with dichloromethane. Combined organic extracts were washed with saturated sodium chloride, dried over sodium sulfate, filtered and evaporated in vacuo, to give the crude product. Purification on a Biotage™ 25S column (silica), eluting with 3% ethyl acetate/hexane, gave ethyl indane-2-carboxylate (526 mg, 96%). $^1$H NMR (400 MHz, CDCl$_3$): δ 7.22-7.26 (m, 2H), 7.17-7.20 (m, 2H), 4.21 (q, J=7.0 Hz, 2H), 3.19-3.39 (m, 5H), 1.31 (t, J=7.0 Hz, 3H). A mixture of ethyl indane-2-carboxylate (100 mg, 0.5 mmol) and aluminium chloride (164 mg, 1.2 mmol) in dichloromethane (4 mL), was treated with octanoyl chloride (0.1 mL, 0.5 mmol) at room temperature, and the reaction was stirred at ambient temperature overnight. The reaction mixture was poured onto a mixture of ice and aqueous. Hydrochloric acid (1 M), and extracted (3×) with dichloromethane. Combined organic extracts were dried over magnesium sulfate, filtered and evaporated in vacuo. The crude material was purified on a Biotage™ column (silica), eluting with 5% ethyl acetate/hexane, to give ethyl (RS)-5-octanoyl-indane-2-carboxylate (110 mg, 65%). $^1$H NMR (400 MHz, CDCl$_3$): δ 7.69-7.77 (m, 2H), 7.29-7.32 (m, 1H), 4.07-4.17 (m, 2H), 3.15-3.36 (m, 5H), 2.84-2.90 (m, 2H), 1.62-1.70 (m, 2H), 1.19-1.34 (m, 8H), 0.80-0.87 (m, 3H). A suspension of the ethyl ester (82 mg, 0.3 mmol) in a mixture of tetrahydrofuran (3 mL), methanol (1 mL) and water (1 mL), was treated with lithium hydroxide (43 mg, 1.8 mmol), and the mixture was stirred at room temperature overnight. The reaction mixture was concentrated in vacuo and the residue diluted with water. The pH was adjusted to pH 4 with aqueous HCl (1 M), and the mixture was extracted (3×) with ethyl acetate. Combined organic extracts were dried over magnesium sulfate, filtered and evaporated in vacuo, to give the crude product. Purification on a Biotage™ 12 M column (silica), eluting with 2% ethyl acetate/hexane, gave (RS)-5-octanoyl-indane-2-carboxylic acid (60 mg, 80%). $^1$H NMR (400 MHz, CD$_3$OD): δ 7.80 (s, 1H), 7.78 (dd, J=7.8, 1.4 Hz, 1H), 7.30 (d, J=7.8 Hz, 1H), 3.36 (tt, J=8.2, 8.2 Hz, 1H), 3.24 (d, J=8.2 Hz, 4H), 2.96 (t, J=7.4 Hz, 2H), 1.67 (tt, J=7.2, 7.2 Hz, 2H), 1.26-1.39 (m, 8H), 0.89 (t, J=6.9 Hz, 3H). A solution of the acid (60 mg, 0.2 mmol) in ethanol (4 mL) and water (1 mL) was treated with sodium bicarbonate (18 mg, 0.2 mmol), and the reaction was stirred at room temperature overnight. Solvents were concentrated in vacuo, and the solution was diluted with water, filtered (20 μm), and lyophilised to give sodium (RS)-5-octanoyl-indane-2-carboxylate as a white solid (54 mg, 87%). $^1$H NMR (400 MHz, CD$_3$OD): δ 7.91 (s, 1H), 7.76 (dd, J=7.8, 1.6 Hz, 1H), 7.28 (d, J=7.8 Hz, 1H), 3.16-3.25 (m, 5H), 2.97 (t, J=7.3 Hz, 2H), 1.68 (tt, J=7.3, 7.3 Hz, 2H), 1.28-1.40 (m, 8H), 0.90 (t, J=7.0 Hz, 3H); LRMS (ESI): m/z 289 (M−Na$^+$+2H$^+$); HPLC: 5 min.

Compound XXIV: Sodium (RS)-2-[4-Octanoylphenoxy]octanoate

1-[4-Hydroxyphenyl]-1-octanone (440 mg, 2.0 mmol) and ethyl (RS)-2-bromooctanoate (552 mg, 2.2 mmol) were reacted according to the procedure used for the preparation of I to give Ethyl (RS)-2-[4-Octanoylphenoxy]octanoate (605 mg, 78%). $^1$H NMR (400 MHz, CDCl$_3$): δ 7.91 (d, J=9.0 Hz, 2H), 6.88 (d, J=9.0 Hz, 2H), 4.66 (dd, J=5.1, 7.4 Hz, 1H), 4.20 (q, J=7.0 Hz, 2H), 2.88 (t, J=7.5 Hz, 2H), 1.88-2.02 (m, 2H), 1.70 (tt, J=7.2, 7.2 Hz, 2H), 1.41-1.56 (m, 2H), 1.25-1.37 (m, 14H), 1.23 (t, J=7.1 Hz, 3H), 0.87 (t, J=7.2 Hz, 3H), 0.86 (t, J=7.2 Hz, 3H); $^{13}$C NMR (101 MHz, CDCl$_3$): δ 199.41, 171.48, 161.81, 131.01, 130.54 (2C), 114.77 (2C), 76.75, 61.62, 38.56, 32.90, 31.94, 31.78, 29.60, 29.38, 29.07, 25.33, 24.80, 22.85, 22.75, 14.39, 14.31, 14.26. The resulting ester (605 mg, 1.6 mmol) was saponified with lithium hydroxide (186 mg, 7.8 mmol) according to the procedure used for the preparation of I to give (RS)-2-[4-Octanoylphenoxy]octanoic Acid (487 mg, 87%). $^1$H NMR (400 MHz, CDCl$_3$): δ 9.70 (br s, 1H), 7.89 (d, J=9.0 Hz, 2H), 6.89 (d, J=9.0 Hz, 2H), 4.69 (dd, J=5.9, 6.6 Hz, 1H), 2.87 (t, J=7.5 Hz, 2H), 1.95-2.01 (m, 2H), 1.67 (tt, J=7.2, 7.2 Hz, 2H), 1.43-1.58 (m, 2H), 1.24-1.37 (m, 14H), 0.851 (t, J=6.8 Hz, 3H), 0.849 (t, J=7.4 Hz, 3H); $^{13}$C NMR (101 MHz, CDCl$_3$): δ 200.38, 176.08, 161.84, 130.85, 130.78 (2C), 114.83 (2C), 76.20, 38.56, 32.79, 31.93, 31.76, 29.57, 29.35, 29.05, 25.34, 24.92, 22.84, 22.74, 14.29, 14.23. The acid (500 mg, 1.4 mmol) was then converted to the sodium salt according to the procedure used for the preparation of I to give Sodium (RS)-2-[4-Octanoylphenoxy]octanoate (404 mg, 76%) as a white solid. mp 165-170° C.; $^1$H NMR (400 MHz, CD$_3$OD): δ 7.91 (d, J=8.8 Hz, 2H), 6.95 (d, J=8.8 Hz, 2H), 4.58 (dd, J=6.1, 6.3 Hz, 1H), 2.91 (t, J=7.3 Hz, 2H), 1.91-1.96 (m, 2H), 1.62-1.69 (m, 2H), 1.44-1.58 (m, 2H), 1.25-1.39 (m, 14H), 0.87-0.90 (m, 6H); $^{13}$C NMR (101 MHz, CD$_3$OD): δ 200.50, 176.40, 162.96, 130.28 (2C), 129.94, 114.71 (2C), 78.38, 38.00, 32.98, 31.79, 31.74, 29.27, 29.20, 29.05, 25.50, 24.79, 22.56, 22.51, 13.36, 13.34; LRMS (ESI): m/z 769 (M$_2$H$^+$), 748 (2M−Na$^+$+2H$^+$), 363 (M−Na$^+$+2H$^+$); HPLC: 3 min.

Compound XXV: Sodium (RS)-2-[4-Butyrylphenoxy]decanoate

1-[4-Hydroxyphenyl]-1-butanone (328 mg, 2.0 mmol) and ethyl (RS)-2-bromodecanoate (614 mg, 2.2 mmol) were reacted according to the procedure used for the preparation of I to give Ethyl (RS)-2-[4-Butyrylphenoxy]decanoate (616 mg, 85%) as a clear, colourless oil. $^1$H NMR (400 MHz, CDCl$_3$): δ 7.88 (d, J=9.0 Hz, 2H), 6.86 (d, J=9.0 Hz, 2H), 4.64 (dd, J=5.7, 6.8 Hz, 1H), 4.17 (q, J=7.2 Hz, 2H), 2.83 (t, J=7.3 Hz, 2H), 1.85-1.99 (m, 2H), 1.65-1.75 (m, 2H), 1.39-1.44 (m, 2H), 1.22-1.34 (m, 10H), 1.20 (t, J=7.2 Hz, 3H), 0.94 (t, J=7.4 Hz, 3H), 0.83 (t, J=7.0 Hz, 3H); $^{13}$C NMR (101 MHz, CDCl$_3$): δ 199.04, 171.39, 161.80, 130.98, 130.48 (2C), 114.74 (2C), 76.68, 61.55, 40.37, 32.85, 32.03, 29.53, 29.37 (2C), 25.33, 22.84, 18.11, 14.34, 14.29, 14.10. The resulting ester (616 mg, 1.70 mmol) was saponified with lithium hydroxide (203 mg, 8.5 mmol) according to the procedure used for the preparation of I to give (RS)-2-[4-Butyrylphenoxy]decanoic Acid (166 mg, 29%). $^1$H NMR (400 MHz, CDCl$_3$): δ 10.06 (br s, 1H), 7.91 (d, J=9.0 Hz, 2H), 6.90 (d, J=9.0 Hz, 2H), 4.70 (dd, J=5.9, 6.4 Hz, 1H), 2.87 (t, J=7.3 Hz, 2H), 1.96-2.02 (m, 2H), 1.68-1.77 (m, 2H), 1.44-1.59 (m, 2H), 1.24-1.37 (m, 10H), 0.97 (t, J=7.4 Hz, 3H), 0.86 (t, J=7.0 Hz, 3H); $^{13}$C NMR (101 MHz, CDCl$_3$): δ 199.95, 176.56, 161.74, 131.03, 130.73 (2C), 114.82 (2C), 76.16, 40.47, 32.79, 32.03, 29.53, 29.39, 29.37, 25.38, 22.86, 18.26, 14.31, 14.12. The acid (166 mg, 0.5 mmol) was then converted to the sodium salt according to the procedure used for the preparation of I to give Sodium (RS)-2-[4-Butyrylphenoxy]decanoate (149 mg, 85%) as a white solid. mp 262-278° C.; $^1$H NMR (400 MHz, CD$_3$OD): δ 7.91 (d, J=9.0 Hz, 2H), 6.96 (d, J=9.0 Hz, 2H), 4.70 (dd, J=6.1, 6.5 Hz, 1H), 2.90 (t, J=7.3 Hz, 2H), 1.88-1.93 (m, 2H), 1.67 (tq, J=7.4, 7.4 Hz, 2H), 1.41-1.57 (m, 2H), 1.20-1.35 (m, 10H), 0.95 (t, J=7.4 Hz, 3H), 0.83 (t, J=6.9 Hz, 3H); $^{13}$C NMR (101 MHz, CD$_3$OD): δ 201.82, 178.07, 163.36, 130.53 (2C), 129.54, 114.83 (2C), 79.46, 39.99, 33.11, 31.80, 29.40, 29.27, 29.15, 25.72, 22.54, 18.30, 14.46, 14.15; LRMS (ESI): m/z 713 (M$_2$H$^+$), 669 (2M−2Na$^+$+3H$^+$), 335 (M−Na$^+$+2H$^+$); HPLC: 3 min.

Compound XXVI: Sodium (RS)-2-[4-Hexanoylphenoxy]decanoate

1-[4-Hydroxyphenyl]-1-hexanone (384 mg, 2.0 mmol) and ethyl (RS)-2-bromodecanoate (614 mg, 2.2 mmol) were reacted according to the procedure used for the preparation of I to give Ethyl (RS)-2-[4-Hexanoylphenoxy]decanoate (628 mg, 80%). $^1$H NMR (400 MHz, CDCl$_3$): δ 7.86 (d, J=9.0 Hz, 2H), 6.84 (d, J=9.0 Hz, 2H), 4.60-4.65 (m, 1H), 4.15 (q, J=7.0 Hz, 2H), 2.83 (t, J=7.3 Hz, 2H), 1.86-1.97 (m, 2H), 1.61-1.70 (m, 2H), 1.38-1.52 (m, 2H), 1.20-1.34 (m, 14H), 1.18 (t, J=7.2 Hz, 3H), 0.78-0.87 (m, 6H); $^{13}$C NMR (101 MHz, CDCl$_3$): δ 199.17, 171.36, 161.78, 130.95, 130.46 (2C), 114.72 (2C), 76.66, 61.51, 38.41, 32.84, 32.00, 31.76, 29.52, 29.35 (2C), 25.31, 24.41, 22.83, 22.74, 14.33, 14.26, 14.14. The resulting ester (628 mg, 1.6 mmol) was saponified with lithium hydroxide (193 mg, 8.0 mmol) according to the procedure used for the preparation of I to give (RS)-2-[4-Hexanoylphenoxy]decanoic Acid (468 mg, 80%). $^1$H NMR (400 MHz, CDCl$_3$): δ 7.93 (d, J=9.0 Hz, 2H), 6.91 (d, J=9.0 Hz, 2H), 5.77 (br s, 1H), 4.70 (dd, J=5.8, 6.6 Hz, 1H), 2.89 (t, J=7.4 Hz, 2H), 1.97-2.03 (m, 2H), 1.67-1.74 (m, 2H), 1.44-1.60 (m, 2H), 1.23-1.37 (m, 14H), 0.90 (t, J=6.8 Hz, 3H), 0.87 (t, J=7.0 Hz, 3H); $^{13}$C NMR (101 MHz, CDCl$_3$): δ 199.76, 176.29, 161.56, 131.20, 130.70 (2C), 114.81 (2C), 76.12, 38.56, 32.78, 32.03, 31.80, 29.53, 29.40, 29.36, 25.36, 24.51, 22.87, 22.76, 14.33, 14.20. The acid (468 mg, 1.3 mmol) was then converted to the sodium salt according to the procedure used for the preparation of I to give Sodium (RS)-2-[4-Hexanoylphenoxy]decanoate (459 mg, 93%) as a white solid. mp 275-280° C.; $^1$H NMR (400 MHz, CD$_3$OD): δ 7.91 (d, J=8.8 Hz, 2H), 6.96 (d, J=8.8 Hz, 2H), 4.44-4.48 (m, 1H), 2.89-2.96 (m, 2H), 1.88-1.96 (m, 2H), 1.63-1.71 (m, 2H), 1.44-1.61 (m, 2H), 1.24-1.38 (m, 14H), 0.84-0.93 (m, 6H); $^{13}$C NMR (101 MHz, CD$_3$OD): δ 200.89, 177.86, 163.36, 130.27 (2C), 129.60, 114.75 (2C), 79.54, 37.94, 33.18, 31.86, 31.49, 29.44, 29.38, 29.21, 25.73, 24.55, 22.58, 22.45, 13.36, 13.23; LRMS (ESI): m/z 769.8 (M$_2$H$^+$), 747.8 (2M−Na$^+$+2H$^+$), 363.2 (M−Na$^+$+2H$^+$); HPLC: 3.min.

Compound XLI: Sodium (RS)-4-Octanoylindane-2-carboxylate

Methyl (RS)-4-octanoyl-2-carboxylate (71 mg, 4%) was isolated as a side product during the preparation of its isomer, methyl (RS)-5-octanoyl-2-carboxylate. $^1$H NMR (400 MHz, CDCl$_3$): δ 7.66 (d, J=7.6 Hz, 1H), 7.35 (d, J=7.4 Hz, 1H), 7.24 (dd, J=7.6, 7.6 Hz, 1H), 3.69 (s, 3H), 3.64 (A of ABX, J=18.0, 9.4 Hz, 1H), 3.48 (B of ABX, J=18.1, 7.3 Hz, 1H), 3.13-3.34 (m, 3H), 2.90 (t, J=7.5 Hz, 2H), 1.68 (tt, J=7.2, 7.2 Hz, 2H), 1.24-1.38 (m, 8H), 0.86 (t, J=6.9 Hz, 3H); $^{13}$C NMR (101 MHz, CDCl$_3$): δ 203.01, 176.79, 144.82, 143.67, 134.73, 129.30, 128.35, 127.83, 52.91, 44.06, 40.82, 38.71, 36.44, 32.73, 30.34, 30.19, 25.36, 23.64, 15.10. The methyl ester (71.0 mg, 0.24 mmol) was saponified according to the standard protocol to give (RS)-4-octanoyl-2-carboxylic acid (66.0 mg, 96%) as an off-white solid. $^1$H NMR (400 MHz, CDCl$_3$): δ 7.69 (d, J=7.6 Hz, 1H), 7.39 (d, J=7.4 Hz, 1H), 7.26 (dd, J=7.6, 7.6 Hz, 1H), 3.67 (A of ABX, J=18.0, 9.0 Hz, 1H), 3.56 (B of ABX, J=18.0, 6.9 Hz, 1H), 3.19-3.39 (m, 3H), 2.93 (t, J=7.4 Hz, 2H), 1.70 (tt, J=7.3, 7.3 Hz, 2H), 1.24-1.38 (m, 8H), 0.88 (t, J=6.9 Hz, 3H). The resulting acid (66.0 mg, 0.23 mmol) was then converted to the sodium salt according to the standard protocol to give sodium (RS)-4-octanoyl-2-carboxylate (70.0 mg, 99%) as an off-white solid. mp 106-110° C.; $^1$H NMR (400 MHz, CD$_3$OD): δ 7.69 (d, J=7.8 Hz, 1H), 7.38 (d, J=7.4 Hz, 1H), 7.24 (dd, J=7.6, 7.6 Hz, 1H), 3.37-3.56 (m, 2H), 3.10-3.21 (m, 3H), 2.95 (t, J=7.3 Hz, 2H), 1.66 (tt, J=7.3, 7.3 Hz, 2H), 1.26-1.39 (m, 8H), 0.89 (t, J=6.8 Hz, 3H); $^{13}$C NMR (101 MHz, CD$_3$OD): δ 203.56, 182.93, 145.34, 143.96, 133.93, 128.26, 126.97, 126.42, 47.62, 39.89, 38.69, 36.70, 31.76, 29.21, 29.17, 24.55, 22.52, 13.28; LRMS (ESI): m/z 577 (2M−2Na$^+$+3H$^+$), 289 (M−Na$^+$+2H$^+$); HPLC: 3.0 min.

Example 4

Effect of Compounds on the In Vitro Production of IL-12 in LPS-Stimulated RAW264.7

The effect of selected compounds on IL-12 production was undertaken in RAW264.7 (macrophage-like) cells. RAW264.7 cells were cultured with 100 ng/mL of LPS in presence or absence of compounds for 21 h in a humidified atmosphere of 95% air-5% carbon dioxide at 37° C. IL-12 concentration in the culture medium was measured using the IL-12 ELISA according to the manufacturer (BD Biosciences) recommendations.

Table 2 shows the effect of representative compounds (0.5 mM, unless otherwise stated) on IL-12 production in the presence of LPS (inflammatory conditions). All compounds induce a significant increase in IL-12 production under inflammatory conditions. Compounds have no effect on IL-12 production in the absence of LPS.

TABLE 2

Effect of representative compounds on IL-12 production in the presence of LPS

| | IL-12 (pg/mL) | Structure |
|---|---|---|
| Control (no LPS) | ≤2 | |
| Control (+ LPS) | ≤10 | |
| Sodium decanoate | 50 | H$_3$C(CH$_2$)$_8$COO$^−$Na$^+$ |
| Compound I | 54 | 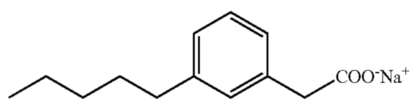 |
| Compound II | 351 | 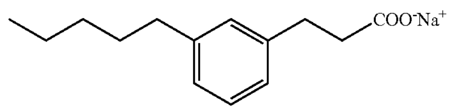 |
| Compound III | 62 | 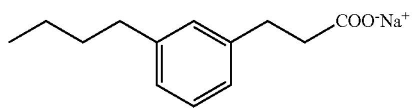 |
| Compound IV | 19 | 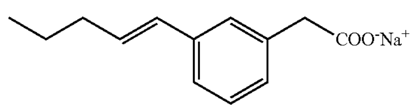 |
| Compound VI | 53 | 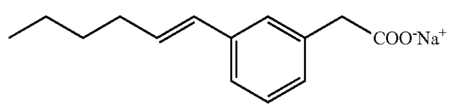 |
| Compound VII | 59 (at 0.25 mM) | 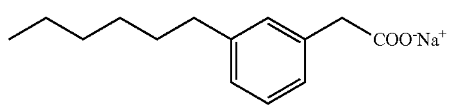 |
| Compound VIII | 17 | 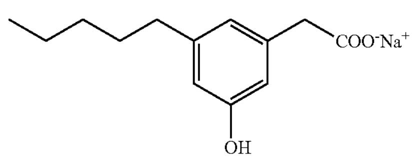 |
| Compound IX | 20 | 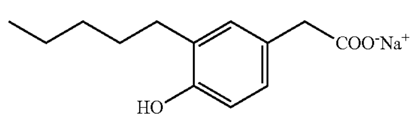 |
| Compound XI | 78 | 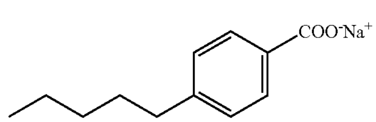 |

TABLE 2-continued

Effect of representative compounds on IL-12 production in the presence of LPS

| | IL-12 (pg/mL) | Structure |
| --- | --- | --- |
| Compound XIII | 18 (at 0.125 mM) | 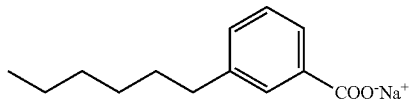 |
| Compound XV | 37 | 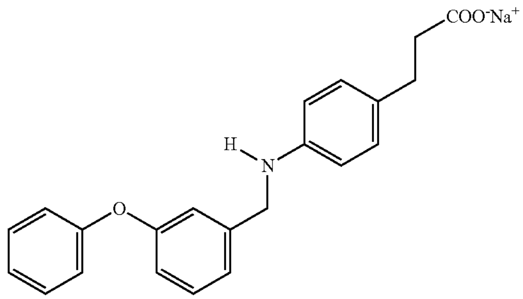 |
| Compound XVII | 209 (at 0.05 mM) | 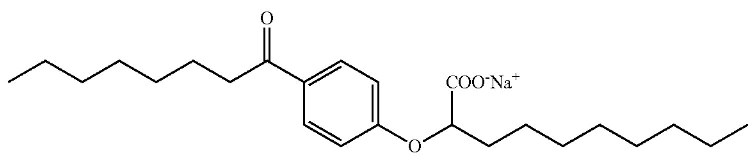 |
| Compound XVIII | 1099 | 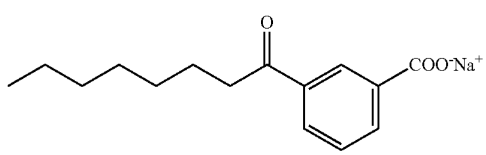 |
| Compound XIX | 53 (at 0.05 mM) | 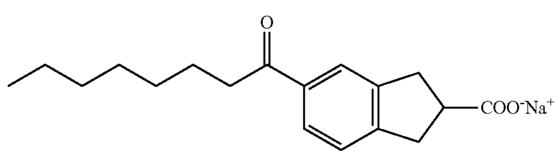 |
| Compound XXIV | 12 (at 0.02 mM) | 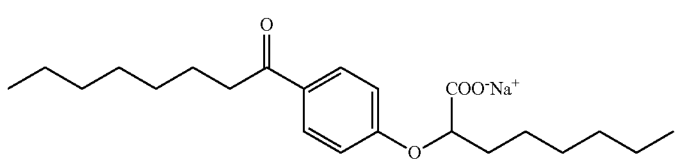 |
| Compound XXV | 73 (at 0.04 mM) | 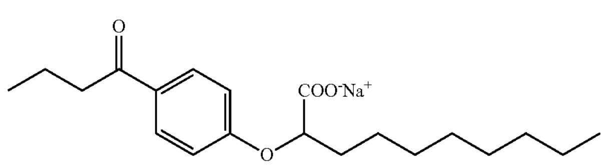 |
| Compound XXVI | 54 (at 0.02 mM) | 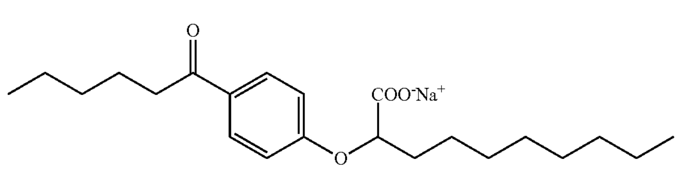 |

TABLE 2-continued

Effect of representative compounds on IL-12 production in the presence of LPS

| | IL-12 (pg/mL) | Structure |
|---|---|---|
| Compound XLI | 25 (at 0.1 mM) | (structure with indane-COO⁻Na⁺ and alkyl ketone chain) |

As an additional example, the effect of Compound XVII on IL-12 production under non-inflammatory and inflammatory conditions is shown in FIG. 1.

These results demonstrate that compounds of Formula I, Formula I.1, Formula I.2, Formula IA, Formula IB, Formula IC and Formula II, in the presence of LPS (inflammatory conditions) induce the production of IL-12. The ability to stimulate the production of IL-12 means that compounds of the present invention may be useful for treating cancer since the resultant IL-12 may i) display a significant and direct antitumor activity and ii) display a significant indirect antitumor activity by stimulation of cytolytic immune cell subsets. This is supported by references hereinabove (see Section C—IL-12 and inflammation).

Example 5

In Vitro Inhibition of CTGF Production in TGF-β Stimulated NHDF or Mesangial Cells The effect of selected compounds on CTGF production was undertaken in normal human dermal fibroblast (NHDF) or human mesangial cells. Cells were cultured in DMEM (0.5% FBS) with or without 10 ng/mL of TGF-β for 48 h in a humidified atmosphere of 95% air-5% carbon dioxide at 37° C. CTGF measurement in the culture medium was measured using the CTGF ELISA according to the manufacturer (Prepotech) recommendations. Results are shown in Table 3.

TABLE 3

Effect of selected representative compounds on the inhibition of TGF-induced CTGF production in NHDF.

| | Concentration (μM) | CTGF Inhibition (%) |
|---|---|---|
| Sodium decanoate | 500 | 51 |
| Compound I | 200 | 54 |
| Compound II | 100 | 38 |
| Compound III | 500 | 46 |
| Compound IV | 500 | 34 |
| Compound VIII | 200 | 47 |
| Compound XI | 500 | 28 |
| Compound XIII | 125 | 29 |
| Compound XV | 20 | 22 |
| Compound XVII | 7.5 | 40 |
| Compound XVIII | 200 | 49 |
| Compound XIX | 63 | 45 |

Figure 2:
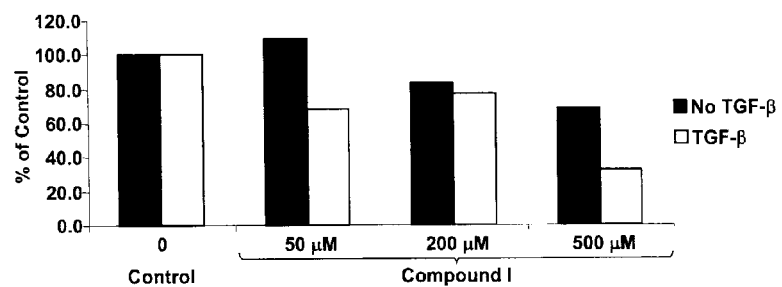
FIG. 2 is a bar graph showing effects of Compound I on inhibition of TGF-induced CTGF production in human mesangial cells in vitro.

Another example of Compound I on inhibition of TGF-induced CTGF production in human mesangial cells is demonstrated in FIG. 2. Compound I induces a significant ($p<0.05$) inhibition of CTGF production.

These results demonstrate that compounds of Formula I, Formula I.1, Formula I.2, Formula IA, Formula IB, Formula IC and Formula II inhibit the production of CTGF. The ability to inhibit the production of CTGF means that compounds of the present invention may be useful for treating cancer since diminished production of CTGF may inhibit angiogenesis and epithelial to mesenchymal transition (EMT), and/or inhibit tumor cell migration and subsequent initiation and establishment of secondary tumors or metastasis. This is supported by references hereinabove (see Section C—CTGF and progression of cancers).

Example 6

Antitumor Effect of Compounds on a Primary B16F10 Melanoma Tumor

Female 6-8 week old C57BL/6 mice were injected subcutaneously on day 0 with 50 μL of $3.75 \times 10^4$ viable B16F10 melanoma cells from ATCC (source of cell culture, Dr. I. J. Fidler). On day 14, tumors reached 80 mm and animals were randomized for treatment. Animals were then treated with daily oral administration of saline (negative control) or sodium decanoate (100 mg/kg) or 5 mg/kg doxorubicin (Dox, positive control) on day 4. Mice were sacrificed on day 12. Serial tumor volume was obtained by bi-dimensional diameter measurements with calipers, using the formula $0.4 (a \times b^2)$ where "a" was the major tumor diameter and "b" the minor perpendicular diameter.

Figure 3:
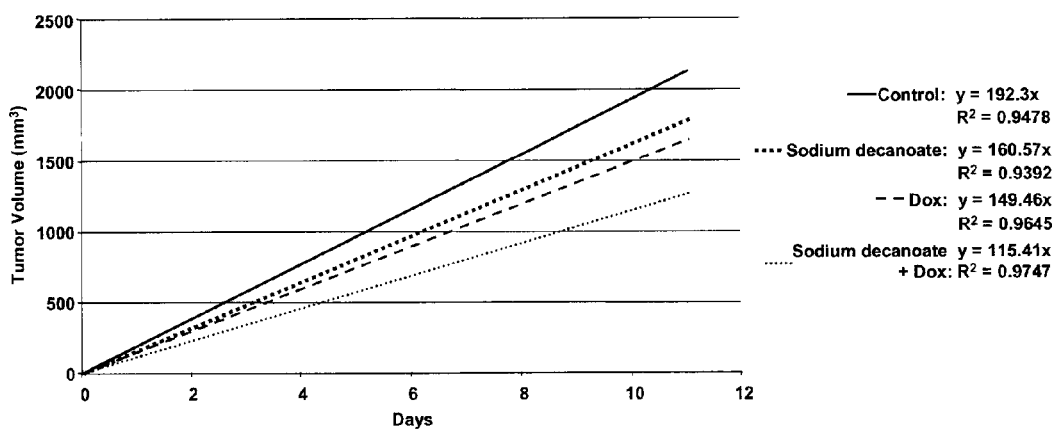
FIG. 3 is a line graph showing antitumor efficacy of sodium decanoate, doxorubicin and combination thereof on B16F10 primary tumor in mice.

FIG. 3 shows the effect of sodium decanoate, subtherapeutic dose of doxorubicin and combination of both compounds on primary tumor B16F10 cells. Sodium decanoate and doxorubicin (subtherapeutic dose) induces weak (around 25%) reduction of primary tumor. Combination of sodium decanoate with doxorubicin displays an additive reduction (approximately 50%) of the tumor volume compared to the control. Sodium decanoate reduces melanoma tumor growth and synergizes with a sub-therapeutic dose of doxorubicin.

Example 7

Antitumor Efficacy Validation of Compound XV in Combination with Gemcitabine in The Panc02 Mouse Pancreatic Cancer Model Syngeneic Panc02 is a pancreatic adenocarcinoma tumor cell line obtained from NCl (0507232). Panc02 cells are positive for Ki-Ras, p53, HerNEU and CDK. Panc02 were grown in RPMI-1640 containing 10% fetal bovine serum. At day 0, 50 μL of $5 \times 10^5$ viable Panc02 cells were injected into the tail of the pancreas in 6- to 8-week old C57BL/6 mice. Mice were then treated every day with oral administration of vehicle (saline, negative control), or Compound XV and with intraperitoneal injection of gemcitabine (50 mg/kg) once a week starting at day 8.

Figure 4:
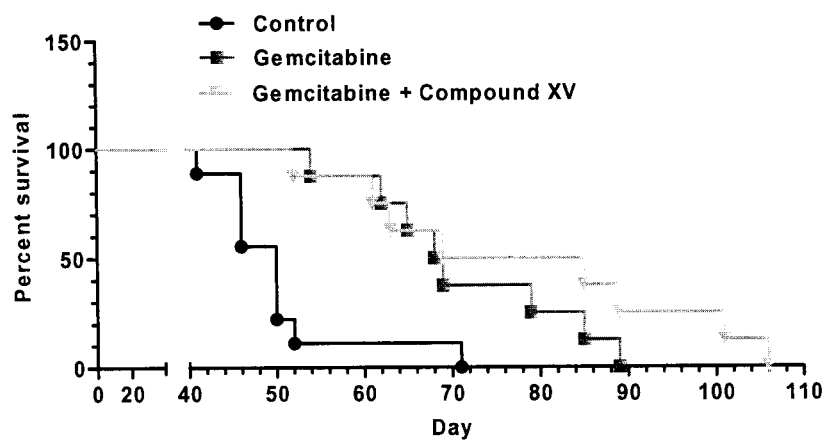
FIG. 4 is a line graph showing antitumor efficacy of gemcitabine with Compound XV on orthotopic Panc02 pancreatic cancer in mice.

FIG. 4 represents the antitumor efficacy of oral administration of Compound XV (200 mg/kg) in combination with gemcitabine and gemcitabine alone (i.p., 50 mg/kg) in pancreatic Panc02 cancer. Gemcitabine induces a significant increase ($p<0.05$) of survival with a median survival of 68.5 days compared to control (50 days). Combination therapy extends survival by 30% for 12 days and augments the median survival to 77 days.

Figure 16:
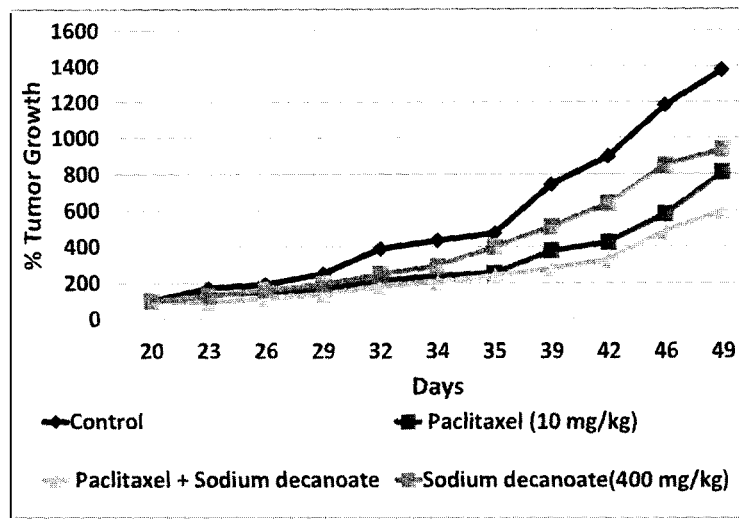
FIG. 16 is a line graph showing antitumor efficacy of sodium decanoate, paclitaxel and combination thereof on pancreatic Panc02 cancer in mice.

FIG. 16 represents the antitumor efficacy of oral administration of sodium decanoate in combination with paclitaxel versus paclitaxel alone (i.p. 10 mg/kg) in pancreatic Panc02 cancer injected subcutaneously to produce localized tumors. Sodium decanoate reduces significantly ($p<0.05$) tumor growth with Treated/Control (T/C) between 60-70% from day 34-39. Paclitaxel induces a significant reduction ($p<0.05$) of tumor growth with a T/C between 40 and 55% from day 29 to 49. Combination of sodium decanoate and paclitaxel induces a significant reduction ($p<0.05$) of tumor growth with T/C less than 40% from day 23 to 49.

Example 8

Antitumor Effect of Compounds on a Primary DA-3 Breast Tumor

The syngeneic tumor DMBA3 (DA-3, breast carcinoma model) arose from a preneoplastic lesion treated with 7,12-dimethylbenzanthracene in female BALB/c mice. DA-3 cells were grown as monolayer cultures in plastic flasks in RPMI-1640 containing 0.1 mM nonessential amino acids, 0.1 µM sodium pyruvate, 2 mM L-glutamine. This was further supplemented with 50 µM 2-mercaptoethanol and 10% fetal bovine serum. The DA-3 tumors were serially passaged in vivo by subcutaneous inoculation of 50 µL ($1\times10^5$) viable tumor cells to produce localized tumors in 6- to 8-week old BALB/c mice. The animals were then serially monitored by manual palpation for evidence of tumor. Mice were treated at day 11 and 18 with cyclophosphamide (100 mg/kg, ip injection) or by oral treatment every day with Compound XV (50 mg/kg). Mice were sacrificed at day 22. Serial tumor volume was obtained by bi-dimensional diameter measurements with calipers, using the formula $0.4\ (a\times b^2)$ where "a" was the major tumor diameter and "b" the minor perpendicular diameter. Tumors were palpable, in general, 7-10 days post-inoculation.

Figure 5:
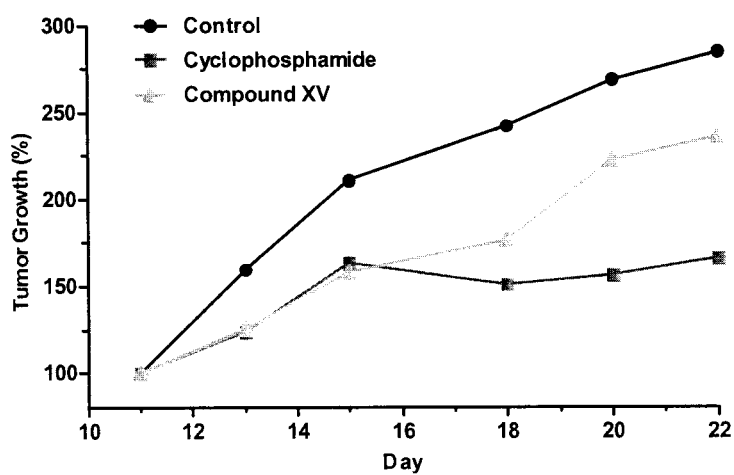
FIG. 5 is a line graph showing the antitumor efficacy of oral administration of Compound XV and cyclophosphamide on DA-3 breast tumor in mice.

FIG. 5 shows the antitumor efficacy of oral administration (50 mg/kg) of Compound XV and cyclophosphamide (100 mg/kg, ip). Compound XV induces a significant ($p<0.03$) inhibition ($p<0.03$) of tumor volume with treatment/control (TIC) of 43% to 74%.

Example 9

Antitumor Effect of Compounds on a Primary P815 Mastocytoma Tumor

The syngeneic tumor P815 is a DBA/2 ($H-2^d$)-derived mastocytoma obtained from ATCC (TIB64). P815 cells were grown in DMEM containing 10% fetal bovine serum. At day 0, 50 µL of $5\times10^5$ viable P815 cells were subcutaneously injected to produce localized tumors in 6- to 8-week old DBA/2 mice. The animals were then serially monitored by manual palpation for evidence of tumor. Mice were then treated every day with oral administration of vehicle (negative control), acetylsalicylic acid (positive control, 50 mg/kg) or sodium decanoate (40-200 mg/kg). Mice were sacrificed around day 23 (depending on the experiment). Serial tumor volume was obtained by bi-dimensional diameter measurements with calipers, using the formula $0.4\ (a\times b^2)$ where "a" was the major tumor diameter and "b" the minor perpendicular diameter. Tumors were palpable, in general, 3-5 days post-inoculation.

Figure 6:
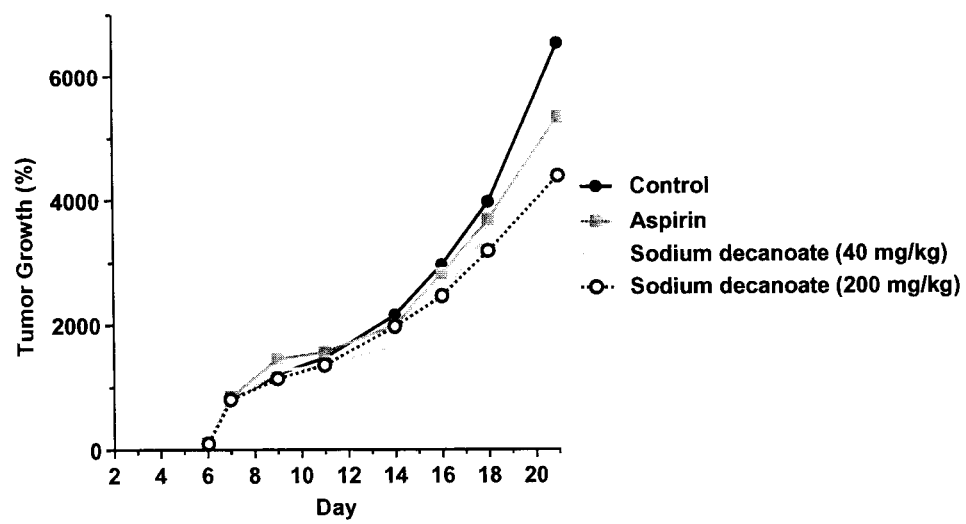
FIG. 6 is a line graph showing the effect of oral administration of sodium decanoate and acetylsalicylic acid (Aspirin™) (positive control) on primary tumor P815 cells in mice.

FIG. 6 shows the effect of oral administration of sodium decanoate and acetylsalicylic acid (positive control) on primary tumor P815 cells. Sodium decanoate induces a significant reduction ($p<0.05$) of P815 (mastocytoma) tumor growth). Furthermore, the activity at these doses was more potent than the gold standard compound, soluble acetylsalicylic acid.

Figure 7:
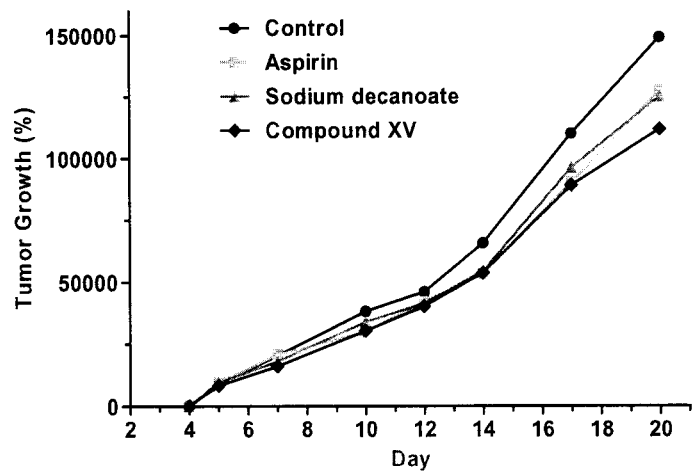
FIG. 7 is a line graph showing antitumor efficacy of sodium decanoate, Compound XV and acetylsalicylic acid (Aspirin™) on P815 primary tumor in mice.
Figure 8:
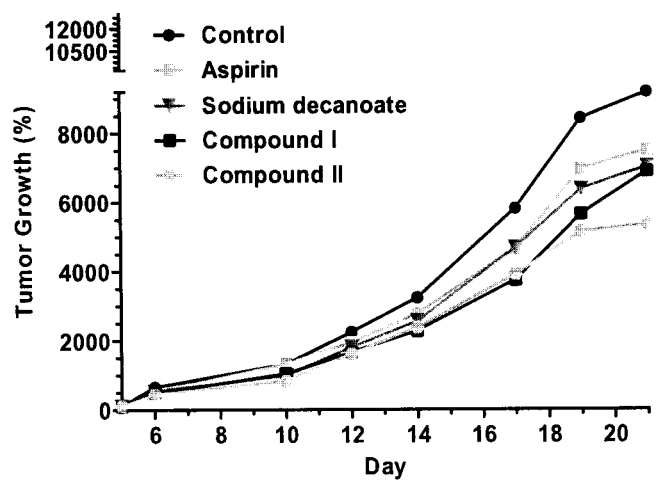
FIG. 8 is a line graph showing antitumor efficacy of sodium decanoate, Compound I, Compound II and acetylsalicylic acid (Aspirin™) on P815 primary tumor in mice.
Figure 17:
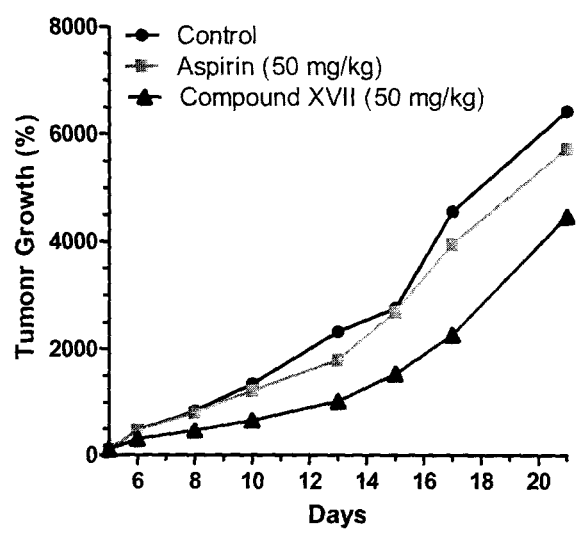
FIG. 17 is a line graph showing antitumor efficacy of Compound XVII and acetylsalicylic acid (Aspirin™) on P815 primary tumor in mice.

Other experiments were undertaken with oral administration of 200 mg/kg of sodium decanoate and Compound XV (FIG. 7); and sodium decanoate, Compounds I and II (FIG. 8). All compounds (at 200 mg/kg) show similar efficacy to the gold standard compound, soluble acetylsalicylic acid and induce a significant reduction ($p<0.05$) of tumor growth. Compound XVII shows better efficacy to the gold standard compound, soluble acetylsalicylic acid and induces a significant reduction ($p<0.05$) of tumor growth (FIG. 17).

Figure 9:
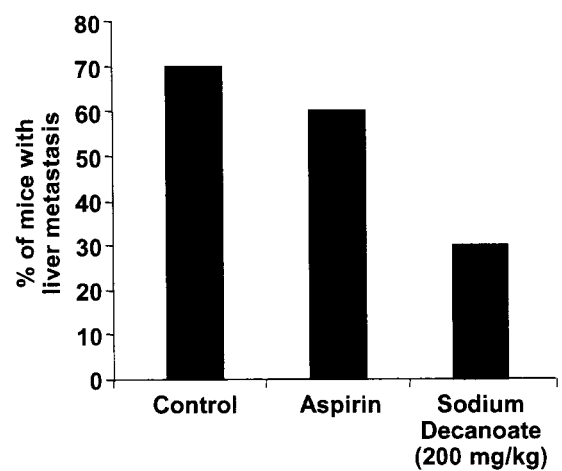
FIG. 9 is a bar graph showing anti-metastasic efficacy of sodium decanoate and acetylsalicylic acid (Aspirin™) on P815 primary tumor in mice.
Figure 10:
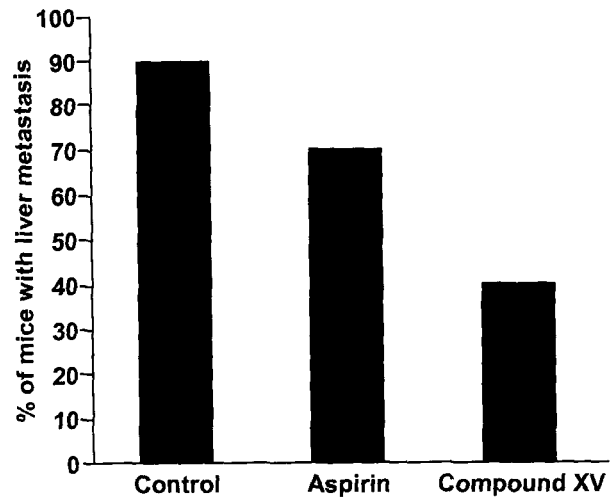
FIG. 10 is a bar graph showing anti-metastasic efficacy of Compound XV and acetylsalicylic acid (Aspirin™) on P815 primary tumor in mice.
Figure 18:
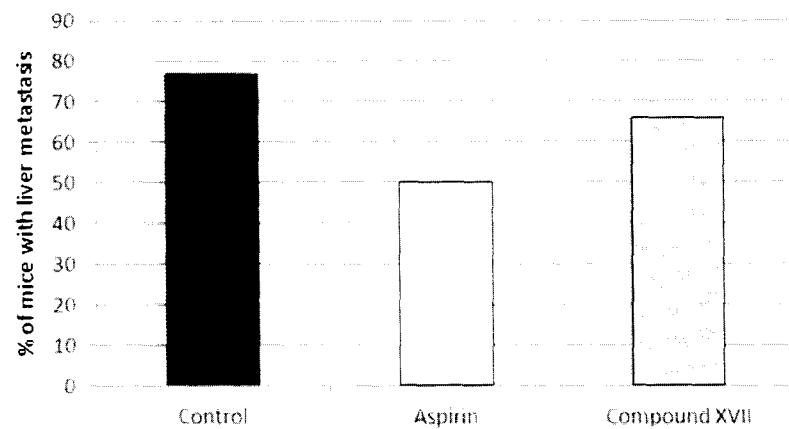
FIG. 18 is a bar graph showing antimetastatic efficacy of Compound XVII and acetylsalicylic acid (Aspirin™) on P815 liver metastasis in mice.

It is known that P815 cells have the capacity to metastasize to the liver. FIG. 9 shows a significant ($p<0.05$) reduction (50%) of mice with liver metastasis upon oral administration of sodium decanoate (200 mg/kg). Compound XV (200 mg/kg) also displays a significant ($p<0.05$) reduction (50%), of mice with liver metastasis. (FIG. 10). In another experiment, Compound XVII (50 mg/kg) reduces by approximately 20% the number of mice with liver metastasis (FIG. 18).

Example 10

Antitumor Effect of Compounds on an LL/2 Lung Tumor

The syngeneic tumor LL/2 is a lung tumor cell line obtained from ATCC(CRL-1642). LL/2 cells were grown in DMEM containing 10% fetal bovine serum. At day 0, 50 µL of $3\times10^5$ viable LL/2 cells were subcutaneously injected to produce localized tumors in 6- to 8-week old mice. The animals were then serially monitored by manual palpation for evidence of tumor. Mice were then treated every day with oral administration of vehicle (negative control), or sodium decanoate (200 mg/kg) and with intraperitoneal injection of gemcitabine (50 mg/kg) at day 1, 8, 15 and 22. Mice were sacrificed at day 26. Serial tumor volume was obtained by bi-dimensional diameter measurements with calipers, using the formula $0.4\ (a\times b^2)$ where "a" was the major tumor diameter and "b" the minor perpendicular diameter. Tumors were palpable, in general, 3-5 days post-inoculation.

Figure 11:
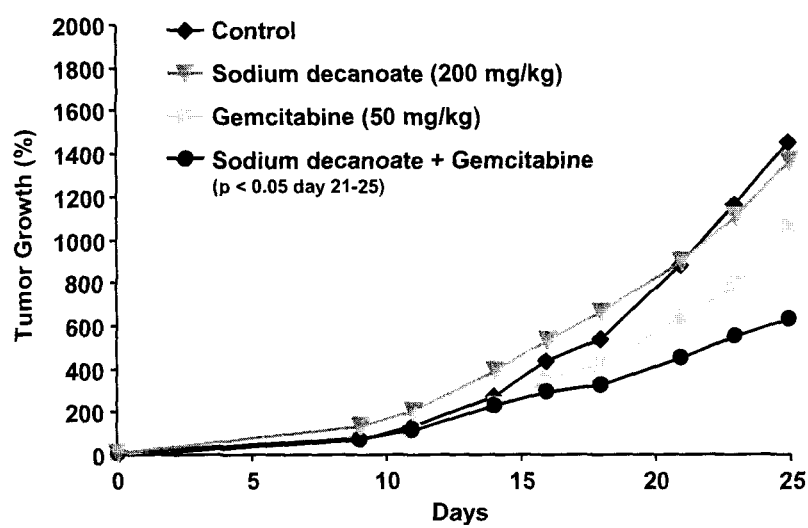
FIG. 11 is a line graph showing antitumor efficacy of sodium decanoate, gemcitabine and combination thereof on LL/2 primary tumor in mice.

FIG. 11 shows the effect of oral administration of sodium decanoate and gemcitabine (positive control) on primary tumor LL/2 cells. Both compounds display weak efficacy. However, when used in combination, sodium decanoate and gemcitabine induce a significant reduction (T/C approximately 40%) of tumor growth from day 16 to day 26.

Example 11

Antitumor Effect of Compounds on a Primary Colon CT-26WT Tumor

The syngeneic tumor CT-26WT (CT-26) is a colon tumor cell line obtained from ATCC (CRL-2638). CT-26 cells were grown in RPMI containing 10% fetal bovine serum. At day 0, 50 µL of $5\times10^6$ viable CT-26 cells were subcutaneously injected to produce localized tumors in 6- to 8-week old mice.

The animals were then serially monitored by manual palpation for evidence of tumor. Mice were then treated every day with oral administration of vehicle (saline, negative control), or sodium decanoate (200 mg/kg) and with intraperitoneal injection of 5-fluorouracil (40 mg/kg) at day 6, 13 and or combination of both compounds. Mice were sacrificed at day 25. Serial tumor volume was obtained by bi-dimensional diameter measurements with calipers, using the formula 0.4 (a×b$^2$) where "a" was the major tumor diameter and "b" the minor perpendicular diameter. Tumors were palpable, in general, 3-5 days post-inoculation.

Figure 12:
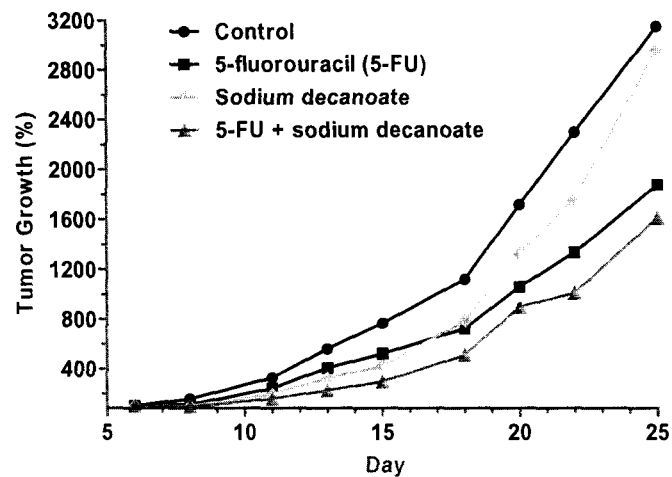
FIG. 12 is a line graph showing the antitumor efficacy of sodium decanoate, 5-fluorouracil and combination thereof on CT-26WT primary tumor in mice.

FIG. 12 shows the effect of oral administration of sodium decanoate and 5-fluorouracil (positive control) on primary tumor CT-26 cells. Both compounds have weak efficacy. However, when used in combination, sodium decanoate and 5-fluorouracil induce a significant reduction (T/C approximately 40%) of tumor growth from day 16 to day 26.

Figure 13:
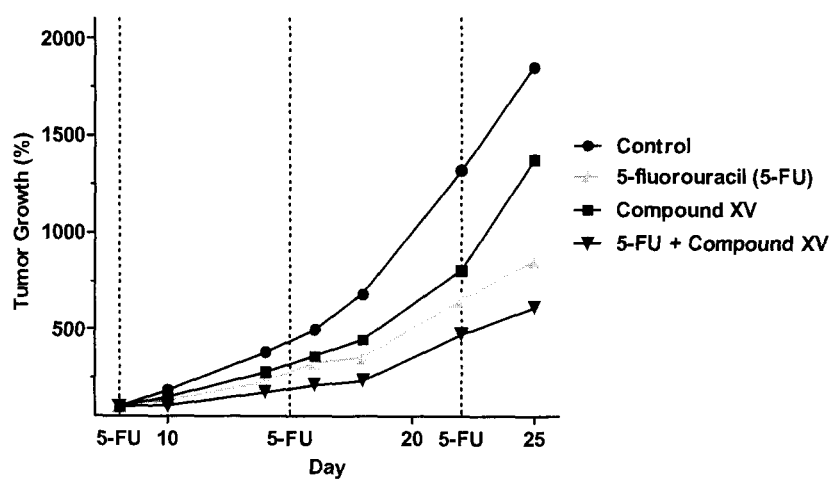
FIG. 13 is a line graph showing antitumor efficacy of Compound XV, 5-fluorouracil and combination thereof on CT-26WT primary tumor in mice.

FIG. 13 shows the effect of oral administration of Compound XV, 5-fluorouracil (positive control) and combination of both compounds on primary tumor CT-26 cells. Compound XV has weak efficacy (T/C=52% to 73%). 5-fluorouracil induces a significant reduction (p≤0.02, T/C=52% to 73%). However, when used in combination, Compound XV and 5-fluorouracil induce a significant (p≤0.01) reduction (T/C of 4% to 31%) in tumor growth from day 16 to day 26.

Example 12

Antitumor Effect of Compounds on Xenograft Human Prostate PC-3 Tumor

The xenogenic human prostate tumor PC-3 was obtained from ATCC(CRL1435). PC-3 cells were grown in RPMI-1640 containing 10% fetal bovine serum. At day 0, 50 µL of viable PC-3 (1.5 to 2×10$^6$) cells were subcutaneously injected to produce localized tumors in 6- to 8-week old male CD1 nu/nu mice. The animals were then serially monitored by manual palpation for evidence of tumor. When the tumors reached a satisfactory volume, mice were randomized and then treated with daily oral administration of saline (negative control), cyclophosphamide (positive control, 100 mg/kg) or sodium decanoate (200 mg/kg). Mice were sacrificed at day 56. Serial tumor volume was obtained by bi-dimensional diameter measurements with calipers, using the formula 0.4 (a×b$^2$) where "a" was the major tumor diameter and "b" the minor perpendicular diameter.

Figure 14:
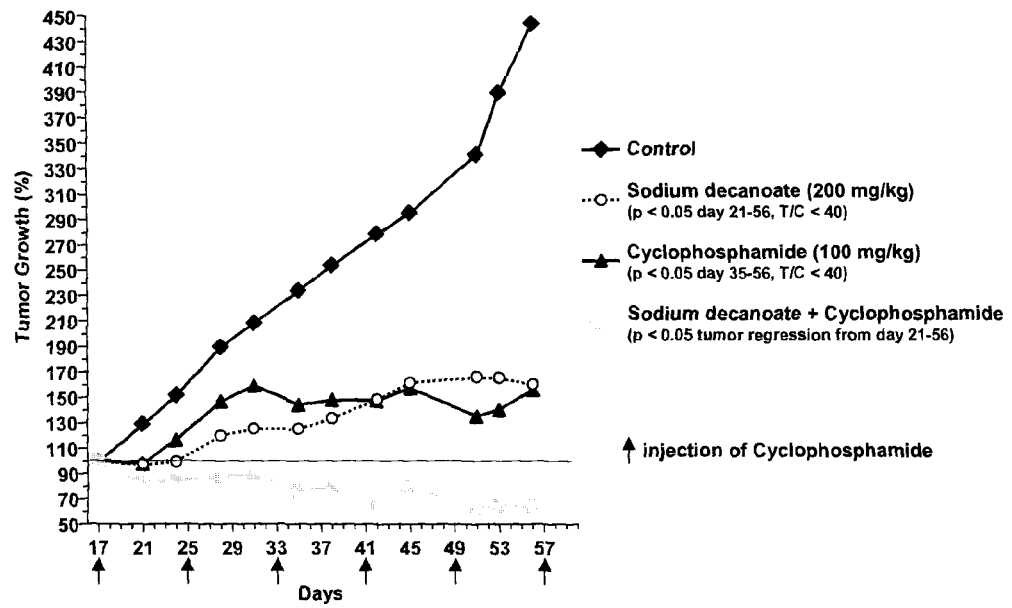
FIG. 14 is a line graph showing antitumor efficacy of sodium decanoate, cyclophosphamide and combination thereof on xenograft human prostate PC-3 tumor in mice.

FIG. 14 represents the effect of sodium decanoate, cyclophosphamide and combination on xenograft human prostate PC-3 tumor. Sodium decanoate induces a significant reduction (p<0.05%, T/C<40% from day 21 to 56) of tumor growth. Cyclophosphamide induces a significant reduction (p<0.05%, T/C<40% from day 35 to 56) of tumor growth. Combination of sodium decanoate and cyclophosphamide induces a regression of the tumor (synergistic effect; p<0.05%, T/C <40% from day 21 to 56). Sodium decanoate synergizes with cyclophosphamide in xenograft human prostate PC-3 cancer (tumor regression).

Figure 15:
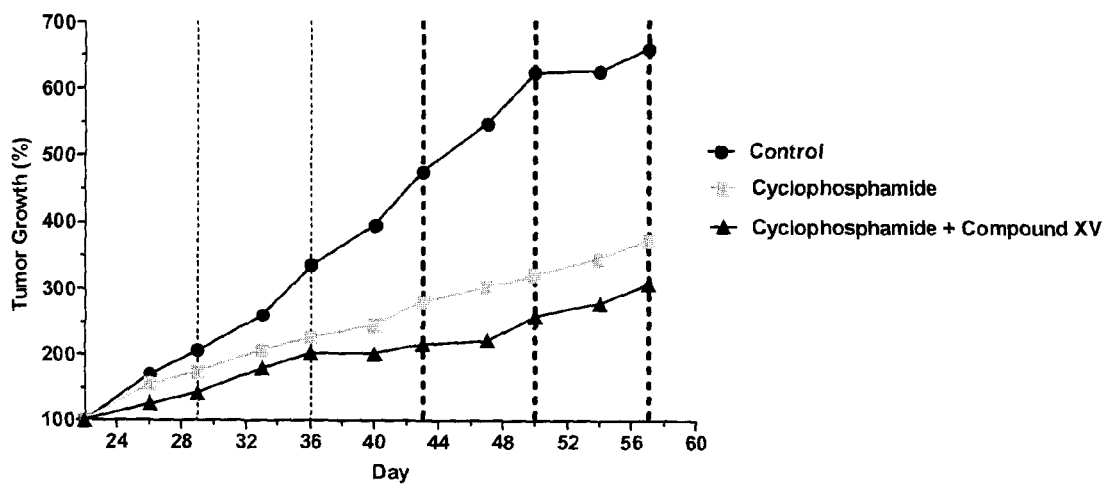
FIG. 15 is a line graph showing antitumor efficacy of oral administration of cyclophosphamide (positive control) and combination of cyclophosphamide with Compound XV on xenograft human prostate PC-3 tumor in mice.

FIG. 15 shows the effect of oral administration of cyclophosphamide (positive control) and combination of cyclophosphamide with Compound XV on xenograft PC-3 tumor. Cyclophosphamide induces a significant reduction (p≤0.05, T/C=42-78%). However, when used in combination, Compound XV and cyclophosphamide induce a significant (p≤0.04) reduction (T/C of 27% to 56%) of tumor growth from day 26 to day 56.

Example 13

Antitumor Effect of Compounds on Xenograft Human Pancreatic Carcinoma MiaPaca-2 Tumor MiaPaca-2 cells were grown in DMEM containing 10% fetal bovine serum. At day 0, 50 µL of viable MiaPaca-2 (2×10$^6$) cells were subcutaneously injected to produce localized tumors in 6- to 7-week old female NCR nude/homozygote mice. The animals were then serially monitored by manual palpation for evidence of tumor. When the tumors reached a satisfactory volume, mice were randomized and then treated daily with oral administration of sodium decanoate (400 mg/kg), Abraxane™ (positive control, i.p administration of 10 to 50 mg/kg) or combination of Abraxane™ and sodium decanoate. Mice were sacrificed at day 95. Serial tumor volume was obtained by bi-dimensional diameter measurements with calipers, using the formula 0.4 (a×b$^2$) where "a" was the major tumor diameter and "b" the minor perpendicular diameter.

Figure 19:
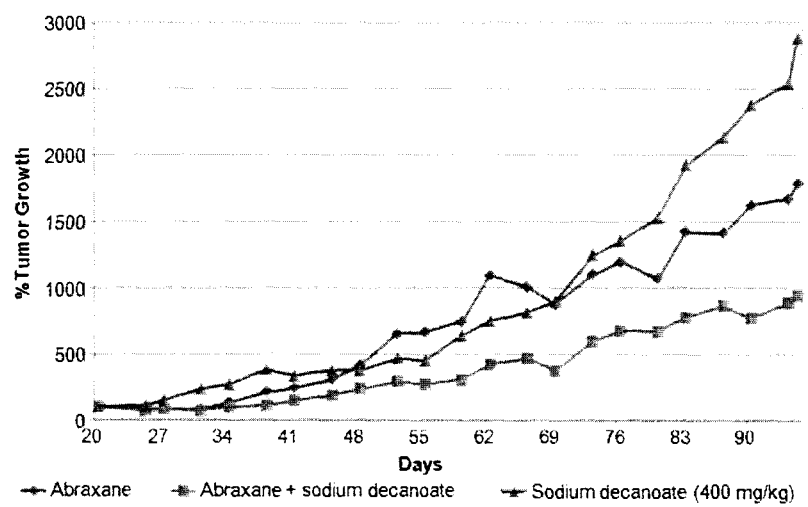

FIG. 19 shows the effect of combination of Abraxane™ and sodium decanoate reduces tumor growth of human pancreatic carcinoma MiaPaca-2.

Example 14

Epithelial to Mesenchymal Transition

Evidence suggests that cancer cells can undergo epithelial to mesenchymal transition (EMT) to migrate and invade tissues (metastasis).

Figure 20:
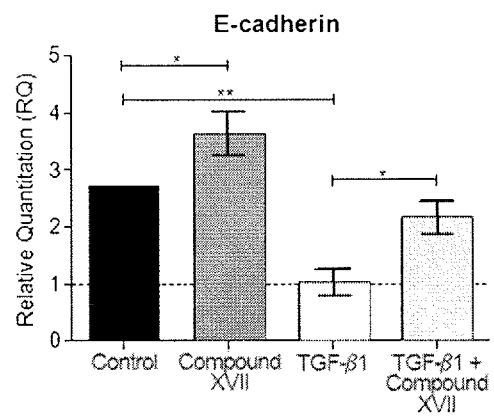
FIG. 20 is a bar graph showing the effect of Compound XVII on E-cadherin in normal HK-2 cells and in TGF-β-induced EMT cells. Real-time PCR using human E-cadherin TagMan® Gene Expression Assay normalized to human GAPDH endogenous control; reference is TGF-β-treated cells 24h (RQ–1). *means p<0.05, and ** means p<0.01 (t-test).
Figure 21:
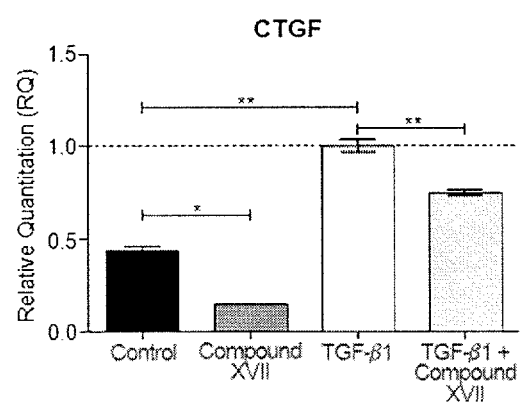
FIG. 21 is a bar graph showing the effect of Compound XVII on CTGF in normal HK-2 cells and in TGF-β induced EMT cells. Real-time PCR using human CTGH TaqMan® Gene Expression Assay normalized to human GAPDH endogenous control; reference is TGF-β-treated cells 24h (RQ=1). *means p<0.05, and ** means p<0.01 (t-test).
Figure 22:
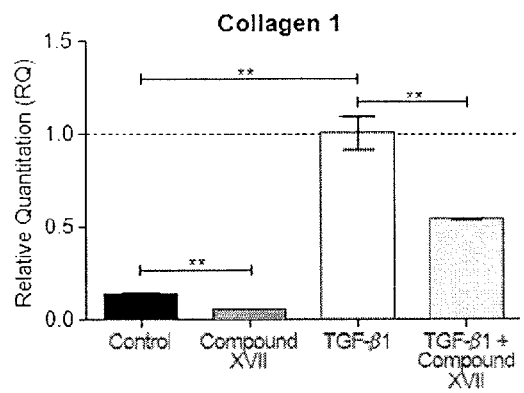
FIG. 22 is a bar graph showing the effect of Compound XVII on collagen 1 in normal HK-2 cells and in TGF-β-induced EMT cells. Real-time PCR using human Collagen 1 TagMan® Gene Expression Assay normalized to human GAPDH endogenous control; reference is TGF-β-treated cells 24h (RQ=1). ** means p<0.01 (t-test).

Further analysis was undertaken to determine the effect of Compounds on EMT. The effect of Compound XVII on TGF-11 induced EMT was analyzed on human epithelial cancer cells (HK-2). To assess the progression of EMT, the pro-epithelial marker E-cadherin and the mesenchymal/pro-fibrotic markers CTGF and collagen 1 were assayed by quantitative real-time PCR. To determine the efficacy of Compound XVII in inhibiting TGF-β-induced EMT, verification of the ability of TGF-1 to induce EMT in HK-2 cells. As shown in FIGS. 20, 21 and 22, EMT was induced by TGF-β as determined by a downregulation of E-cadherin and upregulation of CTGF and collagen 1 transcript expression. Furthermore, TGF-β induced EMT was significantly inhibited by Compound XVII in both cells as demonstrated by an upregulation of E-cadherin and downregulation of CTGF and collagen 1. Furthermore, Compound XVII alone was able to downregulate basal expression of CTGF and collagen 1. These results are shown in FIGS. 20, 21 and 22.

Figure 23:
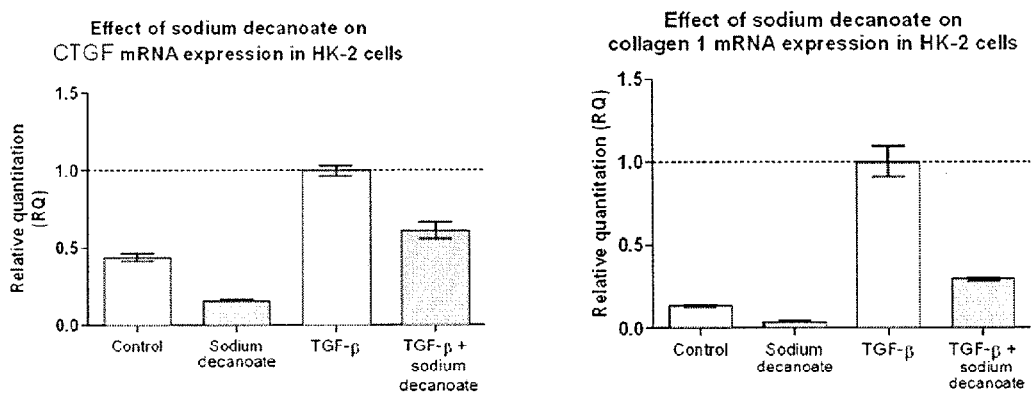
FIG. 23 is a bar graph showing the effect of sodium decanoate on CTGF and collagen 1 expression in normal HK-2 cells and in TGF-β induced EMT cells. Real-time PCR using human CTGF TaqMan® Gene Expression Assay and Collagen 1 TaqMan® Gene Expression Assay normalized to human GAPDH endogenous control; reference is TGF-β-treated cells 24h (RQ=1). Sodium decanoate was added at 0.5 mM.
Figure 24:
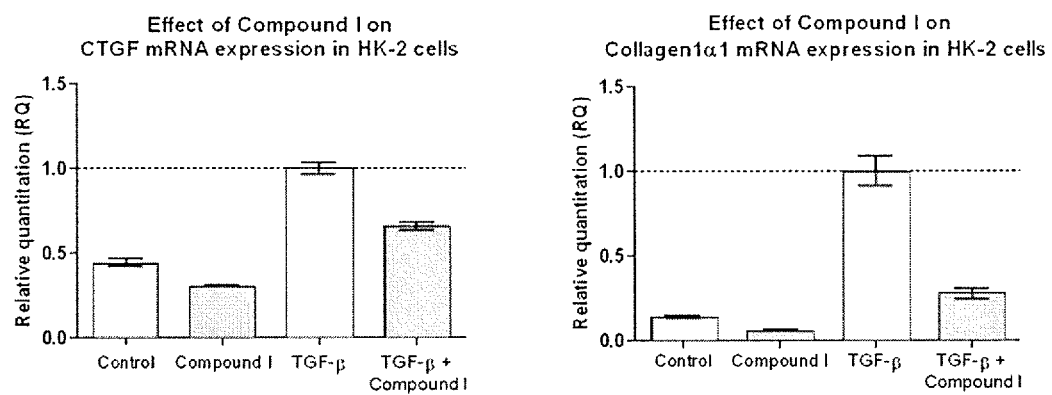
FIG. 24 is a bar graph showing the effect of Compound I on CTGF and collagen 1 expression in normal HK-2 cells and in TGF-β induced EMT cells. Real-time PCR using human CTGF TaqMan® Gene Expression Assay and Collagen 1α1 TagMan® Gene Expression Assay normalized to human GAPDH endogenous control; reference is TGF-β-treated cells 24h (RQ=1). Sodium decanoate was added at 0.5 mM.

In another experiment, sodium decanoate and Compound I induced significant inhibition of EMT in HK-2 cells, as demonstrated by reduction of basal and TGF-β-stimulated CTGF and collagen 1 expression (FIGS. 23 and 24).

Headings are included herein for reference and to aid in locating certain sections These headings are not intended to limit the scope of the concepts described therein, and these concepts may have applicability in other sections throughout the entire specification Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A method for treating cancer, wherein said method comprises administering to a subject in need of such treatment, a compound represented by Formula IC, or a pharmaceutically acceptable salt thereof:

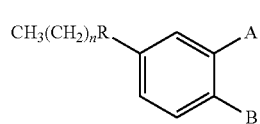

Formula IC wherein
n is 2, 3, 4, 5, or 6;
R is —C(O)—, —OC(O)—, —CH(OH)—, NH, $NC_1$-$C_3$ alkyl, O, S, or $CH_2$;
A is $(CH_2)_m C(O)OH$, $W(CH_2)_m C(O)OH$, or $YCH(C(O)OH)(CH_2)_p CH_3$ when B is H;
B is $(CH_2)_m C(O)OH$, $W(CH_2)_m C(O)OH$ or $YCH(C(O)OH)(CH_2)_p CH_3$ when A is H; or
A and B are covalently bonded to form a 5-, 6-, or 7-membered cycloalkyl substituted with a C(O)OH group;
W is O, S, or NH;
Y is O, S, NH or $CH_2$;
m is 0, 1, or 2; and
p is 1, 2, 3, 4, 5, 6, or 7.

2. The method of claim 1, wherein the pharmaceutically acceptable salt is a base addition salt.

3. The method of claim 2, wherein the base addition salt comprises a metal counterion selected from sodium, potassium, magnesium, calcium and lithium.

4. The method of claim 3, wherein the metal counterion is sodium.

5. The method of claim 1, wherein the compound is any one of the following Compounds:

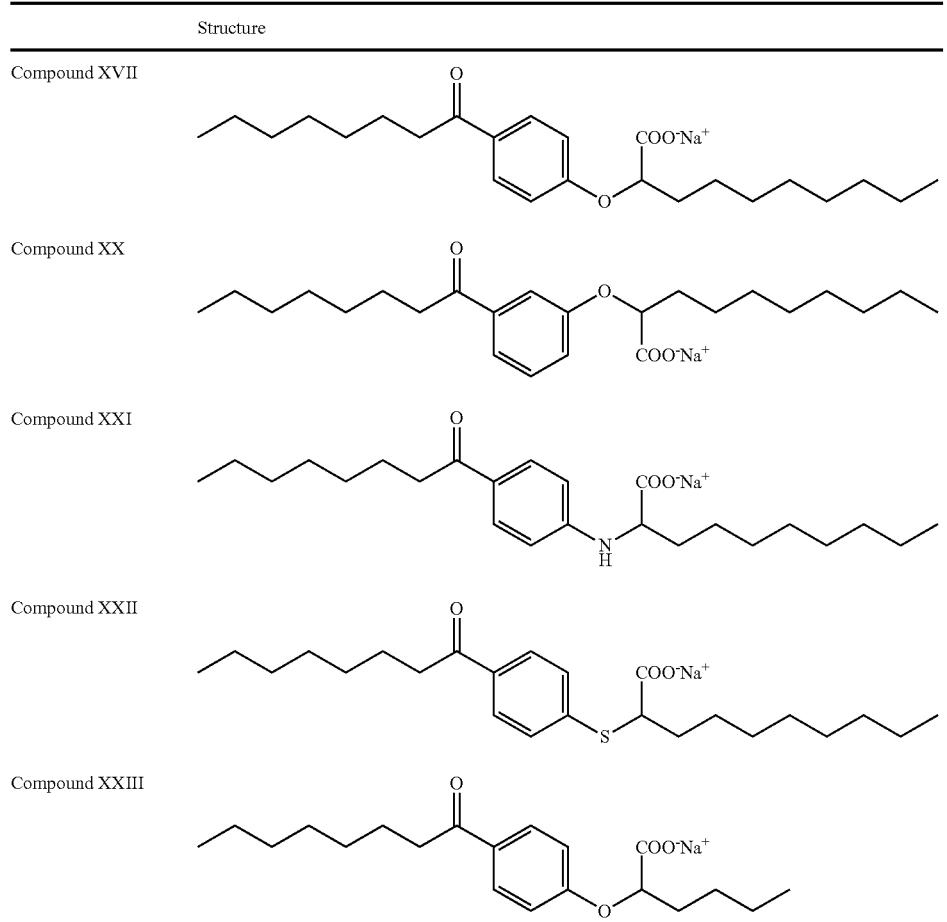

|  | Structure |
|---|---|
| Compound XXIV | 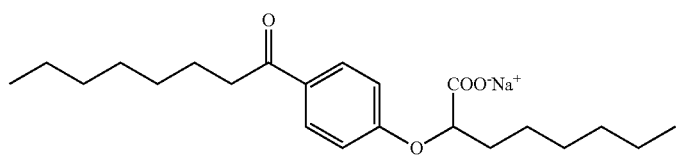 |
| Compound XXV | 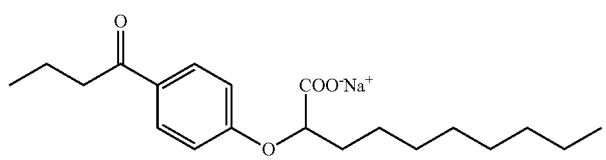 |
| Compound XXVI | 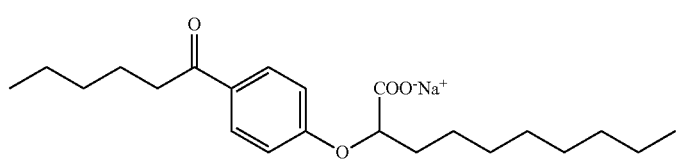 |
| Compound XXVII | 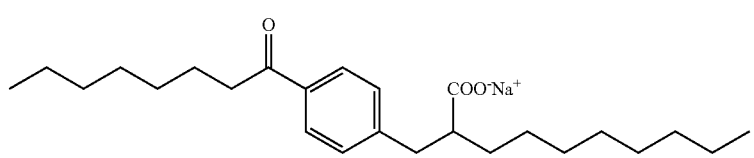 |
| Compound XXIX | 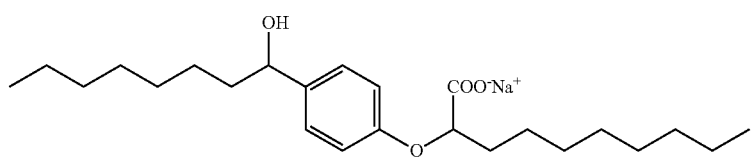 |
| Compound XXX | 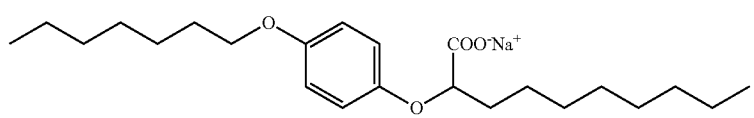 |
| Compound XXXI | 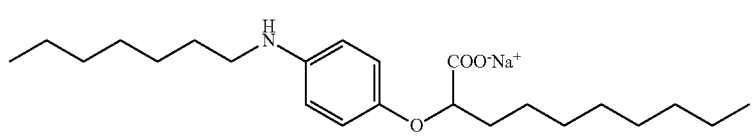 |
| Compound XXXII | 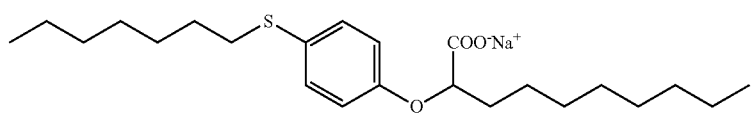 |
| Compound XXXIV | 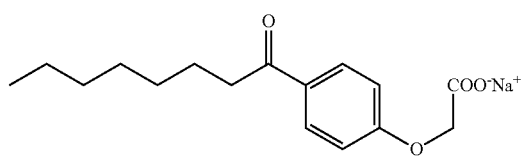 |
| Compound XXXV | 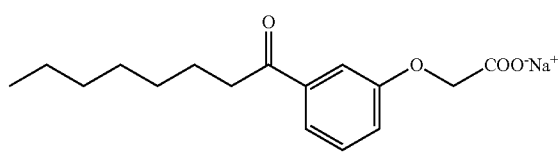 |

| | Structure |
|---|---|
| Compound XXXVI | 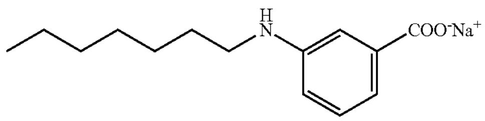 |
| Compound XXXVII | 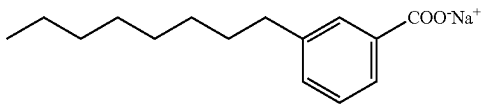 |
| Compound XXXVIII | 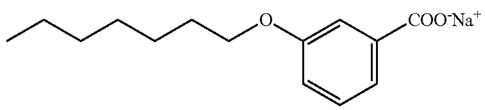 |
| Compound XXXIX | 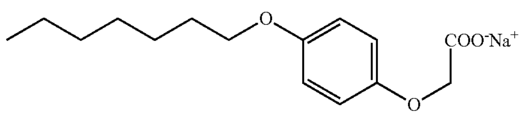 |
| Compound XL | 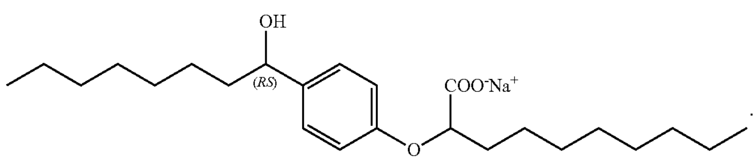 |

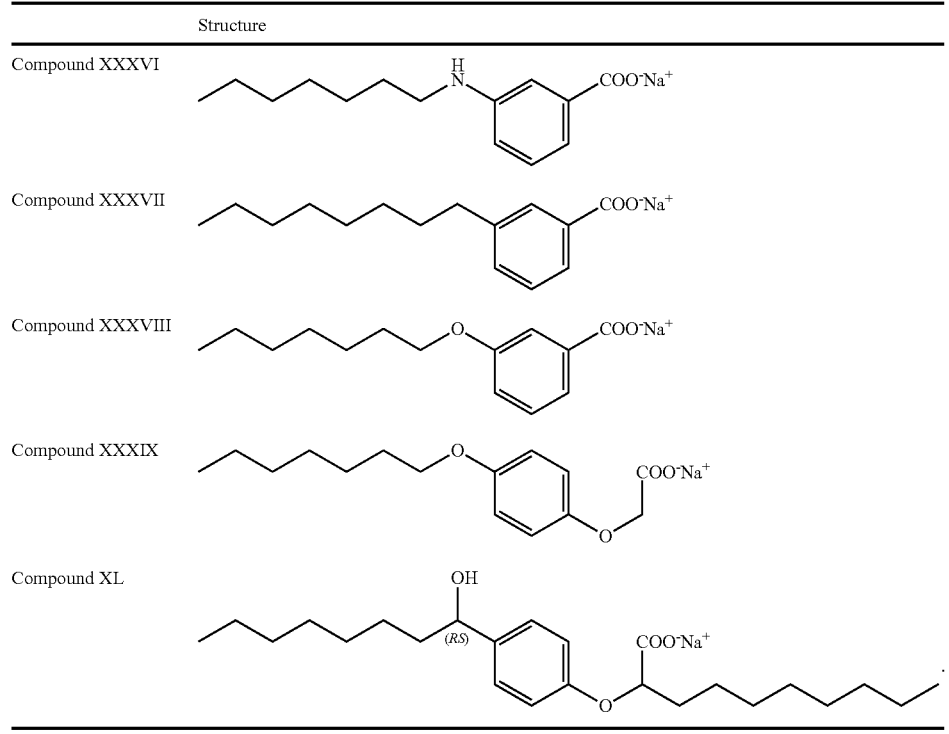

6. The method of claim 5, wherein the compound is Compound or XX.

7. The method of claim 5, wherein the compound is Compound XVII.

8. The method of claim 1, wherein said subject is a human patient.

9. The method of claim 1, wherein the cancer is bladder cancer, breast cancer, colorectal cancer, kidney cancer, melanoma, non-Hodgkin's lymphoma, leukemia, ovarian cancer, pancreatic cancer, prostate cancer or uterine cancer.

10. The method of claim 1, wherein the cancer is breast cancer, colorectal cancer, leukemia cancer, melanoma cancer or pancreatic cancer.

11. The method of claim 1, wherein the compound is used in combination with an anticancer agent.

12. The method of claim 11, wherein said anticancer agent is decarbazine, doxorubicin, daunorubicin, cyclophosphamide, busulfex, busulfan, vinblastine, vincristine, bleomycin, etoposide, topotecan, irinotecan, taxotere, taxol, 5-fluorouracil, methotrexate, gemcitabine, cisplatin, carboplatin or chlorambucil.

13. The method of claim 1, wherein said compound exhibits one or more of the following biological activities in said subject: stimulating and/or enhancing IL-12 production under inflammatory conditions; stimulating the antitumor cytolytic activity of lymphocytes and/or NK cells; inducing regression of established tumors and/or of primary solid tumors; inhibiting TGF-induced CTGF production; and/or inhibiting CTGF-mediated activities.

14. A pharmaceutical composition comprising a compound of claim 1 and a pharmaceutically acceptable carrier.

15. The pharmaceutical composition according to claim 14, wherein said composition further comprises an anticancer agent.

16. The pharmaceutical composition according to claim 15, wherein said anticancer agent is decarbazine, doxorubicin, daunorubicin, cyclophosphamide, busulfex, busulfan, vinblastine, vincristine, bleomycin, etoposide, topotecan, irinotecan, taxotere, taxol, 5-fluorouracil, methotrexate, gemcitabine, cisplatin, carboplatin or chlorambucil.

17. The pharmaceutical composition according to claim 14, which induces regression of established tumors and/or of primary solid tumors.

18. The pharmaceutical composition according to claim 14, which inhibits tumor cell migration and establishment of metastasis.

19. The method of claim 1, wherein said compound inhibits tumor cell migration and establishment of metastasis.

* * * * *

UNITED STATES PATENT AND TRADEMARK OFFICE
CERTIFICATE OF CORRECTION

PATENT NO.        : 9,114,118 B2
APPLICATION NO.   : 13/882355
DATED             : August 25, 2015
INVENTOR(S)       : Lyne Gagnon et al.

It is certified that error appears in the above-identified patent and that said Letters Patent is hereby corrected as shown below:

In the Specification

Column 4,
After Line 13, please insert

--Figure 19 is a line graph showing antitumor efficacy of sodium decanoate, Abraxane™ and combination thereof on human pancreatic MiaPaca-2 tumor in mice.--.

Column 8,

Lines 20-23, " 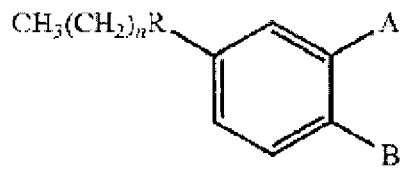 " should read

-- 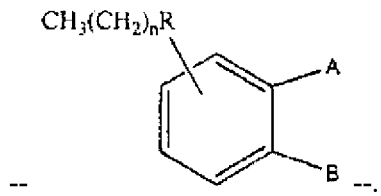 --.

Column 27,
Line 55, "salt of e-(3-" should read --salt of E-(3- --.

Column 33,
Line 23, "2-[4" should read --2-[4- --.

Column 34,
Line 1, "then at 00°C." should read --then at 0°C.--.

Signed and Sealed this
Tenth Day of May, 2016

Michelle K. Lee
*Director of the United States Patent and Trademark Office*

Column 37,
Line 57, "Z = 3 - F - CH₅," should read --Z = 3 - F - C₆H₅,--.

Column 42,
Line 19, "hu1H NMR" should read --'H NMR--.

Column 53,
Line 33, "TGF-(3" should read --TGF-β--.

Column 55,
Line 50, "(TIC)" should read --(T/C)--.

Column 58,
Lines 34-35, "TGF-11" should read --TGF-β--.

Column 58,
Line 42, "TGF-1" should read --TGF-β--.

Column 58,
Line 44, "TGF-(3" should read --TGF-β--.

In the Claims

Columns 61-62,

Lines 31, should read -- 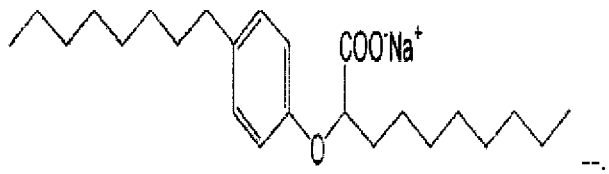 --.

Column 63,
Lines 32-33, "wherein the compound is Compound or XX." should read --wherein the compound is Compound XVII or XX.--.